United States Patent
Li

(10) Patent No.: US 9,719,101 B2
(45) Date of Patent: Aug. 1, 2017

(54) SOYBEAN GAPD PROMOTER AND ITS USE IN CONSTITUTIVE EXPRESSION OF TRANSGENIC GENES IN PLANTS

(71) Applicant: E I DU PONT DE NEMOURS AND COMPANY, Wilmington, DE (US)

(72) Inventor: Zhongsen Li, Hockessin (DE)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 169 days.

(21) Appl. No.: 14/637,517

(22) Filed: Mar. 4, 2015

(65) Prior Publication Data

US 2015/0267215 A1   Sep. 24, 2015

Related U.S. Application Data

(60) Provisional application No. 61/955,256, filed on Mar. 19, 2014.

(51) Int. Cl.
*C12N 15/82* (2006.01)
*C12N 9/02* (2006.01)

(52) U.S. Cl.
CPC ....... *C12N 15/8216* (2013.01); *C12N 9/0008* (2013.01)

(58) Field of Classification Search
None
See application file for complete search history.

(56) References Cited

U.S. PATENT DOCUMENTS 6,177,611 B1 *  1/2001  Rice .................... C07K 14/415
                                                              435/320.1

OTHER PUBLICATIONS

Potenza et al., In Vitro Cell Dev Biol Plant 40:1-22 (2004).*
Rossitza Atanassova et al., Functional analysis of the promoter region of a maize (*Zea mays* L.) H3 histone gene in transgenic Arabidopsis thaliana, Plant Molecular Biology, 1998, pp. 275-285, vol. 37.
Jeremy Schmutz, Genome sequence of the palaeopolyploid soybean, Nature, Jan. 14, 2010, pp. 178-183, vol. 463.

* cited by examiner

*Primary Examiner* — Cathy Kingdon Worley
*Assistant Examiner* — Russell Boggs

(57) ABSTRACT

The invention relates to gene expression regulatory sequences from soybean, specifically to the promoter of a soybean eukaryotic glyceraldehyde-3-phosphate dehydrogenasegene and fragments thereof and their use in promoting the expression of one or more heterologous nucleic acid fragments in a constitutive manner in plants. The invention further discloses compositions, polynucleotide constructs, transformed host cells, transgenic plants and seeds containing the recombinant construct with the promoter, and methods for preparing and using the same.

17 Claims, 12 Drawing Sheets

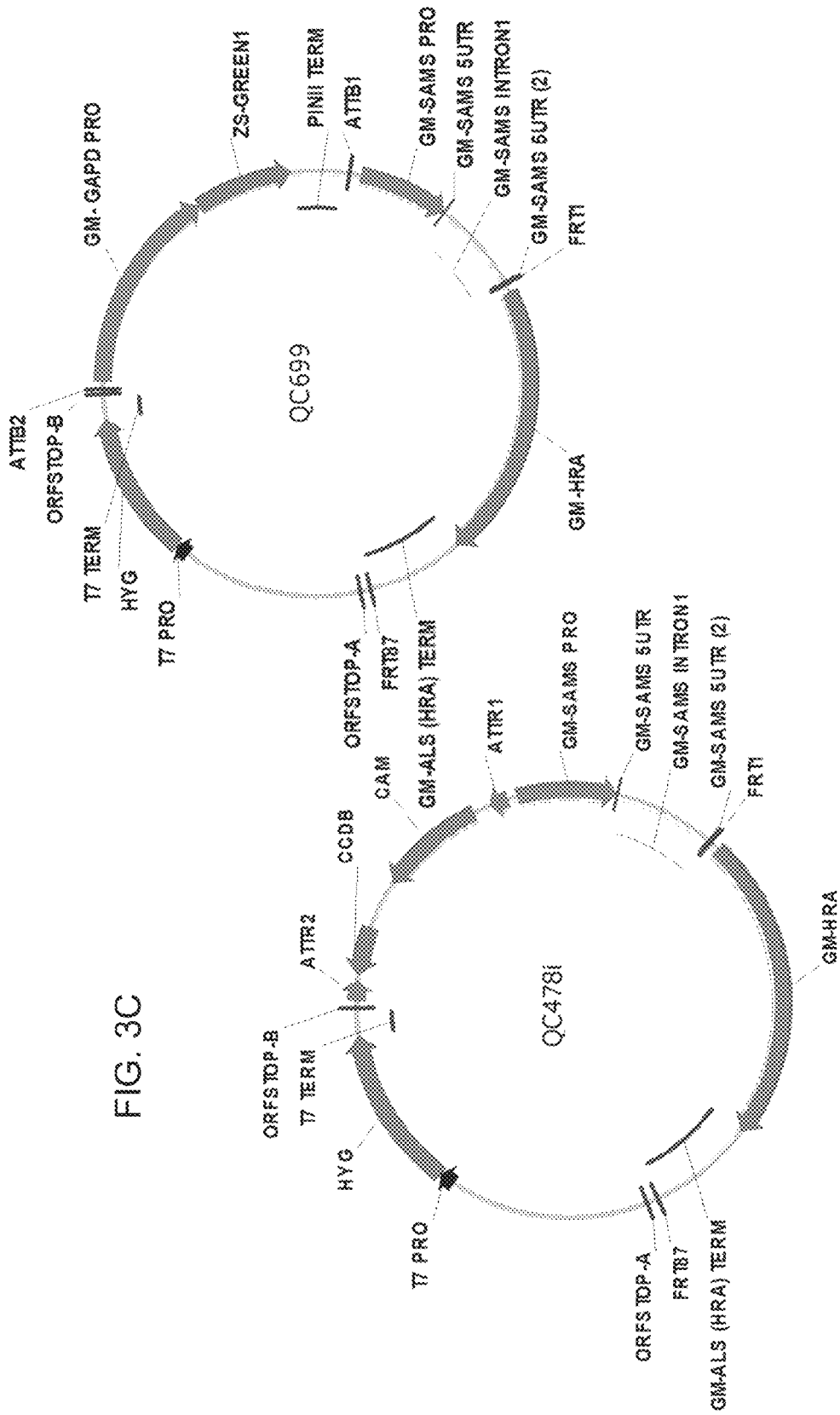

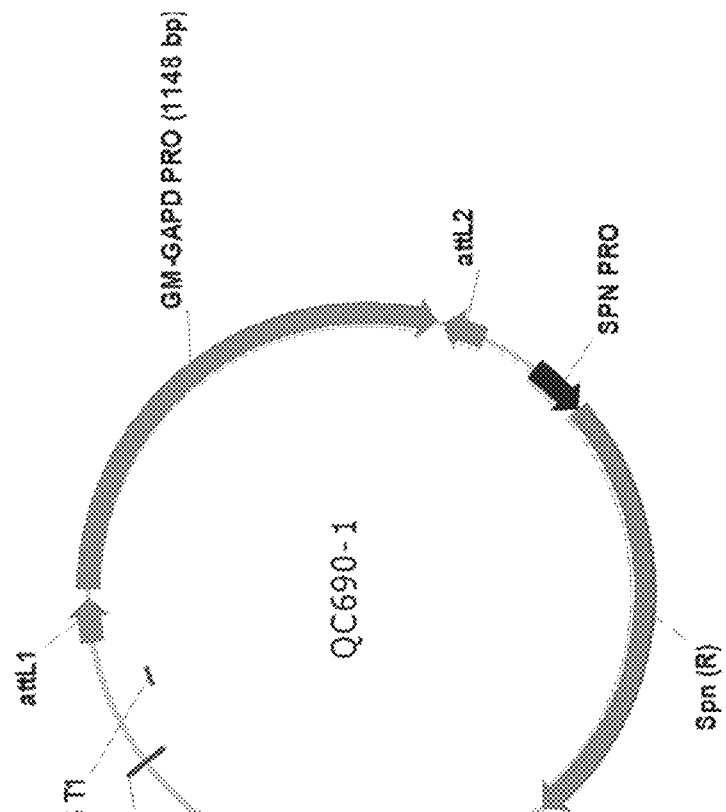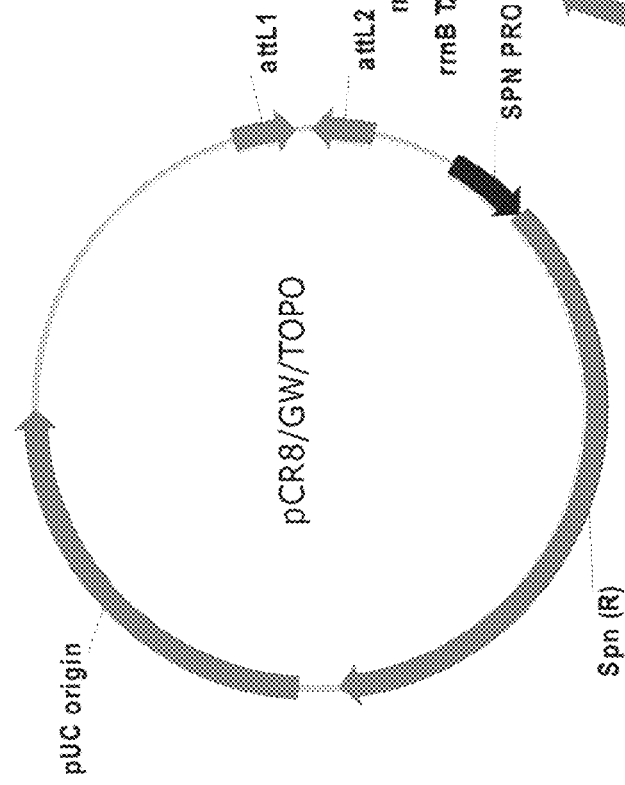
FIG. 4A
FIG. 4B

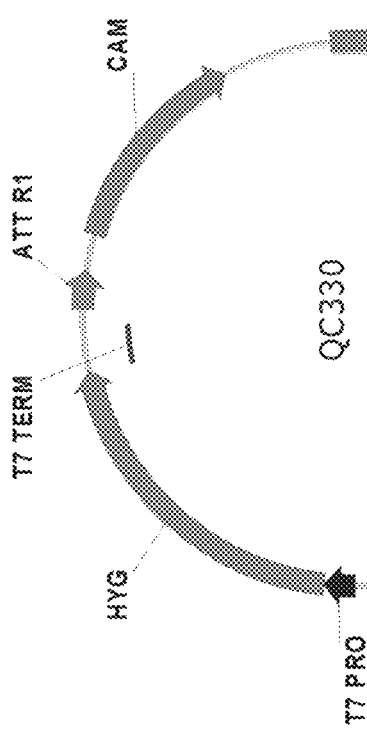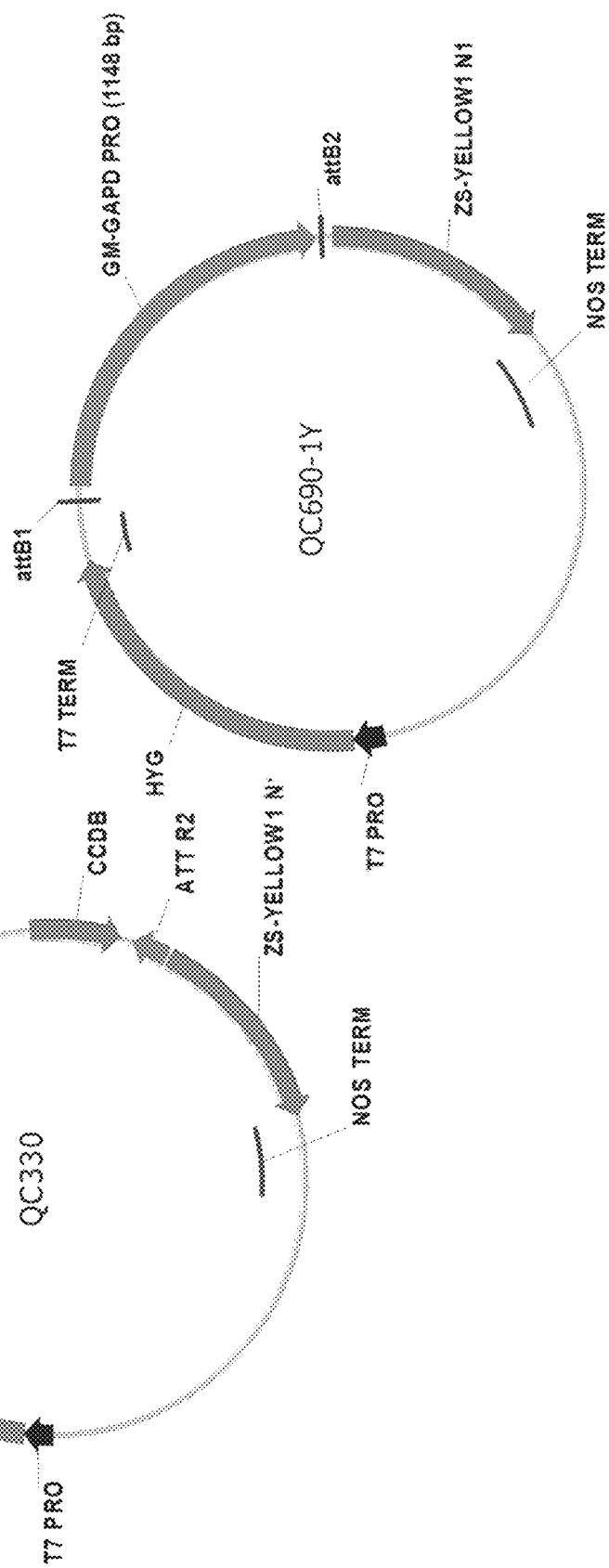

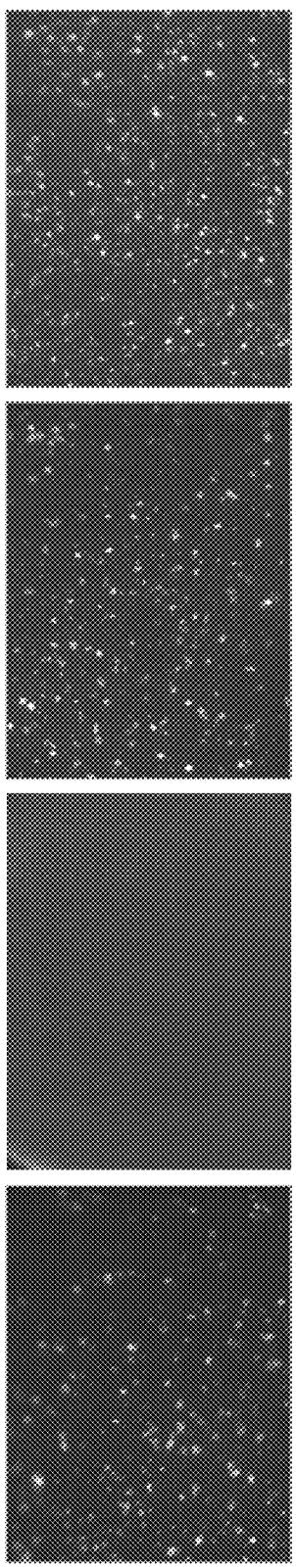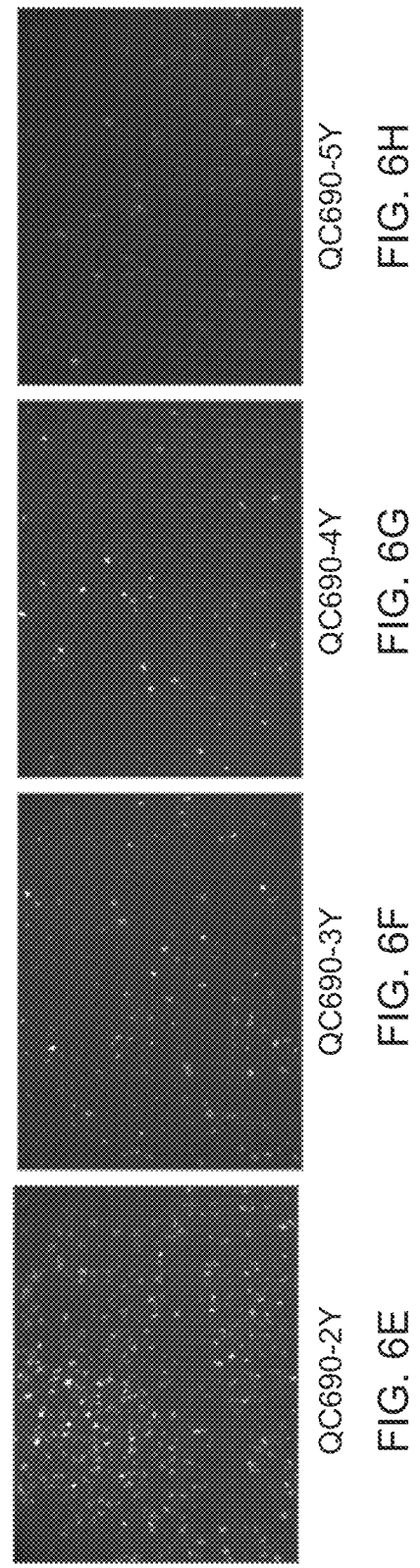

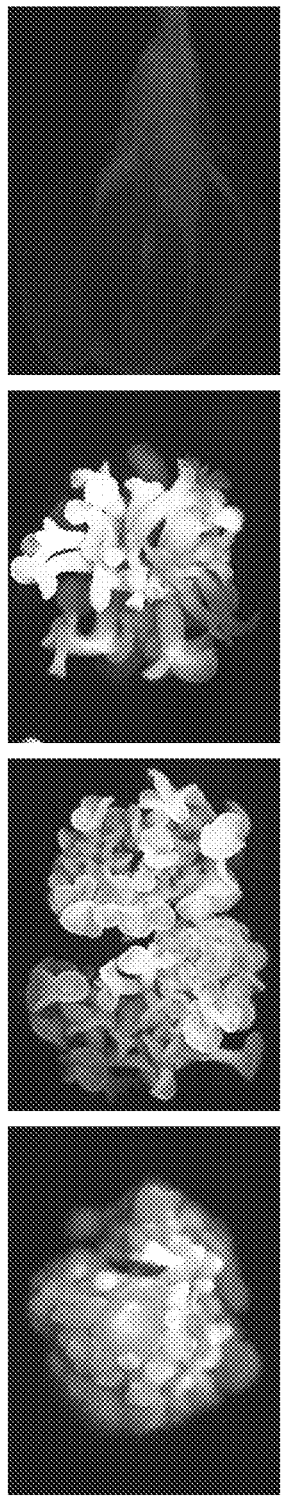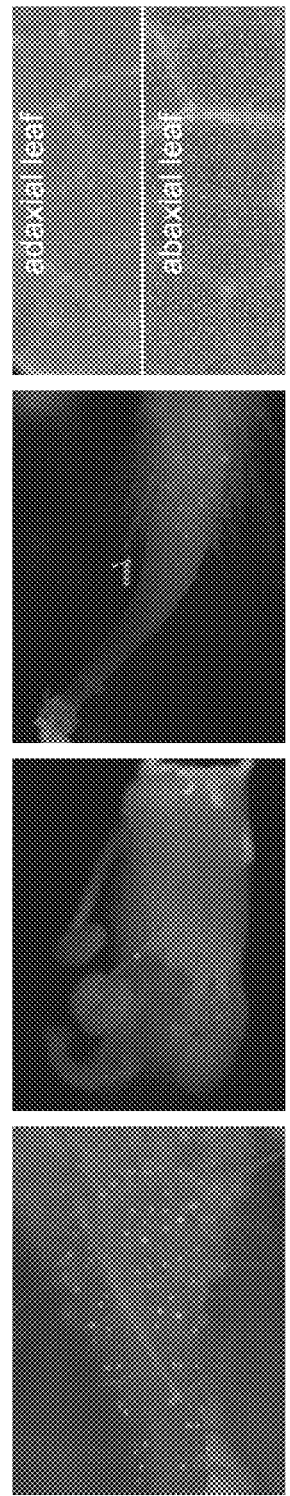

FIG. 8

SEQUENCE LISTING

```
<160> NUMBER OF SEQ ID NOS: 40

<210> SEQ ID NO 1
<211> LENGTH: 1469
<212> TYPE: DNA
<213> ORGANISM: Glycine max

<400> SEQUENCE: 1
cccgggctcg ctcctttgtg atttctcatt agaaaataga atctagaaac tataggatag      60
```

```
cgttacacac ttacaaaata taagtatttc actcaattt    tgacaagttg ttattttttc     120
ggtaaattat gataatgaca ttttaatttt agtacatgaa tgagttaatg ttaaaaatat     180
aaggaataag aagttagctt ttataatttt atgataatat taataataat aataataata     240 gtgattttt aagatatgaa aaactaaatt tatgttttt ttcccaaata actgctaatt      300
agtatgaata ggataggatt agtacaatct attgcaggaa agtatgtgtt catgttttat     360
tagacaaaaa ttaaacaaaa ttttaaaata aaaacagag gaaatcatgc cttggcttgg     420
taacttacta tcttctggtc cttcatatga taaacaaaca gtgtttttt ccctaatca      480 taagaatcat ataattattt taaatgtat taataactat ttttttatat ctttaattttg    540 ttgtgaagtc ttttaatgat cactcattat tcatgaaagt atacagtt aatgaactat      600 taataatata acttattctc atcggtaac aagtatttt catgtattat gagtagtgat      660
attatatgta accacttctt tatccattg attttatgga tattttaaa ataaaatttg      720 aatttatatt agtattaatt aaagtaact actttaatca ttttatttg tcttgattat      780 ttaatcttat ggttttcatt tgtgatgatg atcaaagata gtatgatagt atgatttgt     840 tatatttgtg caacacttag ttatgtttaa taattttttt taaaaaaata taatatatt     900 gaaaaggtca tatgcaagcg gtagcctcac ccaagaataa ttaaatagaa cccaaattct     960
ctgaataaat agacctaaat actccatgaa tgtgtttcat tgttttgttat ttgatgttca     1020 tcaaatatca aatataatta aagctcatca tattttcgta cagtatagta ttagtattat     1080
atcctgctca ccaaaccaaa catctaagaa taaccttatt tcatttagaa aaaaaaaacc     1140
caagtaaaat tgaaaaaaga atcaaaacaa taaaagaga gaaaagcgaa tggaatattc     1200
gcatatctgt tggcgtgaaa cagaaaccac aaaaaaaaaa aaaaaaaacg gtacaccgta     1260
gtagtccttg gcaaagcatc acgagtcaca aggcggtccc gtaggagtca cgcacttcac     1320
ttggcccatt tacctgtcat tgcggtctt tactcttctc aataccttat taaaacccta     1380
tctcactcac tcactcacac cgttccattt ctcaacaact tctgctactt cctactccaa     1440
ccgcacttct gctccgcaat tatccatgg                                      1469
```

<210> SEQ ID NO 2
<211> LENGTH: 1148
<212> TYPE: DNA
<213> ORGANISM: Glycine max

<400> SEQUENCE: 2

```
gattagtaca atctattgca ggaaagtatg tgttcatgtt ttattagaca aaaattaaac      60
aaaattttaa aataaaaaac agaggaaatc atgccttggc ttggtaactt actatcttct     120
ggtccttcat atgataaaca aacagtgttt tttcccccta atcataagaa tcatataatt     180 attttttaaat gtattaataa ctatttttt atatctttaa tttgttgtga agtcttttaa     240
tgatcactca ttattcatga agtatatac agttaatgaa ctattaataa tataacttat     300
tctcatcggt taacaagtat tttcatgta ttatgagtag tgatattata tgtaaccact     360
tcttatatcc attgatttta tggatatttt taaaataaaa tttgaattta tattagtatt     420
aattaaaagt aactacttta atcattttta tttgtcttga ttatttaatc ttatggtttt     480
catttgtgat gatgatcaaa gatagtatga tagtatgatt tgttatatt tgtgcaacac     540 ttagttatgt ttaataattt tttttaaaaa aatataaata tattgaaaag gtcatatgca     600
agcggtagcc tcacccaaga ataattaaaa tagacccaaa ttctctgaat aaatagacct     660
```

| | |
|---|---|
| aaatactcca tgaatgtgtt tcattgtttg ttatttgatg ttcatcaaat atcaaatata | 720 |
| attaaagctc atcatatttt cgtacagtat agtattagta ttatatcctg ctcaccaaac | 780 |
| caaacatcta agaataacct tatttcattt agaaaaaaaa aacccaagta aaattgaaaa | 840 |
| aagaatcaaa acaataaaaa gagagaaaag cgaatggaat attcgcatat ctgttggcgt | 900 |
| gaaacagaaa ccacaaaaaa aaaaaaaaaa aacggtacac cgtagtagtc cttggcaaag | 960 |
| catcacgagt cacaaggcgg tcccgtagga gtcacgcact tcacttggcc catttacctg | 1020 |
| tcattgcggt cttttactct tctcaatacc ttattaaaac cctatctcac tcactcactc | 1080 |
| acaccgttcc atttctcaac aacttctgct acttcctact ccaaccgcac ttctgctccg | 1140 |
| caattatc | 1148 |

<210> SEQ ID NO 3
<211> LENGTH: 850
<212> TYPE: DNA
<213> ORGANISM: Glycine max

<400> SEQUENCE: 3

| | |
|---|---|
| attctcatcg gttaacaagt attttttcatg tattatgagt agtgatatta tatgtaaccca | 60 |
| cttcttatat ccattgattt tatggatatt tttaaaataa aatttgaatt tatattagta | 120 |
| ttaattaaaa gtaactactt taatcatttt tatttgtctt gattatttaa tcttatggtt | 180 |
| ttcatttgtg atgatgatca aagatagtat gatagtatga ttttgttata tttgtgcaac | 240 |
| acttagttat gtttaataat ttttttttaaa aaaatataaa tatattgaaa aggtcatatg | 300 |
| caagcggtag cctcacccaa gaataattaa aatagaccca aattctctga ataaatagac | 360 |
| ctaaatactc catgaatgtg tttcattgtt tgttatttga tgttcatcaa atatcaaata | 420 |
| taattaaagc tcatcatatt ttcgtacagt atagtattag tattatatcc tgctcaccaa | 480 |
| accaaacatc taagaataac cttatttcat ttagaaaaaa aaacccaag taaaattgaa | 540 |
| aaagaatca aacaataaa aagagagaaa agcgaatgga atattcgcat atctgttggc | 600 |
| gtgaaacaga accacaaaa aaaaaaaaaa aaaacggtac accgtagtag tccttggcaa | 660 |
| agcatcacga gtcacaaggc ggtcccgtag gagtcacgca cttcacttgg cccatttacc | 720 |
| tgtcattgcg gtcttttact cttctcaata ccttattaaa accctatctc actcactcac | 780 |
| tcacaccgtt ccatttctca acaacttctg ctacttccta ctccaaccgc acttctgctc | 840 |
| cgcaattatc | 850 |

<210> SEQ ID NO 4
<211> LENGTH: 637
<212> TYPE: DNA
<213> ORGANISM: Glycine max

<400> SEQUENCE: 4

| | |
|---|---|
| agtatgattt tgttatattt gtgcaacact tagttatgtt taataatttt ttttaaaaaa | 60 |
| atataaatat attgaaaagg tcatatgcaa gcggtagcct cacccaagaa taattaaaat | 120 |
| agacccaaat tctctgaata atagaccta aatactccat gaatgtgttt cattgtttgt | 180 |
| tatttgatgt tcatcaaata tcaaatataa ttaaagctca tcatattttc gtacagtata | 240 |
| gtattagtat tatatcctgc tcaccaaacc aaacatctaa gaataacctt atttcattta | 300 |
| gaaaaaaaaa acccaagtaa aattgaaaaa gaatcaaaa caataaaaag agagaaaagc | 360 |
| gaatggaata ttcgcatatc tgttggcgt aaacagaaac cacaaaaaa aaaaaaaaaa | 420 |
| acggtacacc gtagtagtcc ttggcaaagc atcacgagtc acaaggcggt cccgtaggag | 480 |

```
tcacgcactt cacttggccc atttacctgt cattgcggtc ttttactctt ctcaatacct    540
tattaaaacc ctatctcact cactcactca caccgttcca tttctcaaca acttctgcta    600
cttcctactc caaccgcact tctgctccgc aattatc                             637
```

```
<210> SEQ ID NO 5
<211> LENGTH: 425
<212> TYPE: DNA
<213> ORGANISM: Glycine max

<400> SEQUENCE: 5
aaagctcatc atattttcgt acagtatagt attagtatta tatcctgctc accaaaccaa     60
acatctaaga ataaccttat ttcatttaga aaaaaaaaac ccaagtaaaa ttgaaaaaag    120
aatcaaaaca ataaaaagag agaaaagcga atggaatatt cgcatatctg ttggcgtgaa    180
acagaaacca caaaaaaaaa aaaaaaaaac ggtacaccgt agtagtcctt ggcaaagcat    240
cacgagtcac aaggcggtcc cgtaggagtc acgcacttca cttggcccat ttacctgtca    300
ttgcggtctt ttactcttct caataccttaa ttaaaaccct atctcactca ctcactcaca    360
ccgttccatt tctcaacaac ttctgctact tcctactcca accgcacttc tgctccgcaa    420
ttatc                                                                425
```

```
<210> SEQ ID NO 6
<211> LENGTH: 211
<212> TYPE: DNA
<213> ORGANISM: Glycine max

<400> SEQUENCE: 6
caccgtagta gtccttggca aagcatcacg agtcacaagg cggtcccgta ggagtcacgc     60
acttcacttg gcccatttac ctgtcattgc ggtcttttac tcttctcaat accttattaa    120
aaccctatct cactcactca ctcacaccgt tccatttctc aacaacttct gctacttcct    180
actccaaccg cacttctgct ccgcaattat c                                   211
```

```
<210> SEQ ID NO 7
<211> LENGTH: 34
<212> TYPE: DNA
<213> ORGANISM: Artificial sequence
<220> FEATURE:
<223> OTHER INFORMATION: Primer, PSO467143-F1

<400> SEQUENCE: 7
tacccgggct cgctcctttg tgatttctca ttag                                 34
```

```
<210> SEQ ID NO 8
<211> LENGTH: 30
<212> TYPE: DNA
<213> ORGANISM: Artificial sequence
<220> FEATURE:
<223> OTHER INFORMATION: Primer, PSO467143-R1

<400> SEQUENCE: 8
taccatggat aattgcggag cagaagtgcg                                      30
```

```
<210> SEQ ID NO 9
<211> LENGTH: 23
<212> TYPE: DNA
<213> ORGANISM: Artificial sequence
<220> FEATURE:
<223> OTHER INFORMATION: Primer, QC690-A
```

<400> SEQUENCE: 9
gataattgcg gagcagaagt gcg				23

<210> SEQ ID NO 10
<211> LENGTH: 32
<212> TYPE: DNA
<213> ORGANISM: Artificial sequence
<220> FEATURE:
<223> OTHER INFORMATION: Primer, QC690-S1

<400> SEQUENCE: 10
gattagtaca atctattgca ggaaagtatg tg			32

<210> SEQ ID NO 11
<211> LENGTH: 30
<212> TYPE: DNA
<213> ORGANISM: Artificial sequence
<220> FEATURE:
<223> OTHER INFORMATION: Primer, QC690-S2

<400> SEQUENCE: 11
attctcatcg gttaacaagt atttttcatg			30

<210> SEQ ID NO 12
<211> LENGTH: 33
<212> TYPE: DNA
<213> ORGANISM: Artificial sequence
<220> FEATURE:
<223> OTHER INFORMATION: Primer, QC690-S3

<400> SEQUENCE: 12
agtatgattt tgttatattt gtgcaacact tag			33

<210> SEQ ID NO 13
<211> LENGTH: 35
<212> TYPE: DNA
<213> ORGANISM: Artificial sequence
<220> FEATURE:
<223> OTHER INFORMATION: Primer, QC690-S4

<400> SEQUENCE: 13
aaagctcatc atattttcgt acagtatagt attag			35

<210> SEQ ID NO 14
<211> LENGTH: 24
<212> TYPE: DNA
<213> ORGANISM: Artificial sequence
<220> FEATURE:
<223> OTHER INFORMATION: Primer, QC690-S5

<400> SEQUENCE: 14
caccgtagta gtccttggca aagc				24

<210> SEQ ID NO 15
<211> LENGTH: 1392
<212> TYPE: DNA
<213> ORGANISM: Glycine max

<400> SEQUENCE: 15
ctcactcact cactcacacc gctccatttc tcaacaactt ctgctacttc ctactccaac		60 cgcacttctg ctccgcaatt atcatgggca aggtcaagat cggaatcaac ggatttggaa		120 gaattggccg tttggtagcc agagtggctc tgcagagaga cgatgttgaa ctcgttgccg		180 ttaacgaccc tttcatcacc accgattaca tgacatacat gtttaaatac gacagtgttc		240

```
atggacactg gaagcatcac gatgtcaccg ttaaggacga gaagacccctt ctcttcggtg      300 acaagccagt cactattttt ggacacagaa accctgaaga gatcccatgg gggtcaactg      360
gagctgacat cattgttgag tccaccggag ttttcaccga taaggacaag gccgccgcac      420
atttgaaggg tggtgcaaag aaggttatta tttctgcccc cagtaaggat gcccccatgt      480
ttgttgttgg tgtcaacgag cacgagtaca agccagagct tgatattatt ccaatgcta       540 gctgcacaac caactgcctt gccccacttg ccaaggttat caatgacagg tttggcattg      600
ttgagggttt gatgaccact gttcattcca tcaccgctac ccagaagact gttgatggac      660
catcagccaa ggactggaga ggtggaagag ctgcttcatt taacatcatt cctagcagca      720
ctggagctgc caaggctgtt gggaaagtcc tccctgcttt gaatggaaaa ttgactggta      780
tggcattccg tgttcccacc gtggatgtct ctgttgttga cctcacagtg aggctggaga      840
aagaagcttc ctacgatgaa attaaaaatg ctatcaagga ggaatcagag gcaagttga       900 agggaattct tggttacact gaagatgatg tggtctccac tgactttatc ggcgatagca      960
gatcaagtat ttttgatgca aaggctggaa ttgcattgaa taagaacttt gtgaagcttg     1020
tttcttggta cgacaacgag tggggataca gctcacgtgt cattgatctt cttgtattcg     1080
ttgccaagaa gtctctttaa ggtgttactt caaagtagct tgtcttcaca ttattaccgt     1140
atgtttatgt ttagctgcga tttagtgtct tgctcgagca aaaaatgaga ggtctgaata     1200
aatcggtttc tgaaaccagt ggtgttactt gttggaggag cattagctct tttttggact     1260
tttgatgttt tctcttgtgg aggggatcg agttttttgga ttttttatata ctcgctgatg     1320 tacttggctt gaatacttgc taatgtactt gttattgatt gttatagtag atatttgtcc     1380
gtcctttttt tc                                                         1392
```

<210> SEQ ID NO 16  
<211> LENGTH: 338  
<212> TYPE: PRT  
<213> ORGANISM: Glycine max

<400> SEQUENCE: 16

Met Gly Lys Val Lys Ile Gly Ile Asn Gly Phe Gly Arg Ile Gly Arg  
1               5                   10                  15

Leu Val Ala Arg Val Ala Leu Gln Arg Asp Asp Val Glu Leu Val Ala  
            20                  25                  30

Val Asn Asp Pro Phe Ile Thr Thr Asp Tyr Met Thr Tyr Met Phe Lys  
        35                  40                  45

Tyr Asp Ser Val His Gly Trp Lys His His Asp Val Thr Val Lys  
    50                  55                  60

Asp Glu Lys Thr Leu Leu Phe Gly Asp Lys Pro Val Thr Ile Phe Gly  
65                  70                  75                  80

His Arg Asn Pro Glu Glu Ile Pro Trp Gly Ser Thr Gly Ala Asp Ile  
                85                  90                  95

Ile Val Glu Ser Thr Gly Val Phe Thr Asp Lys Asp Lys Ala Ala Ala  
            100                 105                 110

His Leu Lys Gly Gly Ala Lys Lys Val Ile Ile Ser Ala Pro Ser Lys  
        115                 120                 125

Asp Ala Pro Met Phe Val Val Gly Val Asn Glu His Glu Tyr Lys Pro  
    130                 135                 140

Glu Leu Asp Ile Ile Ser Asn Ala Ser Cys Thr Thr Asn Cys Leu Ala  
145                 150                 155                 160

Pro Leu Ala Lys Val Ile Asn Asp Arg Phe Gly Ile Val Glu Gly Leu
            165                 170                 175

Met Thr Thr Val His Ser Ile Thr Ala Thr Gln Lys Thr Val Asp Gly
        180                 185                 190

Pro Ser Ala Lys Asp Trp Arg Gly Gly Arg Ala Ala Ser Phe Asn Ile
            195                 200                 205

Ile Pro Ser Ser Thr Gly Ala Ala Lys Ala Val Gly Lys Val Leu Pro
        210                 215                 220

Ala Leu Asn Gly Lys Leu Thr Gly Met Ala Phe Arg Val Pro Thr Val
225                 230                 235                 240

Asp Val Ser Val Val Asp Leu Thr Val Arg Leu Glu Lys Glu Ala Ser
                245                 250                 255

Tyr Asp Glu Ile Lys Asn Ala Ile Lys Glu Glu Ser Glu Gly Lys Leu
            260                 265                 270

Lys Gly Ile Leu Gly Tyr Thr Glu Asp Asp Val Val Ser Thr Asp Phe
        275                 280                 285

Ile Gly Asp Ser Arg Ser Ser Ile Phe Asp Ala Lys Ala Gly Ile Ala
    290                 295                 300

Leu Asn Lys Asn Phe Val Lys Leu Val Ser Trp Tyr Asp Asn Glu Trp
305                 310                 315                 320

Gly Tyr Ser Ser Arg Val Ile Asp Leu Leu Val Phe Val Ala Lys Lys
                325                 330                 335

Ser Leu

<210> SEQ ID NO 17
<211> LENGTH: 4812
<212> TYPE: DNA
<213> ORGANISM: Artificial sequence
<220> FEATURE:
<223> OTHER INFORMATION: Plasmid, QC690

<400> SEQUENCE: 17
cccgggctcg ctcctttgtg atttctcatt agaaaataga atctagaaac tataggatag      60
cgttacacac ttacaaaata taagtatttc actcaatttt tgacaagttg ttatttttc     120 ggtaaattat gataatgaca ttttaatttt agtcacgaa tgagttaatg ttaaaaatat     180
aaggaataag aagttagctt ttataatttt atgataatat taataataat aataataata     240 gtgattttt aagatatgaa aaactaaatt tatgttttt ttcccaaata actgctaatt     300
agtatgaata ggataggatt agtacaatct attgcaggaa agtatgtgtt catgttttat     360
tagacaaaaa ttaaacaaaa ttttaaaata aaaacagag gaaatcatgc cttggcttgg     420
taacttacta tcttctggtc cttcatatga taaacaaaca gtgttttttt ccctaatca     480 taagaatcat ataattattt taaatgtat taataactat tttttatat ctttaatttg     540 ttgtgaagtc tttaatgat cactcattat tcatgaaagt atatacagtt aatgaactat     600
taataatata acttattctc atcggttaac aagtattttt catgtattat gagtagtgat     660
attatatgta accacttctt atatccattg attttatgga tatttttaaa ataaaatttg     720
aatttatatt agtattaatt aaaagtaact actttaatca ttttttatttg tcttgattat     780 ttaatcttat ggttttcatt tgtgatgatg atcaaagata gtatgatagt atgattttgt     840
tatatttgtg caacacttag ttatgtttaa taatttttttt taaaaaaata taaatatatt     900
gaaaaggtca tatgcaagcg gtagcctcac ccaagaataa ttaaaataga cccaaattct     960
ctgaataaat agacctaaat actccatgaa tgtgtttcat tgtttgttat ttgatgttca    1020

-continued

```
tcaaatatca aatataatta aagctcatca tattttcgta cagtatagta ttagtattat    1080
atcctgctca ccaaaccaaa catctaagaa taaccttatt tcatttagaa aaaaaaaacc    1140
caagtaaaat tgaaaaaaga atcaaaacaa taaaaagaga gaaaagcgaa tggaatattc    1200
gcatatctgt tggcgtgaaa cagaaaccac aaaaaaaaaa aaaaaaaacg gtacaccgta    1260
gtagtccttg gcaaagcatc acgagtcaca aggcggtccc gtaggagtca cgcacttcac    1320
ttggcccatt tacctgtcat tgcggtcttt tactcttctc aatacctttat taaaaccccta   1380
tctcactcac tcactcacac cgttccattt ctcaacaact tctgctactt cctactccaa    1440
ccgcacttct gctccgcaat tatccatggc ccagtccaag cacggcctga ccaaggagat    1500
gaccatgaag taccgcatgg agggctgcgt ggacggccac aagttcgtga tcaccggcga    1560
gggcatcggc tacccttca agggcaagca ggccatcaac ctgtgcgtgg tggagggcgg    1620
ccccttgccc ttcgccgagg acatcttgtc cgccgccttc atgtacggca accgcgtgtt    1680
caccgagtac ccccaggaca tcgtcgacta cttcaagaac tcctgccccg ccggctacac    1740
ctgggaccgc tccttcctgt tcgaggacgg cgccgtgtgc atctgcaacg ccgacatcac    1800
cgtgagcgtg gaggagaact gcatgtacca cgagtccaag ttctacggcg tgaacttccc    1860
cgccgacggc cccgtgatga agaagatgac cgacaactgg gagccctcct gcgagaagat    1920
catccccgtg cccaagcagg gcatcttgaa gggcgacgtg agcatgtacc tgctgctgaa    1980
ggacggtggc cgcttgcgct gccagttcga caccgtgtac aaggccaagt ccgtgccccg    2040
caagatgccc gactggcact tcatccagca caagctgacc cgcgaggacc gcagcgacgc    2100
caagaaccag aagtgcacc tgaccgagca cgccatcgcc tccggctccg ccttgccctc    2160
cggactcaga tctcgactag agtcgaacct agacttgtcc atcttctgga ttggccaact    2220
taattaatgt atgaaataaa aggatgcaca catagtgaca tgctaatcac tataatgtgg    2280
gcatcaaagt tgtgtgttat gtgtaattac tagttatctg aataaaagag aaagagatca    2340
tccatatttc ttatcctaaa tgaatgtcac gtgtctttat aattctttga tgaaccagat    2400
gcatttcatt aaccaaatcc atatacatat aaatattaat catatataat taatatcaat    2460
tgggttagca aaacaaatct agtctaggtg tgttttgcga attctagtgg ccggcccagc    2520
tgatatccat cacactggcg gccgcactcg actgaattgg ttccggcgcc agcctgcttt    2580
tttgtacaaa gttggcatta taaaaaagca ttgcttatca atttgttgca acgaacaggt    2640
cactatcagt caaaataaaa tcattatttg gggcccgagc ttaagtaact aactaacagg    2700
aagagtttgt agaaacgcaa aaaggccatc cgtcaggatg gccttctgct tagtttgatg    2760
cctggcagtt tatggcgggc gtcctgcccg ccaccctccg ggccgttgct tcacaacgtt    2820
caaatccgct cccggcggat ttgtcctact caggagagcg ttcaccgaca acaacagat    2880
aaaacgaaag gcccagtctt ccgactgagc ctttcgtttt atttgatgcc tggcagttcc    2940
ctactctcgc ttagtagtta gacgtccccg agatccatgc tagcggtaat acggttatcc    3000
acagaatcag gggataacgc aggaaagaac atgtgagcaa aaggccagca aaaggccagg    3060
aaccgtaaaa aggccgcgtt gctggcgttt ttccataggc tccgcccccc tgacgagcat    3120
cacaaaaatc gacgctcaag tcagaggtgg cgaaacccga caggactata aagataccag    3180
gcgtttcccc ctggaagctc cctcgtgcgc tctcctgttc cgaccctgcc gcttaccgga    3240
tacctgtccg cctttctccc ttcgggaagc gtggcgcttt ctcatagctc acgctgtagg    3300
tatctcagtt cggtgtaggt cgttcgctcc aagctgggct gtgtgcacga accccccgtt    3360
cagcccgacc gctgcgcctt atccggtaac tatcgtcttg agtccaaccc ggtaagacac    3420
```

```
gacttatcgc cactggcagc agccactggt aacaggatta gcagagcgag gtatgtaggc    3480
ggtgctacag agttcttgaa gtggtggcct aactacggct acactagaag aacagtattt    3540
ggtatctgcg ctctgctgaa gccagttacc ttcggaaaaa gagttggtag ctcttgatcc    3600
ggcaaacaaa ccaccgctgg tagcggtggt ttttttgttt gcaagcagca gattacgcgc    3660
agaaaaaaag gatctcaaga agatcctttg atcttttcta cggggtctga cgctcagtgg    3720 aacgggccc aatctgaata atgttacaac caattaacca attctgatta gaaaaactca    3780
tcgagcatca aatgaaactg caatttattc atatcaggat tatcaatacc atattttga    3840 aaaagccgtt tctgtaatga aggagaaaac tcaccgaggc agttccatag gatggcaaga    3900
tcctggtatc ggtctgcgat tccgactcgt ccaacatcaa tacaacctat taatttcccc    3960
tcgtcaaaaa taaggttatc aagtgagaaa tcaccatgag tgacgactga atccggtgag    4020
aatggcaaaa gtttatgcat ttctttccag acttgttcaa caggccagcc attacgctcg    4080
tcatcaaaat cactcgcatc aaccaaaccg ttattcattc gtgattgcgc ctgagcgaga    4140
cgaaatacgc gatcgctgtt aaaaggacaa ttacaaacag gaatcgaatg caaccggcgc    4200
aggaacactg ccagcgcatc aacaatattt tcacctgaat caggatattc ttctaatacc    4260
tggaatgctg ttttccggg gatcgcagtg gtgagtaacc atgcatcatc aggagtacgg    4320
ataaaatgct tgatggtcgg aagaggcata aattccgtca gccagtttag tctgaccatc    4380
tcatctgtaa catcattggc aacgctacct ttgccatgtt cagaaacaa ctctggcgca    4440 tcgggcttcc catacaagcg atagattgtc gcacctgatt gcccgacatt atcgcgagcc    4500
catttatacc catataaatc agcatccatg ttggaattta atcgcggcct cgacgtttcc    4560
cgttgaatat ggctcataac accccttgta ttactgttta tgtaagcaga cagttttatt    4620
gttcatgatg atatattttt atcttgtgca atgtaacatc agagattttg agacacgggc    4680
cagagctgca gctggatggc aaataatgat tttattttga ctgatagtga cctgttcgtt    4740
gcaacaaatt gataagcaat gctttcttat aatgccaact ttgtacaaga agctgggtc    4800 tagatatctc ga                                                        4812
```

<210> SEQ ID NO 18
<211> LENGTH: 8482
<212> TYPE: DNA
<213> ORGANISM: Artificial sequence
<220> FEATURE:
<223> OTHER INFORMATION: Plasmid, QC478i

<400> SEQUENCE: 18

```
atcgaaccac tttgtacaag aaagctgaac gagaaacgta aaatgatata aatatcaata     60
tattaaatta gattttgcat aaaaaacaga ctacataata ctgtaaaaca caacatatcc    120
agtcactatg gtcgacctgc agactggctg tgtataaggg agcctgacat ttatattccc    180
cagaacatca ggttaatggc gttttgatg tcatttcgc ggtggctgag atcagccact    240
tcttccccga taacggagac cggcacactg gccatatcgg tggtcatcat cgccagcttt    300
tcatccccga tatgcaccac cgggtaaagt tcacggggga cttatctga cagcagacgt    360 gcactggcca gggggatcac catccgtcgc ccgggcgtgt caataatatc actctgtaca    420
tccacaaaca gacgataacg gctctctctt ttataggtgt aaaccttaaa ctgcatttca    480
ccagcccctg ttctcgtcag caaaagagcc gttcatttca ataaaccggg cgacctcagc    540
catcccttcc tgattttccg ctttccagcg ttcggcacgc agacgacggg cttcattctg    600
```

```
catggttgtg cttaccagac cggagatatt gacatcatat atgccttgag caactgatag    660
ctgtcgctgt caactgtcac tgtaatacgc tgcttcatag catacctctt tttgacatac    720
ttcgggtata catatcagta tatattctta taccgcaaaa atcagcgcgc aaatacgcat    780
actgttatct ggcttttagt aagccggatc ctctagatta cgccccgcct gccactcatc    840
gcagtactgt tgtaattcat taagcattct gccgacatgg aagccatcac aaacggcatg    900
atgaacctga atcgccagcg gcatcagcac cttgtcgcct tgcgtataat atttgcccat    960
ggtgaaaacg ggggcgaaga agttgtccat attggccacg tttaaatcaa aactggtgaa   1020
actcacccag ggattggctg agacgaaaaa catattctca ataaaccctt tagggaaata   1080
ggccaggttt tcaccgtaac acgccacatc ttgcgaatat atgtgtagaa actgccggaa   1140
atcgtcgtgg tattcactcc agagcgatga aaacgtttca gtttgctcat ggaaaacggt   1200
gtaacaaggg tgaacactat cccatatcac cagctcaccg tctttcattg ccatacggaa   1260
ttccggatga gcattcatca ggcgggcaag aatgtgaata aaggccggat aaaacttgtg   1320
cttattttc tttacggtct ttaaaaaggc cgtaatatcc agctgaacgg tctgttata    1380
ggtacattga gcaactgact gaaatgcctc aaaatgttct ttacgatgcc attgggatat   1440
atcaacggtg gtatatccag tgattttttt ctccatttta gcttccttag ctcctgaaaa   1500
tctcgacgga tcctaactca aaatccacac attatacgag ccggaagcat aaagtgtaaa   1560
gcctggggtg cctaatgcgg ccgccatagt gactggatat gttgtgtttt acagtattat   1620
gtagtctgtt ttttatgcaa atctaatttt aatatattga tatttatatc attttacgtt   1680
tctcgttcag cttttttgta caaacttgtt tgataaacac tagtaacggc cgccagtgtg   1740
ctggaattcg ccctttcccaa gctttgctct agatcaaact cacatccaaa cataacatgg   1800
atatcttcct taccaatcat actaattatt ttgggttaaa tattaatcat tattttaag    1860
atattaatta agaaattaaa agatttttta aaaaaatgta taaaattata ttattcatga   1920
tttttcatac atttgatttt gataataaat atattttttt taatttctta aaaaatgttg   1980
caagacactt attagacata gtcttgttct gtttacaaaa gcattcatca tttaatacat   2040
taaaaaatat ttaatactaa cagtagaatc ttcttgtgag tggtgtggga gtaggcaacc   2100
tggcattgaa acgagagaaa gagagtcaga accagaagac aaataaaaag tatgcaacaa   2160
acaaatcaaa atcaaagggc aaaggctggg gttggctcaa ttggttgcta cattcaattt   2220
tcaactcagt caacggttga gattcactct gacttcccca atctaagccg cggatgcaaa   2280
cggttgaatc taacccacaa tccaatctcg ttacttaggg gcttttccgt cattaactca   2340
cccctgccac ccggtttccc tataaattgg aactcaatgc tcccctctaa actcgtatcg   2400
cttcagagtt gagaccaaga cacactcgtt catatatctc tctgctcttc tcttctcttc   2460
tacctctcaa ggtactttc ttctccctct accaaatcct agattccgtg gttcaatttc    2520
ggatcttgca cttctggttt gctttgcctt gcttttcct caactgggtc catctaggat    2580
ccatgtgaaa ctctactctt tctttaatat ctgcggaata cgcgtttgac tttcagatct   2640
agtcgaaatc atttcataat tgcctttctt tctttagct tatgagaaat aaaatcactt     2700
ttttttatt tcaaaataaa ccttgggcct tgtgctgact gagatggggt ttggtgatta   2760
cagaatttta gcgaattttg taattgtact tgtttgtctg tagttttgtt ttgttttctt   2820
gtttctcata cattccttag gcttcaattt tattcgagta taggtcacaa taggaattca   2880
aactttgagc aggggaatta atcccttcct tcaaatccag tttgtttgta tatatgttta   2940
aaaaatgaaa cttttgcttt aaattctatt ataacttttt ttatggctga aattttgca    3000
```

```
tgtgtctttg ctctctgttg taaatttact gtttaggtac taactctagg cttgttgtgc   3060 agttttgaa  gtataacaac agaagttcct attccgaagt tcctattctc tagaaagtat    3120
aggaacttcc accacacaac acaatggcgg ccaccgcttc cagaaccacc cgattctctt    3180
cttcctcttc acaccccacc ttccccaaac gcattactag atccaccctc cctctctctc    3240
atcaaaccct caccaaaccc aaccacgctc tcaaaatcaa atgttccatc tccaaacccc    3300
ccacggcggc gcccttcacc aaggaagcgc cgaccacgga gcccttcgtg tcacggttcg    3360
cctccggcga acctcgcaag ggcgcggaca tccttgtgga ggcgctggag aggcagggcg    3420
tgacgacggt gttcgcgtac cccggcggtg cgtcgatgga gatccaccag gcgctcacgc    3480
gctccgccgc catccgcaac gtgctcccgc gccacgagca gggcggcgtc ttcgccgccg    3540
aaggctacgc gcgttcctcc ggcctccccg gcgtctgcat tgccacctcc ggccccggcg    3600
ccaccaacct cgtgagcggc ctcgccgacg ctttaatgga cagcgtccca gtcgtcgcca    3660
tcaccggcca ggtcgcccgc cggatgatcg gcaccgacgc cttccaagaa acccccgatcg   3720 tggaggtgag cagatccatc acgaagcaca actacctcat cctcgacgtc gacgacatcc    3780
cccgcgtcgt cgccgaggct ttcttcgtcg ccacctccgg ccgccccggt ccggtcctca    3840
tcgacattcc caaagacgtt cagcagcaac tcgccgtgcc taattgggac gagcccgtta    3900
acctccccgg ttacctcgcc aggctgccca ggccccccgc cgaggcccaa ttggaacaca    3960
ttgtcagact catcatggag gcccaaaagc ccgttctcta cgtcggcggt ggcagtttga    4020
attccagtgc tgaattgagg cgctttgttg aactcactgg tattcccgtt gctagcactt    4080
taatgggtct tggaactttt cctattggtg atgaatattc ccttcagatg ctgggtatgc    4140
atggtactgt ttatgctaac tatgctgttg acaatagtga tttgttgctt gcctttgggg    4200
taaggtttga tgaccgtgtt actgggaagc ttgaggcttt tgctagtagg gctaagattg    4260
ttcacattga tattgattct gccgagattg ggaagaacaa gcaggcgcac gtgtcggttt    4320
gcgcggattt gaagttggcc ttgaagggaa ttaatatgat tttggaggag aaaggagtgg    4380
agggtaagtt tgatcttgga ggttggagag aagagattaa tgtgcagaaa cacaagtttc    4440
cattgggtta caagacattc caggacgcga tttctccgca gcatgctatc gaggttcttg    4500
atgagttgac taatgagat  gctattgtta gtactggggt tgggcagcat caaatgtggg    4560
ctgcgcagtt ttacaagtac aagagaccga ggcagtggtt gacctcaggg ggtcttggag    4620
ccatgggttt tggattgcct gcggctattg gtgctgctgt tgctaaccct ggggctgttg    4680
tggttgacat tgatggggat ggtagtttca tcatgaatgt tcaggagttg gccactataa    4740
gagtggagaa tctcccagtt aagatattgt tgttgaacaa tcagcatttg ggtatggtgg    4800
ttcagttgga ggataggttc tacaagtcca atagagctca cacctatctt ggagatccgt    4860
ctagcgagag cgagatattc ccaaacatgc tcaagtttgc tgatgcttgt gggataccgg    4920
cagcgcgagt gacgaagaag gaagagctta gagcggcaat tcagagaatg ttggacaccc    4980
ctggccccta ccttcttgat gtcattgtgc cccatcagga gcatgtgttg ccgatgattc    5040
ccagtaatgg atccttcaag gatgtgataa ctgagggtga tggtagaacg aggtactgat    5100
tgcctagacc aaatgttcct tgatgcttgt tttgtacaat atatataaga taatgctgtc    5160
ctagttgcag gatttggcct gtggtgagca tcatagtctg tagtagtttt ggtagcaaga    5220
cattttattt tccttttatt taacttacta catgcagtag catctatcta tctctgtagt    5280
ctgatatctc ctgttgtctg tattgtgccg ttggattttt tgctgtagtg agactgaaaa    5340
```

```
tgatgtgcta gtaataatat ttctgttaga aatctaagta gagaatctgt tgaagaagtc    5400
aaaagctaat ggaatcaggt tacatattca atgtttttct tttttagcg gttggtagac    5460 gtgtagattc aacttctctt ggagctcacc taggcaatca gtaaaatgca tattccttt    5520 ttaacttgcc atttatttac ttttagtgga aattgtgacc aatttgttca tgtagaacgg    5580
atttggacca ttgcgtccac aaaacgtctc ttttgctcga tcttcacaaa gcgataccga    5640
aatccagaga tagttttcaa aagtcagaaa tggcaaagtt ataaatagta aaacagaata    5700
gatgctgtaa tcgacttcaa taacaagtgg catcacgttt ctagttctag acccatcagc    5760
tgggccggcc cagctgatga tcccggtgaa gttcctattc cgaagttcct attctccaga    5820
aagtatagga acttcactag agcttgcggc cgcgcatgct gacttaatca gctaacgcca    5880
ctcgaggggg ggcccggtac cggcgcgccg ttctatagtg tcacctaaat cgtatgtgta    5940
tgatacataa ggttatgtat taattgtagc cgcgttctaa cgacaatatg tccatatggt    6000
gcactctcag tacaatctgc tctgatgccg catagttaag ccagccccga cacccgccaa    6060
cacccgctga cgcgccctga cgggcttgtc tgctcccggc atccgcttac agacaagctg    6120
tgaccgtctc cgggagctgc atgtgtcaga ggttttcacc gtcatcaccg aaacgcgcga    6180
gacgaaaggg cctcgtgata cgcctatttt tataggttaa tgtcatgacc aaaatccctt    6240
aacgtgagtt ttcgttccac tgagcgtcag accccgtaga aagatcaaa ggatcttctt     6300 gagatccttt ttttctgcgc gtaatctgct gcttgcaaac aaaaaaacca ccgctaccag    6360
cggtggtttg tttgccggat caagagctac caactctttt tccgaaggta actggcttca    6420
gcagagcgca gataccaaat actgtccttc tagtgtagcc gtagttaggc caccacttca    6480
agaactctgt agcaccgcct acatacctcg ctctgctaat cctgttacca gtggctgctg    6540
ccagtggcga taagtcgtgt cttaccgggt tggactcaag acgatagtta ccggataagg    6600
cgcagcggtc gggctgaacg gggggttcgt gcacacagcc cagcttggag cgaacgacct    6660
acaccgaact gagataccta cagcgtgagc attgagaaag cgccacgctt cccgaaggga    6720
gaaaggcgga caggtatccg gtaagcggca gggtcggaac aggagagcgc acgagggagc    6780
ttccaggggg aaacgcctgg tatctttata gtcctgtcgg gtttcgccac ctctgacttg    6840
agcgtcgatt tttgtgatgc tcgtcagggg ggcggagcct atggaaaaac gccagcaacg    6900
cggccttttt acgttcctg gccttttgct ggcttttgc tcacatgttc tttcctgcgt      6960
tatcccctga ttctgtggat aaccgtatta ccgcctttga gtgagctgat accgctcgcc    7020
gcagccgaac gaccgagcgc agcgagtcag tgagcgagga agcggaagag cgcccaatac    7080
gcaaaccgcc tctccccgcg cgttggccga ttcattaatg caggttgatc agatctcgat    7140
cccgcgaaat taatacgact cactataggg agaccacaac ggtttccctc tagaaataat    7200
tttgtttaac tttaagaagg agatatacccc atggaaaagc ctgaactcac cgcgacgtct    7260
gtcgagaagt ttctgatcga aaagttcgac agcgtctccg acctgatgca gctctcggag    7320
ggcgaagaat ctcgtgcttt cagcttcgat gtaggagggc gtggatatgt cctgcgggta    7380
aatagctgcg ccgatggttt ctacaaagat cgttatgttt atcggcactt tgcatcggcc    7440
gcgctcccga ttccggaagt gcttgacatt ggggaattca gcgagagcct gacctattgc    7500
atctcccgcc gtgcacaggg tgtcacgttg caagacctgc ctgaaaccga actgcccgct    7560
gttctgcagc cggtcgcgga ggctatggat gcgatcgctg cggccgatct tagccagacg    7620
agcgggttcg gcccattcgg accgcaagga atcggtcaat acactacatg gcgtgatttc    7680
atatgcgcga ttgctgatcc ccatgtgtat cactggcaaa ctgtgatgga cgacaccgtc    7740
```

```
agtgcgtccg tcgcgcaggc tctcgatgag ctgatgcttt gggccgagga ctgccccgaa    7800
gtccggcacc tcgtgcacgc ggatttcggc tccaacaatg tcctgacgga caatggccgc    7860
ataacagcgg tcattgactg gagcgaggcg atgttcgggg attcccaata cgaggtcgcc    7920
aacatcttct tctggaggcc gtggttggct tgtatggagc agcagacgcg ctacttcgag    7980
cggaggcatc cggagcttgc aggatcgccg cggctccggg cgtatatgct ccgcattggt    8040
cttgaccaac tctatcagag cttggttgac ggcaatttcg atgatgcagc ttgggcgcag    8100
ggtcgatgcg acgcaatcgt ccgatccgga gccgggactg tcgggcgtac acaaatcgcc    8160
cgcagaagcg cggccgtctg gaccgatggc tgtgtagaag tactcgccga tagtggaaac    8220
cgacgcccca gcactcgtcc gagggcaaag gaatagtgag gtacagcttg gatcgatccg    8280
gctgctaaca aagcccgaaa ggaagctgag ttggctgctg ccaccgctga gcaataacta    8340
gcataacccc ttggggcctc taaacgggtc ttgagggggtt ttttgctgaa aggaggaact    8400
atatccggat gctcgggcgc gccggtaccc gggtaccgag ctcactagac gcggtgaaat    8460
tacctaatta acaccggtgt tt                                             8482

<210> SEQ ID NO 19
<211> LENGTH: 9411
<212> TYPE: DNA
<213> ORGANISM: Artificial sequence
<220> FEATURE:
<223> OTHER INFORMATION: Plasmid, QC699

<400> SEQUENCE: 19
cccgggctcg ctcctttgtg atttctcatt agaaaataga atctagaaac tataggatag      60
cgttacacac ttacaaaata taagtatttc actcaattt tgacaagttg ttatttttttc     120 ggtaaattat gataatgaca ttttaatttt agtacatgaa tgagttaatg ttaaaaatat     180
aaggaataag aagttagctt ttataatttt atgataatat taataataat aataataata     240
gtgatttttt aagatatgaa aaactaaatt tatgtttttt ttcccaaata actgctaatt     300
agtatgaata ggataggatt agtacaatct attgcaggaa agtatgtgtt catgttttat     360
tagacaaaaa ttaaacaaaa ttttaaaata aaaacagag gaaatcatgc cttggcttgg     420
taacttacta tcttctggtc cttcatatga taaacaaaca gtgtttttt cccctaatca     480 taagaatcat ataattattt ttaaatgtat taataactat tttttatat ctttaatttg     540 ttgtgaagtc ttttaatgat cactcattat tcatgaaagt atatacagtt aatgaactat     600
taataatata acttattctc atcggttaac aagtattttt catgtattat gagtagtgat     660
attatatgta accacttctt atatccattg attttatgga tatttttaaa ataaaatttg     720
aatttatatt agtattaatt aaaagtaact actttaatca ttttttatttg tcttgattat     780 ttaatcttat ggttttcatt tgtgatgatg atcaaagata gtatgatagt atgattttgt     840
tatatttgtg caacacttag ttatgtttaa taatttttt taaaaaaata taatatatt      900 gaaaaggtca tatgcaagcg gtagcctcac ccaagaataa ttaaaataga cccaaattct     960
ctgaataaat agacctaaat actccatgaa tgtgtttcat tgtttgttat ttgatgttca    1020
tcaaatatca aatataatta aagctcatca tattttcgta cagtatagta ttagtattat    1080
atcctgctca ccaaaccaaa catctaagaa taaccttatt tcatttagaa aaaaaaacc     1140 caagtaaaat tgaaaaaaga atcaaaacaa taaaaagaga gaaaagcgaa tggaatattc    1200
gcatatctgt tggcgtgaaa cagaaaccac aaaaaaaaaa aaaaaaaacg gtacaccgta    1260
```

```
gtagtccttg gcaaagcatc acgagtcaca aggcggtccc gtaggagtca cgcacttcac    1320
ttggcccatt tacctgtcat tgcggtcttt tactcttctc aatacccttat taaaacccta   1380 tctcactcac tcactcacac cgttccattt ctcaacaact tctgctactt cctactccaa    1440
ccgcacttct gctccgcaat tatccatggc ccagtccaag cacggcctga ccaaggagat    1500
gaccatgaag taccgcatgg agggctgcgt ggacggccac aagttcgtga tcaccggcga    1560
gggcatcggc tacccctcca agggcaagca ggccatcaac ctgtgcgtgg tggagggcgg    1620
ccccttgccc ttcgccgagg acatcttgtc cgccgccttc atgtacggca accgcgtgtt    1680
caccgagtac ccccaggaca tcgtcgacta cttcaagaac tcctgccccg ccggctacac    1740
ctgggaccgc tccttcctgt cgaggacgg cgccgtgtgc atctgcaacg ccgacatcac    1800
cgtgagcgtg gaggagaact gcatgtacca cgagtccaag ttctacggcg tgaacttccc    1860
cgccgacggc cccgtgatga agaagatgac cgacaactgg gagccctcct gcgagaagat    1920
catccccgtg cccaagcagg gcatcttgaa gggcgacgtg agcatgtacc tgctgctgaa    1980
ggacggtggc cgcttgcgct gccagttcga caccgtgtac aaggccaagt ccgtgccccg    2040
caagatgccc gactggcact tcatccagca caagctgacc cgcgaggacc gcagcgacgc    2100
caagaaccag aagtggcacc tgaccgagca cgccatcgcc tccggctccg ccttgccctc    2160
cggactcaga tctcgactag agtcgaacct agacttgtcc atcttctgga ttggccaact    2220
taattaatgt atgaaataaa aggatgcaca catagtgaca tgctaatcac tataatgtgg    2280
gcatcaaagt tgtgtgttat gtgtaattac tagttatctg aataaaagag aaagagatca    2340
tccatatttc ttatcctaaa tgaatgtcac gtgtctttat aattctttga tgaaccagat    2400
gcatttcatt aaccaaatcc atatacatat aaatattaat catatataat taatatcaat    2460
tgggttagca aaacaaatct agtctaggtg tgttttgcga attctagtgg ccggcccagc    2520
tgatatccat cacactggcg gccgcactcg actgaattgg ttccggcgcc agcctgcttt    2580
tttgtacaaa cttgtttgat aaacactagt aacggccgcc agtgtgctgg aattcgccct    2640
tcccaagctt tgctctagat caaactcaca tccaaacata acatggatat cttccttacc    2700
aatcatacta attattttgg gttaaatatt aatcattatt tttaagatat taattaagaa    2760
attaaaagat ttttttaaaaa aatgtataaa attatattat tcatgatttt tcatacattt    2820
gattttgata ataaatatat ttttttttaat ttcttaaaaa atgttgcaag acacttatta    2880
gacatagtct tgttctgttt acaaaagcat tcatcattta atacattaaa aaatatttaa    2940
tactaacagt agaatcttct tgtgagtggt gtgggagtag gcaacctggc attgaaacga    3000
gagaaagaga gtcagaacca gaagacaaat aaaaagtatg caacaaacaa atcaaaatca    3060
aagggcaaag gctggggttg gctcaattgg ttgctacatt caattttcaa ctcagtcaac    3120
ggttgagatt cactctgact tccccaatct aagccgcgga tgcaaacggt tgaatctaac    3180
ccacaatcca atctcgttac ttagggggctt ttccgtcatt aactcacccc tgccacccgg    3240
tttccctata aattggaact caatgctccc ctctaaactc gtatcgcttc agagttgaga    3300
ccaagacaca ctcgttcata tatctctctg ctcttctctt ctcttctacc tctcaaggta    3360
cttttcttct ccctctacca aatcctagat tccgtggttc aatttcggat cttgcacttc    3420
tggtttgctt tgccttgctt tttcctcaac tgggtccatc taggatccat gtgaaactct    3480
actctttctt taatatctgc ggaatacgcg tttgactttc agatctagtc gaaatcattt    3540
cataattgcc tttctttctt ttagcttatg agaaataaaa tcactttttt tttatttcaa    3600
aataaacctt gggccttgtg ctgactgaga tgggggtttgg tgattacaga attttagcga    3660
```

```
attttgtaat tgtacttgtt tgtctgtagt tttgttttgt tttcttgttt ctcatacatt   3720
ccttaggctt caattttatt cgagtatagg tcacaatagg aattcaaact ttgagcaggg   3780
gaattaatcc cttccttcaa atccagtttg tttgtatata tgtttaaaaa atgaaacttt   3840
tgctttaaat tctattataa cttttttat ggctgaaatt tttgcatgtg tctttgctct   3900
ctgttgtaaa tttactgttt aggtactaac tctaggcttg ttgtgcagtt tttgaagtat   3960
aacaacagaa gttcctattc cgaagttcct attctctaga aagtatagga acttccacca   4020
cacaacacaa tggcggccac cgcttccaga accacccgat tctcttcttc ctcttcacac   4080
cccacctcc ccaaacgcat tactagatcc accctccctc tctctcatca aaccctcacc   4140
aaacccaacc acgctctcaa atcaaatgt tccatctcca aaccccccac ggcggcgccc   4200
ttcaccaagg aagcgccgac cacggagccc ttcgtgtcac ggttcgcctc cggcgaacct   4260
cgcaagggcg cggacatcct tgtggaggcg ctggagaggc agggcgtgac gacggtgttc   4320
gcgtaccccg gcggtgcgtc gatggagatc caccaggcgc tcacgcgctc cgccgccatc   4380
cgcaacgtgc tcccgcgcca cgagcagggc ggcgtcttcg ccgccgaagg ctacgcgcgt   4440
tcctccggcc tccccggcgt ctgcattgcc acctccggcc ccggcgccac caacctcgtg   4500
agcggcctcg ccgacgcttt aatggacagc gtcccagtcg tcgccatcac cggccaggtc   4560
gcccgccgga tgatcggcac cgacgccttc caagaaaccc cgatcgtgga ggtgagcaga   4620
tccatcacga agcacaacta cctcatcctc gacgtcgacg acatcccccg cgtcgtcgcc   4680
gaggctttct tcgtcgccac ctccggccgc cccggtccgg tcctcatcga cattcccaaa   4740
gacgttcagc agcaactcgc cgtgcctaat tgggacgagc ccgttaacct ccccggttac   4800
ctcgccaggc tgcccaggcc ccccgccgag gcccaattgg aacacattgt cagactcatc   4860
atggaggccc aaaagcccgt tctctacgtc ggcggtggca gtttgaattc cagtgctgaa   4920
ttgaggcgct ttgttgaact cactggtatt cccgttgcta gcactttaat gggtcttgga   4980
acttttccta ttggtgatga atattccctt cagatgctgg gtatgcatgg tactgtttat   5040
gctaactatg ctgttgacaa tagtgatttg ttgcttgcct ttgggtaag gtttgatgac   5100
cgtgttactg ggaagcttga ggcttttgct agtagggcta agattgttca cattgatatt   5160
gattctgccg agattgggaa gaacaagcag gcgcacgtgt cggtttgcgc ggatttgaag   5220
ttggccttga agggaattaa tatgattttg agagagaaag gagtggaggg taagtttgat   5280
cttggaggtt ggagagaaga gattaatgtg cagaaacaca gtttccatt gggttacaag   5340
acattccagg acgcgatttc tccgcagcat gctatcgagg ttcttgatga ttgactaat   5400
ggagatgcta ttgttagtac tggggttggg cagcatcaaa tgtgggctgc gcagttttac   5460
aagtacaaga gaccgaggca gtggttgacc tcaggggtc ttggagccat gggttttgga   5520
ttgcctgcgg ctattggtgc tgctgttgct aaccctgggg ctgttgtggt tgacattgat   5580
ggggatggta gtttcatcat gaatgttcag gagttggcca ctataagagt ggagaatctc   5640
ccagttaaga tattgttgtt gaacaatcag catttgggta tggtggttca gttggaggat   5700
aggttctaca gtccaatag agctcacacc tatcttggag atccgtctag cgagagcgag   5760
atattcccaa acatgctcaa gtttgctgat gcttgtggga taccggcagc gcgagtgacg   5820
aagaaggaag agcttagagc ggcaattcag agaatgttgg acacccctgg cccctacctt   5880
cttgatgtca ttgtgcccca tcaggagcat gtgttgccga tgattcccag taatggatcc   5940
ttcaaggatg tgataactga gggtgatggt agaacgaggt actgattgcc tagaccaaat   6000
```

```
gttccttgat gcttgttttg tacaatatat ataagataat gctgtcctag ttgcaggatt    6060
tggcctgtgg tgagcatcat agtctgtagt agttttggta gcaagacatt ttattttcct    6120
tttatttaac ttactacatg cagtagcatc tatctatctc tgtagtctga tatctcctgt    6180
tgtctgtatt gtgccgttgg atttttgct gtagtgagac tgaaaatgat gtgctagtaa     6240
taatatttct gttagaaatc taagtagaga atctgttgaa gaagtcaaaa gctaatggaa    6300
tcaggttaca tattcaatgt ttttcttttt ttagcggttg gtagacgtgt agattcaact    6360
tctcttggag ctcacctagg caatcagtaa aatgcatatt ccttttttaa cttgccattt    6420
atttactttt agtggaaatt gtgaccaatt tgttcatgta gaacggattt ggaccattgc    6480
gtccacaaaa cgtctctttt gctcgatctt cacaaagcga taccgaaatc cagagatagt    6540
tttcaaaagt cagaaatggc aaagttataa atagtaaaac agaatagatg ctgtaatcga    6600
cttcaataac aagtggcatc acgtttctag ttctagaccc atcagctggg ccggcccagc    6660
tgatgatccc ggtgaagttc ctattccgaa gttcctattc tccagaaagt ataggaactt    6720
cactagagct tgcggccgcg catgctgact taatcagcta acgccactcg agggggggcc    6780
cggtaccggc gcgccgttct atagtgtcac ctaaatcgta tgtgtatgat acataaggtt    6840
atgtattaat tgtagccgcg ttctaacgac aatatgtcca tatggtgcac tctcagtaca    6900
atctgctctg atgccgcata gttaagccag ccccgacacc cgccaacacc cgctgacgcg    6960
ccctgacggg cttgtctgct cccggcatcc gcttacagac aagctgtgac cgtctccggg    7020
agctgcatgt gtcagaggtt ttcaccgtca tcaccgaaac gcgcgagacg aaagggcctc    7080
gtgatacgcc tatttttata ggttaatgtc atgaccaaaa tcccttaacg tgagttttcg    7140
ttccactgag cgtcagaccc cgtagaaaag atcaaaggat cttcttgaga tccttttttt    7200
ctgcgcgtaa tctgctgctt gcaaacaaaa aaaccaccgc taccagcggt ggtttgtttg    7260
ccggatcaag agctaccaac tcttttccg aaggtaactg gcttcagcag agcgcagata     7320
ccaaatactg tccttctagt gtagccgtag ttaggccacc acttcaagaa ctctgtagca    7380
ccgcctacat acctcgctct gctaatcctg ttaccagtgg ctgctgccag tggcgataag    7440
tcgtgtctta ccgggttgga ctcaagacga tagttaccgg ataaggcgca gcggtcgggc    7500
tgaacggggg gttcgtgcac acagcccagc ttggagcgaa cgacctacac cgaactgaga    7560
tacctacagc gtgagcattg agaaagcgcc acgcttcccg aagggagaaa ggcggacagg    7620
tatccggtaa gcggcagggt cggaacagga gagcgcacga gggagcttcc aggggggaaac   7680 gcctggtatc tttatagtcc tgtcgggttt cgccacctct gacttgagcg tcgatttttg    7740
tgatgctcgt cagggggggcg gagcctatgg aaaaacgcca gcaacgcggc ctttttacgg   7800
ttcctggcct tttgctggcc ttttgctcac atgttctttc ctgcgttatc ccctgattct    7860
gtggataacc gtattaccgc ctttgagtga gctgataccg ctcgccgcag ccgaacgacc    7920
gagcgcagcg agtcagtgag cgaggaagcg gaagagcgcc caatacgcaa accgcctctc    7980
cccgcgcgtt ggccgattca ttaatgcagg ttgatcagat ctcgatcccg cgaaattaat    8040
acgactcact atagggagac cacaacggtt tccctctaga ataattttg tttaacttta    8100 agaaggagat atacccatgg aaaagccgat actcaccgcg acgtctgtcg agaagtttct    8160
gatcgaaaag ttcgacagcg tctccgacct gatgcagctc tcggagggcg aagaatctcg    8220
tgctttcagc ttcgatgtag agggcgtgg atatgtcctg cgggtaaata gctgcgccga    8280
tggtttctac aaagatcgtt atgttatcg gcactttgca tcggccgcgc tcccgattcc     8340
ggaagtgctt gacattgggg aattcagcga gagcctgacc tattgcatct cccgccgtgc    8400
```

```
acagggtgtc acgttgcaag acctgcctga aaccgaactg cccgctgttc tgcagccggt    8460
cgcggaggct atggatgcga tcgctgcggc cgatcttagc cagacgagcg ggttcggccc    8520
attcggaccg caaggaatcg gtcaatacac tacatggcgt gatttcatat gcgcgattgc    8580
tgatccccat gtgtatcact ggcaaactgt gatggacgac accgtcagtg cgtccgtcgc    8640
gcaggctctc gatgagctga tgctttgggc cgaggactgc cccgaagtcc ggcacctcgt    8700
gcacgcggat ttcggctcca acaatgtcct gacgacaat ggccgcataa cagcggtcat     8760
tgactggagc gaggcgatgt cggggattc caatacgag gtcgccaaca tcttcttctg      8820
gaggccgtgg ttggcttgta tggagcagca gacgcgctac ttcgagcgga ggcatccgga    8880
gcttgcagga tcgccgcggc tccgggcgta tatgctccgc attggtcttg accaactcta    8940
tcagagcttg gttgacggca atttcgatga tgcagcttgg gcgcagggtc gatgcgacgc    9000
aatcgtccga tccggagccg ggactgtcgg gcgtacacaa atcgcccgca gaagcgcggc    9060
cgtctggacc gatggctgtg tagaagtact cgccgatagt ggaaaccgac gccccagcac    9120
tcgtccgagg gcaaaggaat agtgaggtac agcttggatc gatccggctg ctaacaaagc    9180
ccgaaaggaa gctgagttgg ctgctgccac cgctgagcaa taactagcat aaccccttgg    9240
ggcctctaaa cgggtcttga ggggtttttt gctgaaagga ggaactatat ccggatgctc    9300
gggcgcgccg gtaccgggt accgagctca ctagacgcgg tgaaattacc taattaacac    9360
cggtgtttat cgaaccactt tgtacaagaa agctgggtct agatatctcg a             9411
```

<210> SEQ ID NO 20
<211> LENGTH: 3965
<212> TYPE: DNA
<213> ORGANISM: Artificial sequence
<220> FEATURE:
<223> OTHER INFORMATION: Plasmid, QC690-1

<400> SEQUENCE: 20

```
gattagtaca atctattgca ggaaagtatg tgttcatgtt ttattagaca aaaattaaac      60
aaaattttaa aataaaaaac agaggaaatc atgccttggc ttggtaactt actatcttct     120
ggtccttcat atgataaaca aacagtgttt ttttccccta atcataagaa tcatataatt     180
atttttaaat gtattaataa ctattttttt atatctttaa tttgttgtga agtcttttaa     240
tgatcactca ttattcatga agtatatac agttaatgaa ctattaataa tataacttat      300
tctcatcggt taacaagtat ttttcatgta ttatgagtag tgatattata tgtaaccact     360
tcttatatcc attgatttta tggatatttt taaaataaaa tttgaattta tattagtatt    420
aattaaaagt aactacttta atcatttta tttgtcttga ttatttaatc ttatggtttt     480
catttgtgat gatgatcaaa gatagtatga tagtatgatt ttgttatatt tgtgcaacac     540
ttagttatgt ttaataattt ttttaaaaa aatataaata tattgaaaag gtcatatgca     600
agcggtagcc tcacccaaga ataattaaaa tagacccaaa ttctctgaat aaatagacct     660
aaatactcca tgaatgtgtt tcattgtttg ttatttgatg ttcatcaaat atcaaatata     720
attaaagctc atcatatttt cgtacagtat agtattagta ttatatcctg ctcaccaaac     780
caaacatcta agaataacct tatttcattt agaaaaaaaa aacccaagta aaattgaaaa    840 agaatcaaa acaataaaaa gagagaaaag cgaatggaat attcgcatat ctgttggcgt     900
gaaacagaaa ccacaaaaaa aaaaaaaaaa aacggtacac cgtagtagtc cttggcaaag    960
catcacgagt cacaaggcgg tcccgtagga gtcacgcact tcacttggcc catttacctg   1020
```

-continued

```
tcattgcggt cttttactct tctcaatacc ttattaaaac cctatctcac tcactcactc    1080
acaccgttcc atttctcaac aacttctgct acttcctact ccaaccgcac ttctgctccg    1140
caattatcaa gggcgaattc gacccagctt tcttgtacaa agttggcatt ataaaaaata    1200
attgctcatc aatttgttgc aacgaacagg tcactatcag tcaaaataaa atcattattt    1260
gccatccagc tgatatcccc tatagtgagt cgtattacat ggtcatagct gtttcctggc    1320
agctctggcc cgtgtctcaa atctctgatg ttacattgc acaagataaa atatatcat     1380
catgcctcct ctagaccagc caggacagaa atgcctcgac ttcgctgctg cccaaggttg    1440
ccgggtgacg cacaccgtgg aaacggatga aggcacgaac ccagtggaca taagcctgtt    1500
cggttcgtaa gctgtaatgc aagtagcgta tgcgctcacg caactggtcc agaaccttga    1560
ccgaacgcag cggtggtaac ggcgcagtgg cggttttcat ggcttgttat gactgttttt    1620
ttggggtaca gtctatgcct cgggcatcca agcagcaagc gcgttacgcc gtgggtcgat    1680
gtttgatgtt atggagcagc aacgatgtta cgcagcaggg cagtcgccct aaaacaaagt    1740
taaacatcat gagggaagcg gtgatcgccg aagtatcgac tcaactatca gaggtagttg    1800
gcgtcatcga gcgccatctc gaaccgacgt tgctggccgt acatttgtac ggctccgcag    1860
tggatggcgg cctgaagcca cacagtgata ttgatttgct ggttacggtg accgtaaggc    1920
ttgatgaaac aacgcggcga gctttgatca cgaccttttg gaaacttcg gcttcccctg     1980
gagagagcga gattctccgc gctgtagaag tcaccattgt tgtgcacgac gacatcattc    2040
cgtggcgtta ccagctaagc gcgaactgca atttggagaa tggcagcgc aatgacattc     2100
ttgcaggtat cttcgagcca gccacgatcg acattgatct ggctatcttg ctgacaaaag    2160
caagagaaca tagcgttgcc ttggtaggtc cagcggcgga ggaactcttt gatccggttc    2220
ctgaacagga tctatttgag gcgctaaatg aaaccttaac gctatggaac tcgccgcccg    2280
actgggctgg cgatgagcga aatgtagtgc ttacgttgtc ccgcatttgg tacagcgcag    2340
taaccggcaa aatcgcgccg aaggatgtcg ctgccgactg gcaatggag cgcctgccgg     2400
cccagtatca gcccgtcata cttgaagcta gacaggctta tcttggacaa gaagaagatc    2460
gcttggcctc gcgcgcagat cagttggaag aatttgtcca ctacgtgaaa ggcgagatca    2520
ccaaggtagt cggcaaataa ccctcgagcc acccatgacc aaaatccctt aacgtgagtt    2580
acgcgtcgtt ccactgagcg tcagaccccg tagaaaagat caaaggatct tcttgagatc    2640
cttttttct gcgcgtaatc tgctgcttgc aaacaaaaaa accaccgcta ccagcggtgg     2700
tttgtttgcc ggatcaagag ctaccaactc tttttccgaa ggtaactggc ttcagcagag    2760
cgcagatacc aaatactgtc cttctagtgt agccgtagtt aggccaccac ttcaagaact    2820
ctgtagcacc gcctacatac ctcgctctgc taatcctgtt accagtggct gctgccagtg    2880
gcgataagtc gtgtcttacc gggttggact caagacgata gttaccggat aaggcgcagc    2940
ggtcgggctg aacggggggt tcgtgcacac agcccagctt ggagcgaacg acctacaccg    3000
aactgagata cctacagcgt gagcattgag aaagcgccac gcttcccgaa gggagaaagg    3060
cggacaggta tccggtaagc ggcagggtcg gaacaggaga gcgcacgagg gagcttccag    3120
ggggaaacgc ctggtatctt tatagtcctg tcgggtttcg ccacctctga cttgagcgtc    3180
gattttgtg atgctcgtca gggggcgga gcctatggaa aaacgccagc aacgcggcct      3240
ttttacggtt cctggccttt tgctggcctt tgctcacat gttctttcct gcgttatccc     3300
ctgattctgt ggataaccgt attaccgcct ttgagtgagc tgataccgct cgccgcagcc    3360
gaacgaccga gcgcagcgag tcagtgagcg aggaagcgga agagcgccca atacgcaaac    3420
```

```
cgcctctccc cgcgcgttgg ccgattcatt aatgcagctg gcacgacagg tttcccgact    3480
ggaaagcggg cagtgagcgc aacgcaatta atacgcgtac cgctagccag gaagagtttg    3540
tagaaacgca aaaaggccat ccgtcaggat ggccttctgc ttagtttgat gcctggcagt    3600
ttatggcggg cgtcctgccc gccacccctcc gggccgttgc ttcacaacgt tcaaatccgc    3660
tcccggcgga tttgtcctac tcaggagagc gttcaccgac aaacaacaga taaaacgaaa    3720
ggcccagtct tccgactgag cctttcgttt tatttgatgc ctggcagttc cctactctcg    3780
cgttaacgct agcatggatg tttttcccagt cacgacgttg taaaacgacg gccagtctta    3840
agctcgggcc ccaaataatg atttatttt gactgatagt gacctgttcg ttgcaacaaa    3900
ttgatgagca atgcttttt ataatgccaa ctttgtacaa aaaagcaggc tccgaattcg    3960
ccctt                                                                3965
```

<210> SEQ ID NO 21
<211> LENGTH: 5286
<212> TYPE: DNA
<213> ORGANISM: Artificial sequence
<220> FEATURE:
<223> OTHER INFORMATION: Plasmid, QC330

<400> SEQUENCE: 21

```
atcaacaagt tgtacaaaa aagctgaacg agaaacgtaa aatgatataa atatcaatat      60
attaaattag attttgcata aaaaacagac tacataatac tgtaaaacac aacatatcca     120
gtcatattgg cggccgcatt aggcacccca ggctttacac tttatgcttc cggctcgtat     180
aatgtgtgga ttttgagtta ggatccgtcg agattttcag gagctaagga agctaaaatg     240
gagaaaaaaa tcactggata taccaccgtt gatatatccc aatggcatcg taaagaacat     300
tttgaggcat ttcagtcagt tgctcaatgt acctataacc agaccgttca gctggatatt     360
acggcctttt taaagaccgt aaagaaaaat aagcacaagt tttatccggc ctttattcac     420
attcttgccc gcctgatgaa tgctcatccg gaattccgta tggcaatgaa agacggtgag     480
ctggtgatat gggatagtgt tcacccttgt tacaccgttt tccatgagca aactgaaacg     540
ttttcatcgc tctggagtga ataccacgac gatttccggc agtttctaca catatattcg     600
caagatgtgg cgtgttacgg tgaaaacctg gcctatttcc ctaaagggtt tattgagaat     660
atgtttttcg tctcagccaa tccctgggtg agtttcacca gttttgattt aaacgtggcc     720
aatatggaca acttcttcgc ccccgttttc accatgggca atattatac gcaaggcgac     780 aaggtgctga tgccgctggc gattcaggtt catcatgccg tttgtgatgg cttccatgtc     840
ggcagaatgc ttaatgaatt acaacagtac tgcgatgagt ggcagggcgg ggcgtaaaga     900
tctggatccg gcttactaaa agccagataa cagtatgcgt atttgcgcgc tgatttttgc     960
ggtataagaa tatatactga tatgtatacc cgaagtatgt caaaaagagg tatgctatga    1020
agcagcgtat tacagtgaca gttgacacgc acagctatca gttgctcaag gcatatatga    1080
tgtcaatatc tccggtctgg taagcacaac catgcagaat gaagcccgtc gtctgcgtgc    1140
cgaacgctgg aaagcggaaa atcaggaagg gatggctgag gtcgcccggt ttattgaaat    1200
gaacggctct tttgctgacg agaacagggg ctggtgaaat gcagtttaag gtttacacct    1260
ataaaagaga gagccgttat cgtctgtttg tggatgtaca gagtgatatt attgacacgc    1320
ccgggcgacg gatggtgatc ccctggccag tgcacgtctg ctgtcagat aaagtctccc    1380 gtgaacttta cccggtggtg catatcgggg atgaaagctg gcgcatgatg accaccgata    1440
```

-continued

```
tggccagtgt gccggtctcc gttatcgggg aagaagtggc tgatctcagc caccgcgaaa    1500
atgacatcaa aaacgccatt aacctgatgt tctggggaat ataaatgtca ggctccctta    1560
tacacagcca gtctgcaggt cgaccatagt gactggatat gttgtgtttt acagtattat    1620
gtagtctgtt ttttatgcaa aatctaattt aatatattga tatttatatc attttacgtt    1680
tctcgttcag ctttcttgta caaagtggtt gatgggatcc atgcccaca gcaagcacgg     1740
cctgaaggag gagatgacca tgaagtacca catggagggc tgcgtgaacg ccacaagtt     1800
cgtgatcacc ggcgagggca tcggctaccc cttcaagggc aagcagacca tcaacctgtg    1860
cgtgatcgag ggcggccccc tgcccttcag cgaggacatc ctgagcgccg gcttcaagta    1920
cggcgaccgg atcttcaccg agtaccccca ggacatcgtg actacttca agaacagctg     1980
ccccgccggc tacacctggg gccggagctt cctgttcgag gacggcgccg tgtgcatctg    2040
taacgtggac atcaccgtga gcgtgaagga gaactgcatc taccacaaga gcatcttcaa    2100
cggcgtgaac ttccccgccg acggccccgt gatgaagaag atgaccacca actgggaggc    2160
cagctgcgag aagatcatgc ccgtgcctaa gcagggcatc ctgaagggcg acgtgagcat    2220
gtacctgctg ctgaaggacg gcggccggta ccggtgccag ttcgacaccg tgtacaaggc    2280
caagagcgtg cccagcaaga tgcccgagtg gcacttcatc cagcacaagc tgctgcggga    2340
ggaccggagc gacgccaaga accagaagtg gcagctgacc gagcacgcca tcgccttccc    2400
cagcgccctg gcctgagagc tcgaatttcc ccgatcgttc aaacatttgg caataaagtt    2460
tcttaagatt gaatcctgtt gccggtcttg cgatgattat catataattt ctgttgaatt    2520
acgttaagca tgtaataatt aacatgtaat gcatgacgtt atttatgaga tgggttttta    2580
tgattagagt cccgcaatta tacatttaat acgcgataga aaacaaaata tagcgcgcaa    2640
actaggataa attatcgcgc gcggtgtcat ctatgttact agatcgggaa ttctagtggc    2700
cggcccagct gatatccatc acactggcgg ccgctcgagt tctatagtgt cacctaaatc    2760
gtatgtgtat gatacataag gttatgtatt aattgtagcc gcgttctaac gacaatatgt    2820
ccatatggtg cactctcagt acaatctgct ctgatgccgc atagttaagc cagccccgac    2880
acccgccaac acccgctgac gcgccctgac gggcttgtct gctcccggca tccgcttaca    2940
gacaagctgt gaccgtctcc gggagctgca tgtgtcagag gttttcaccg tcatcaccga    3000
aacgcgcgag acgaaagggc ctcgtgatac gcctattttt ataggttaat gtcatgacca    3060
aaatccctta acgtgagttt tcgttccact gagcgtcaga ccccgtagaa aagatcaaag    3120
gatcttcttg agatcctttt tttctgcgcg taatctgctg cttgcaaaca aaaaaaccac    3180
cgctaccagc ggtggtttgt ttgccggatc aagagctacc aactcttttt ccgaaggtaa    3240
ctggcttcag cagagcgcag ataccaaata ctgtccttct agtgtagccg tagttaggcc    3300
accacttcaa gaactctgta gcaccgccta catacctcgc tctgctaatc ctgttaccag    3360
tggctgctgc cagtggcgat aagtcgtgtc ttaccgggtt ggactcaaga cgatagttac    3420
cggataaggc gcagcggtcg ggctgaacgg ggggttcgtg cacacagccc agcttggagc    3480
gaacgaccta caccgaactg agatacctac agcgtgagca ttgagaaagc gccacgcttc    3540
ccgaaggag aaaggcggac aggtatccgg taagcggcag gtcggaaca ggagagcgca     3600
cgagggagct ccaggggga acgcctggt atctttatag tcctgtcggg tttcgccacc     3660
tctgacttga gcgtcgattt ttgtgatgct cgtcaggggg gcggagccta tggaaaaacg    3720
ccagcaacgc ggccttttta cggttcctgg ccttttgctg ccttttgct cacatgttct    3780
ttcctgcgtt atcccctgat tctgtggata accgtattac cgcctttgag tgagctgata    3840
```

```
ccgctcgccg cagccgaacg accgagcgca gcgagtcagt gagcgaggaa gcggaagagc    3900
gcccaatacg caaaccgcct ctccccgcgc gttggccgat tcattaatgc aggttgatca    3960
gatctcgatc ccgcgaaatt aatacgactc actataggga gaccacaacg gtttccctct    4020
agaaataatt ttgtttaact ttaagaagga gatatacccc tggaaaagcc tgaactcacc    4080
gcgacgtctg tcgagaagtt tctgatcgaa aagttcgaca cgtctccga cctgatgcag     4140 ctctcggagg gcgaagaatc tcgtgctttc agcttcgatg taggagggcg tggatatgtc    4200
ctgcgggtaa atagctgcgc cgatggtttc tacaaagatc gttatgttta tcggcacttt    4260
gcatcggccg cgctcccgat tccggaagtg cttgacattg gggaattcag cgagagcctg    4320
acctattgca tctcccgccg tgcacagggt gtcacgttgc aagacctgcc tgaaaccgaa    4380
ctgcccgctg ttctgcagcc ggtcgcgag gctatggatg cgatcgctgc ggccgatctt     4440
agccagacga gcgggttcgg cccattcgga ccgcaaggaa tcggtcaata cactacatgg    4500
cgtgatttca tatgcgcgat tgctgatccc catgtgtatc actggcaaac tgtgatggac    4560
gacaccgtca gtgcgtccgt cgcgcaggct ctcgatgagc tgatgctttg gccgaggac     4620 tgccccgaag tccggcacct cgtgcacgcg gatttcggct ccaacaatgt cctgacggac    4680
aatggccgca taacagcggt cattgactgg agcgaggcga tgttcgggga ttcccaatac    4740
gaggtcgcca acatcttctt ctggaggccg tggttggctt gtatggagca gcagacgcgc    4800
tacttcgagc ggaggcatcc ggagcttgca ggatcgccgc ggctccgggc gtatatgctc    4860
cgcattggtc ttgaccaact ctatcagagc ttggttgacg gcaatttcga tgatgcagct    4920
tgggcgcagg gtcgatgcga cgcaatcgtc cgatccggag ccgggactgt cgggcgtaca    4980
caaatcgccc gcagaagcgc ggccgtctgg accgatggct gtgtagaagt actcgccgat    5040
agtggaaacc gacgcccag cactcgtccg agggcaaagg aatagtgagg tacagcttgg     5100
atcgatccgg ctgctaacaa agcccgaaag gaagctgagt tggctgctgc caccgctgag    5160
caataactag cataaccct tggggcctct aaacgggtct tgagggtttt tttgctgaaa     5220
ggaggaacta tatccggatg atcgtcgagg cctcacgtgt taacaagctt gcatgcctgc    5280
aggttt                                                              5286
```

<210> SEQ ID NO 22
<211> LENGTH: 4806
<212> TYPE: DNA
<213> ORGANISM: Artificial sequence
<220> FEATURE:
<223> OTHER INFORMATION: Plasmid, QC690-1Y

<400> SEQUENCE: 22

```
gattagtaca atctattgca ggaaagtatg tgttcatgtt ttattagaca aaaattaaac      60
aaaattttaa aataaaaaac agaggaaatc atgccttggc ttggtaactt actatcttct    120
ggtccttcat atgataaaca aacagtgttt ttttccccta atcataagaa tcatataatt    180
atttttaaat gtattaataa ctattttttt atatctttaa tttgttgtga agtcttttaa    240
tgatcactca ttattcatga aagtatatac agttaatgaa ctattaataa tataacttat    300
tctcatcggt taacaagtat ttttcatgta ttatgagtag tgatattata tgtaaccact    360
tcttatatcc attgatttta tggatatttt taaaataaaa tttgaattta tattagtatt    420
aattaaaagt aactacttta atcattttta tttgtcttga ttatttaatc ttatggtttt    480
catttgtgat gatgatcaaa gatagtatga tagtatgatt ttgttatatt tgtgcaacac    540
```

```
ttagttatgt ttaataattt tttttaaaaa aatataaata tattgaaaag gtcatatgca    600
agcggtagcc tcacccaaga ataattaaaa tagacccaaa ttctctgaat aaatagacct    660
aaatactcca tgaatgtgtt tcattgtttg ttatttgatg ttcatcaaat atcaaatata    720
attaaagctc atcatatttt cgtacagtat agtattagta ttatatcctg ctcaccaaac    780
caaacatcta agaataacct tatttcattt agaaaaaaaa aacccaagta aaattgaaaa    840
aagaatcaaa acaataaaaa gagagaaaag cgaatggaat attcgcatat ctgttggcgt    900
gaaacagaaa ccacaaaaaa aaaaaaaaaa aacggtacac cgtagtagtc cttggcaaag    960
catcacgagt cacaaggcgg tcccgtagga gtcacgcact tcacttggcc catttacctg   1020
tcattgcggt cttttactct tctcaatacc ttattaaaac cctatctcac tcactcactc   1080
acaccgttcc atttctcaac aacttctgct acttcctact ccaaccgcac ttctgctccg   1140
caattatcaa gggcgaattc gacccagctt tcttgtacaa agtggttgat gggatccatg   1200
gcccacagca agcacggcct gaaggaggag atgaccatga agtaccacat ggagggctgc   1260
gtgaacggcc acaagttcgt gatcaccggc gagggcatcg gctacccctt caagggcaag   1320
cagaccatca acctgtgcgt gatcgagggc ggccccctgc ccttcagcga ggacatcctg   1380
agcgccggct tcaagtacgg cgaccggatc ttcaccgagt accccagga catcgtggac   1440
tacttcaaga acagctgccc cgccggctac acctggggcc ggagcttcct gttcgaggac   1500
ggcgccgtgt gcatctgtaa cgtggacatc accgtgagcg tgaaggagaa ctgcatctac   1560
cacaagagca tcttcaacgg cgtgaacttc cccgccgacg gccccgtgat gaagaagatg   1620
accaccaact gggaggccag ctgcgagaag atcatgcccg tgcctaagca gggcatcctg   1680
aagggcgacg tgagcatgta cctgctgctg aaggacggcg gccggtaccg gtgccagttc   1740
gacaccgtgt acaaggccaa gagcgtgccc agcaagatgc ccgagtggca cttcatccag   1800
cacaagctgc tgcgggagga ccggagcgac gccaagaacc agaagtggca gctgaccgag   1860
cacgccatcg ccttccccag cgccctggcc tgagagctcg aatttccccg atcgttcaaa   1920
catttggcaa taaagtttct taagattgaa tcctgttgcc ggtcttgcga tgattatcat   1980
ataatttctg ttgaattacg ttaagcatgt aataattaac atgtaatgca tgacgttatt   2040
tatgagatgg gttttatga ttagagtccc gcaattatac atttaatacg cgatagaaaa   2100
caaaatatag cgcgcaaact aggataaatt atcgcgcgcg gtgtcatcta tgttactaga   2160
tcgggaattc tagtggccgg cccagctgat atccatcaca ctggcggccg ctcgagttct   2220
atagtgtcac ctaaatcgta tgtgtatgat acataaggtt atgtattaat tgtagccgcg   2280
ttctaacgac aatatgtcca tatggtgcac tctcagtaca atctgctctg atgccgcata   2340
gttaagccag ccccgacacc cgccaacacc cgctgacgcg ccctgacggg cttgtctgct   2400
cccggcatcc gcttacagac aagctgtgac cgtctccggg agctgcatgt gtcagaggtt   2460
ttcaccgtca tcaccgaaac gcgcgagacg aaagggcctc gtgatacgcc tatttttata   2520
ggttaatgtc atgaccaaaa tcccttaacg tgagttttcg ttccactgag cgtcagaccc   2580
cgtagaaaag atcaaaggat cttcttgaga tcctttttt ctgcgcgtaa tctgctgctt   2640
gcaaacaaaa aaaccaccgc taccagcggt ggtttgtttg ccggatcaag agctaccaac   2700
tctttttccg aaggtaactg gcttcagcag agcgcagata ccaaatactg tccttctagt   2760
gtagccgtag ttaggccacc acttcaagaa ctctgtagca ccgcctacat acctcgctct   2820
gctaatcctg ttaccagtgg ctgctgccag tggcgataag tcgtgtctta ccgggttgga   2880
ctcaagacga tagttaccgg ataaggcgca gcggtcgggc tgaacggggg gttcgtgcac   2940
```

```
acagcccagc ttggagcgaa cgacctacac cgaactgaga tacctacagc gtgagcattg    3000
agaaagcgcc acgcttcccg aagggagaaa ggcggacagg tatccggtaa gcggcagggt    3060
cggaacagga gagcgcacga gggagcttcc aggggaaac gcctggtatc tttatagtcc     3120
tgtcgggttt cgccacctct gacttgagcg tcgattttg tgatgctcgt cagggggcg      3180 gagcctatgg aaaaacgcca gcaacgcggc cttttacgg ttcctggcct tttgctggcc     3240
ttttgctcac atgttctttc ctgcgttatc ccctgattct gtggataacc gtattaccgc    3300
ctttgagtga gctgataccg ctcgccgcag ccgaacgacc gagcgcagcg agtcagtgag    3360
cgaggaagcg gaagagcgcc caatacgcaa accgcctctc cccgcgcgtt ggccgattca    3420
ttaatgcagg ttgatcagat ctcgatcccg cgaaattaat acgactcact atagggagac    3480
cacaacggtt tccctctaga aataattttg tttaacttta agaaggagat atacccatgg    3540
aaaagcctga actcaccgcg acgtctgtcg agaagtttct gatcgaaaag ttcgacagcg    3600
tctccgacct gatgcagctc tcggagggcg aagaatctcg tgctttcagc ttcgatgtag    3660
gagggcgtgg atatgtcctg cgggtaaata gctgcgccga tggtttctac aaagatcgtt    3720
atgtttatcg gcactttgca tcggccgcgc tcccgattcc ggaagtgctt gacattgggg    3780
aattcagcga gagcctgacc tattgcatct cccgccgtgc acagggtgtc acgttgcaag    3840
acctgcctga aaccgaactg cccgctgttc tgcagccggt cgcggaggct atggatgcga    3900
tcgctgcggc cgatcttagc cagacgagcg ggttcggccc attcggaccg caaggaatcg    3960
gtcaatacac tacatggcgt gatttcatat gcgcgattgc tgatccccat gtgtatcact    4020
ggcaaactgt gatggacgac accgtcagtg cgtccgtcgc gcaggctctc gatgagctga    4080
tgctttgggc cgaggactgc cccgaagtcc ggcacctcgt gcacgcggat ttcggctcca    4140
acaatgtcct gacggacaat ggccgcataa cagcggtcat tgactggagc gaggcgatgt    4200
tcggggattc ccaatacgag gtcgccaaca tcttcttctg gaggccgtgg ttggcttgta    4260
tggagcagca gacgcgctac ttcgagcgga ggcatccgga gcttgcagga tcgccgcggc    4320
tccgggcgta tatgctccgc attggtcttg accaactcta tcagagcttg gttgacggca    4380
atttcgatga tgcagcttgg gcgcagggtc gatgcgacga atcgtccga tccggagccg      4440 ggactgtcgg gcgtacacaa atcgcccgca gaagcgcggc cgtctggacc gatggctgtg    4500
tagaagtact cgccgatagt ggaaaccgac gccccagcac tcgtccgagg gcaaaggaat    4560
agtgaggtac agcttggatc gatccggctg ctaacaaagc ccgaaaggaa gctgagttgg    4620
ctgctgccac cgctgagcaa taactagcat aaccccttgg ggcctctaaa cgggtcttga    4680 ggggttttt gctgaaagga ggaactatat ccggatgatc gtcgaggcct cacgtgttaa     4740
caagcttgca tgcctgcagg tttatcaaca agtttgtaca aaaaagcagg ctccgaattc    4800
gcccctt                                                              4806
```

<210> SEQ ID NO 23
<211> LENGTH: 22
<212> TYPE: DNA
<213> ORGANISM: Artificial sequence
<220> FEATURE:
<223> OTHER INFORMATION: SAMS forward primer SAMS-76F

<400> SEQUENCE: 23
aggcttgttg tgcagttttt ga        22

<210> SEQ ID NO 24

```
<211> LENGTH: 22
<212> TYPE: DNA
<213> ORGANISM: Artificial sequence
<220> FEATURE:
<223> OTHER INFORMATION: FAM labeled ALS probe ALS-100T

<400> SEQUENCE: 24
ccacacaaca caatggcggc ca                                            22

<210> SEQ ID NO 25
<211> LENGTH: 22
<212> TYPE: DNA
<213> ORGANISM: Artificial sequence
<220> FEATURE:
<223> OTHER INFORMATION: ALS reverse primer ALS-163R

<400> SEQUENCE: 25
ggaagaagag aatcgggtgg tt                                            22

<210> SEQ ID NO 26
<211> LENGTH: 24
<212> TYPE: DNA
<213> ORGANISM: Artificial sequence
<220> FEATURE:
<223> OTHER INFORMATION: GFP forward primer GFP-24F

<400> SEQUENCE: 26
gaccaaggag atgaccatga agta                                          24

<210> SEQ ID NO 27
<211> LENGTH: 14
<212> TYPE: DNA
<213> ORGANISM: Artificial sequence
<220> FEATURE:
<223> OTHER INFORMATION: FAM labeled GFP probe GFP-51T

<400> SEQUENCE: 27
catggagggc tgcg                                                     14

<210> SEQ ID NO 28
<211> LENGTH: 20
<212> TYPE: DNA
<213> ORGANISM: Artificial sequence
<220> FEATURE:
<223> OTHER INFORMATION: GFP reverse primer GFP-92R

<400> SEQUENCE: 28
ccggtgatca cgaacttgtg                                               20

<210> SEQ ID NO 29
<211> LENGTH: 24
<212> TYPE: DNA
<213> ORGANISM: Artificial sequence
<220> FEATURE:
<223> OTHER INFORMATION: HSP forward primer HSP-F1

<400> SEQUENCE: 29
caaacttgac aaagccacaa ctct                                          24

<210> SEQ ID NO 30
<211> LENGTH: 20
<212> TYPE: DNA
<213> ORGANISM: Artificial sequence
<220> FEATURE:
<223> OTHER INFORMATION: VIC labeled HSP probe HSP probe

<400> SEQUENCE: 30
```

```
ctctcatctc atataaatac                                                20
```

<210> SEQ ID NO 31
<211> LENGTH: 21
<212> TYPE: DNA
<213> ORGANISM: Artificial sequence
<220> FEATURE:
<223> OTHER INFORMATION: HSP reverse primer HSP-R1

<400> SEQUENCE: 31

```
ggagaaattg gtgtcgtgga a                                              21
```

<210> SEQ ID NO 32
<211> LENGTH: 100
<212> TYPE: DNA
<213> ORGANISM: Artificial sequence
<220> FEATURE:
<223> OTHER INFORMATION: ATTL1

<400> SEQUENCE: 32

```
caaataatga ttttattttg actgatagtg acctgttcgt tgcaacaaat tgataagcaa    60 tgcttttta taatgccaac tttgtacaaa aaagcaggct                           100
```

<210> SEQ ID NO 33
<211> LENGTH: 100
<212> TYPE: DNA
<213> ORGANISM: Artificial sequence
<220> FEATURE:
<223> OTHER INFORMATION: ATTL2

<400> SEQUENCE: 33

```
caaataatga ttttattttg actgatagtg acctgttcgt tgcaacaaat tgataagcaa    60 tgcttttctta taatgccaac tttgtacaag aaagctgggt                         100
```

<210> SEQ ID NO 34
<211> LENGTH: 125
<212> TYPE: DNA
<213> ORGANISM: Artificial sequence
<220> FEATURE:
<223> OTHER INFORMATION: ATTR1

<400> SEQUENCE: 34

```
acaagtttgt acaaaaaagc tgaacgagaa acgtaaaatg atataaatat caatatatta    60
aattagattt tgcataaaaa acagactaca taatactgta aaacacaaca tatccagtca    120
ctatg                                                                125
```

<210> SEQ ID NO 35
<211> LENGTH: 125
<212> TYPE: DNA
<213> ORGANISM: Artificial sequence
<220> FEATURE:
<223> OTHER INFORMATION: ATTR2

<400> SEQUENCE: 35

```
accactttgt acaagaaagc tgaacgagaa acgtaaaatg atataaatat caatatatta    60
aattagattt tgcataaaaa acagactaca taatactgta aaacacaaca tatccagtca    120
ctatg                                                                125
```

<210> SEQ ID NO 36
<211> LENGTH: 21
<212> TYPE: DNA

```
<213> ORGANISM: Artificial sequence
<220> FEATURE:
<223> OTHER INFORMATION: ATTB1

<400> SEQUENCE: 36
caagtttgta caaaaaagca g                                              21

<210> SEQ ID NO 37
<211> LENGTH: 21
<212> TYPE: DNA
<213> ORGANISM: Artificial sequence
<220> FEATURE:
<223> OTHER INFORMATION: ATTB2

<400> SEQUENCE: 37
ccactttgta caagaaagct g                                              21

<210> SEQ ID NO 38
<211> LENGTH: 1489
<212> TYPE: DNA
<213> ORGANISM: Glycine max

<400> SEQUENCE: 38
ggttccattt ctcaacaact tctgctactt cctactccaa ccgcacttct gttccgcaat     60
tatcatgggc aaggtcaaga tcggaatcaa cggatttgga agaattggcc gtttggtagc    120
cagagtggct ctgcagagag acgatgttga actcgttgcc gttaacgacc ctttcatcac    180
caccgattac atgacataca tgtttaaata cgacagtgtt catggacact ggaagcatca    240
cgatgtcacc gttaaggacg agaagaccct tctcttcggt gacaagccag tcactatttt    300
tggacacaga aaccctgaag agatcccatg ggggtcaact ggagctgaca tcattgttga    360
gtccaccgga gttttcaccg ataaggacaa ggccgccgca catttgaagg gtggtgcaaa    420
gaaggttatt atttctgccc ccagtaagga tgcccccatg tttgttgttg gtgtcaacga    480
gcacgagtac aagccagagc ttgatattat ttccaatgct agctgcacaa ccaactgcct    540
tgccccactt gccaaggtta tcaatgacag gtttggcatt gttgagggtt tgatgaccac    600
tgttcattcc atcaccgcta cccagaagac tgttgatgga ccatcagcca aggactggag    660
aggtggaaga gctgcttcat taacatcat  tcctagcagc actggagctg ccaaggctgt    720
tgggaaagtc ctccctgctt tgaatggaaa attgactggt atggcattcc gtgttcccac    780
cgtggatgtc tctgttgttg acctcacagt gaggctggag aaagaagctt cctacgatga    840
aattaaaaat gctatcaagg aggaatcaga gggcaagttg aagggaattc ttggttacac    900
tgaagatgat gtggtctcca ctgactttat cggcgatagc agatcaagta ttttgatgc     960
aaaggctgga attgcattga ataagaactt tgtgaagctt gtttcttggt acgacaacga   1020
gtggggatac agctcacgtg tcattgatct tcttgtattc gttgccaaga agtctcttta   1080
aggtgttact tcaaagtagc ttgtcttcac attattaccg tatgtttatg tttagctgcg   1140
atttagtgtc ttgctcgagc aaaaaatgag aggtctgaat aaatcggttt ctgaaaccag   1200
tggtgttact tgttggagga gcattagctc tttttttggac ttttgatgtt ttctcttgtg   1260
gagggggatc gagttttttgg attttttatat actcgctgat gtacttggct tgaatacttg   1320
ctaatgtact tgttattgat tgttatagta gatatttgtc cgtccttttt ttcatttgtg   1380
gttctcgtat atttgatcct gtttgctttg aatcatggat tcgtggttta aacattttc    1440
tgtgcttatt ttagtccgta tttaaattaa catttttggc ttttagttc                1489
```

```
<210> SEQ ID NO 39
<211> LENGTH: 1471
<212> TYPE: DNA
<213> ORGANISM: Glycine max

<400> SEQUENCE: 39
atcctcctcg ctcctttgtg atttctcatt agaaaataga atctagaaac tataggatag      60
cgttacacac ttacaaaata taagtatttc actcaatttt tgacaagttg ttatttttc      120
ggtaaattat gataatgaca ttttaatttt agtacatgaa tgagttaatg ttaaaaatat     180
aaggaataag aagttagctt ttataatttt atgataatat taataataat aataataata    240
gtgatttttt aagatatgaa aaactaaatt tatgtttttt ttcccaaata actgctaatt    300
agtatgaata ggataggatt agtacaatct attgcaggaa agtatgtgtt catgttttat    360
tagacaaaaa ttaaacaaaa ttttaaaata aaaacagag gaaatcatgc cttggcttgg     420
taacttacta tcttctggtc cttcatatga taaacaaaca gtgttttttt cccctaatca    480
taagaatcat ataattattt ttaaatgtat taataactat tttttatat ctttaatttg     540
ttgtgaagtc ttttaatgat cactcattat tcatgaaagt atatacagtt aatgaactat    600
taataatata acttattctc atcggttaac aagtattttt catgtattat gagtagtgat    660
attatatgta accacttctt atatccattg attttatgga tatttttaaa ataaaatttg   720
aatttatatt agtattaatt aaaagtaact actttaatca ttttttattg tcttgattat    780
ttaatcttat ggttttcatt tgtgatgatg atcaaagata gtatgatagt atgattttgt    840
tatatttgtg caacacttag ttatgtttaa taatttttt taaaaaaata taaatatatt     900
gaaaaggtca tatgcaagcg gtagcctcac ccaagaataa ttaaaataga cccaaattct    960
ctgaataaat agacctaaat actccatgaa tgtgtttcat tgtttgttat ttgatgttca   1020
tcaaatatca aatataatta aagctcatca tattctcgta cagtatagta ttagtattat    1080
atcctgctca ctaaaccaaa catctaagaa taaccttatt tcatttagaa aaaaaaaaac    1140
ccaagtaaaa ttgaaaaaag aatcaaaaca ataaaaagag agaaaagcga atggaatatt    1200
cgcatatctg ttggcgtgaa acagaaacca caaaaaaaaa aaaaaaaaaa acggtacagc    1260
gtagtagtcc ttggcaaagc atcacgagtc acaaggcggt cccgtaggag tcacgcactt    1320
cacttggccc atttacctgt cattgcggtc ttttactctt ctcaataccct tattaaaacc   1380
ctatctcact cactcactca caccgttcca tttctcaaca acttctgcta cttcctactc    1440
caaccgcact tctgctccgc aattatcatg g                                   1471

<210> SEQ ID NO 40
<211> LENGTH: 83
<212> TYPE: DNA
<213> ORGANISM: Glycine max

<400> SEQUENCE: 40
ctcactcact cactcacacc gctccatttc tcaacaactt ctgctacttc ctactccaac      60
cgcacttctg ctccgcaatt atc                                             83
```

SOYBEAN GAPD PROMOTER AND ITS USE IN CONSTITUTIVE EXPRESSION OF TRANSGENIC GENES IN PLANTS

This application claims the benefit of U.S. Provisional Application No. 61/955,256, filed Mar. 19, 2014, and herein incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named 20150304_BB2233USPNP_ST25_SeqLst.txt created on Mar. 4, 2015, and having a size of 69 kilobytes and is filed concurrently with the specification. The sequence listing contained in this ASCII formatted document is part of the specification and is herein incorporated by reference in its entirety.

FIELD OF THE INVENTION

This invention relates to a plant promoter GM-GAPD and fragments thereof and their use in altering expression of at least one heterologous nucleotide sequence in plants in a tissue-independent or constitutive manner.

BACKGROUND OF THE INVENTION

Recent advances in plant genetic engineering have opened new doors to engineer plants to have improved characteristics or traits, such as plant disease resistance, insect resistance, herbicidal resistance, yield improvement, improvement of the nutritional quality of the edible portions of the plant, and enhanced stability or shelf-life of the ultimate consumer product obtained from the plants. Thus, a desired gene (or genes) with the molecular function to impart different or improved characteristics or qualities, can be incorporated properly into the plant's genome. The newly integrated gene (or genes) coding sequence can then be expressed in the plant cell to exhibit the desired new trait or characteristics. It is important that appropriate regulatory signals must be present in proper configurations in order to obtain the expression of the newly inserted gene coding sequence in the plant cell. These regulatory signals typically include a promoter region, a 5' non-translated leader sequence and a 3' transcription termination/polyadenylation sequence.

A promoter is a non-coding genomic DNA sequence, usually upstream (5') to the relevant coding sequence, to which RNA polymerase binds before initiating transcription. This binding aligns the RNA polymerase so that transcription will initiate at a specific transcription initiation site. The nucleotide sequence of the promoter determines the nature of the RNA polymerase binding and other related protein factors that attach to the RNA polymerase and/or promoter, and the rate of RNA synthesis. The RNA is processed to produce messenger RNA (mRNA) which serves as a template for translation of the RNA sequence into the amino acid sequence of the encoded polypeptide. The 5' non-translated leader sequence is a region of the mRNA upstream of the coding region that may play a role in initiation and translation of the mRNA. The 3' transcription termination/polyadenylation signal is a non-translated region downstream of the coding region that functions in the plant cell to cause termination of the RNA synthesis and the addition of polyadenylate nucleotides to the 3' end.

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters" if the promoters direct RNA synthesis preferably in certain tissues but also in other tissues at reduced levels. Since patterns of expression of a chimeric gene (or genes) introduced into a plant are controlled using promoters, there is an ongoing interest in the isolation of novel promoters which are capable of controlling the expression of a chimeric gene or (genes) at certain levels in specific tissue types or at specific plant developmental stages.

Certain promoters are able to direct RNA synthesis at relatively similar levels across all tissues of a plant. These are called "constitutive promoters" or "tissue-independent" promoters. Constitutive promoters can be divided into strong, moderate and weak according to their effectiveness to direct RNA synthesis. Since it is necessary in many cases to simultaneously express a chimeric gene (or genes) in different tissues of a plant to get the desired functions of the gene (or genes), constitutive promoters are especially useful in this consideration. Though many constitutive promoters have been discovered from plants and plant viruses and characterized, there is still an ongoing interest in the isolation of more novel constitutive promoters which are capable of controlling the expression of a chimeric gene or (genes) at different levels and the expression of multiple genes in the same transgenic plant for gene stacking.

SUMMARY OF THE INVENTION

This invention concerns a recombinant DNA construct comprising at least one heterologous nucleotide sequence operably linked to a promoter wherein said promoter comprises the nucleotide sequence set forth in SEQ ID NOs: 1, 2, 3, 4, 5, 6, or 39, or said promoter comprises a functional fragment of the nucleotide sequence set forth in SEQ ID NOs: 1, 2, 3, 4, 5, 6, or 39, or wherein said promoter comprises a nucleotide sequence having at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity, based on the Clustal V method of alignment with pairwise alignment default parameters (KTUPLE=2, GAP PENALTY=5, WINDOW=4 and DIAGONALS SAVED=4), when compared to the nucleotide sequence of SEQ ID NO:1, 2, 3, 4, 5, 6, or 39.

In another embodiment, this invention concerns a recombinant DNA construct comprising a nucleotide sequence comprising any of the sequences set forth in SEQ ID NO:1, SEQ ID NO:2, SEQ ID NO:3, SEQ ID NO:4, SEQ ID NO:5, SEQ ID NO:6, or SEQ ID NO:39, or a functional fragment thereof, operably linked to at least one heterologous sequence, wherein said nucleotide sequence is a constitutive promoter.

In another embodiment, this invention concerns a recombinant DNA construct comprising a nucleotide sequence having at least 95% identity, based on the Clustal V method of alignment with pairwise alignment default parameters (KTUPLE=2, GAP PENALTY=5, WINDOW=4 and DIAGONALS SAVED=4), when compared to the sequence set forth in SEQ ID NO:6.

In another embodiment, this invention concerns a recombinant DNA construct comprising at least one heterologous nucleotide sequence operably linked to a promoter region of a *Glycine max* eukaryotic glyceraldehyde-3-phosphate dehydrogenase (GM-GAPD) gene as set forth in SEQ ID NO:1, wherein said promoter comprises a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 100 6, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 11311, 1132, 1133, 1134, 1135, 1136, 1137, 1138, 1139, 1140, 1141, 1142, 1143, 1144, 1145, 1146, 1147, 1148, 1149, 1150, 11511, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 12312, 1233, 1234, 1235, 1236, 1237, 1238, 1239, 1240, 1241, 1242, 1243, 1244, 1245, 1246, 1247, 1248, 1249, 1250, 1251, 1252, or 1253 consecutive nucleotides, wherein the first nucleotide deleted is the cytosine nucleotide [C] at position 1 of SEQ ID NO:1. This invention also concerns a recombinant DNA construct of the embodiments disclosed herein, wherein the promoter is a constitutive promoter.

In another embodiment, this invention concerns a recombinant DNA construct comprising at least one heterologous nucleotide sequence operably linked to the promoter of the invention.

In another embodiment, this invention concerns a cell, plant, or seed comprising a recombinant DNA construct of the present disclosure.

In another embodiment, this invention concerns plants comprising this recombinant DNA construct and seeds obtained from such plants.

In another embodiment, this invention concerns a method of altering (increasing or decreasing) expression of at least one heterologous nucleic acid fragment in a plant cell which comprises:

(a) transforming a plant cell with the recombinant DNA construct described above;
(b) growing fertile mature plants from the transformed plant cell of step (a);
(c) selecting plants containing the transformed plant cell wherein the expression of the heterologous nucleic acid fragment is increased or decreased.

In another embodiment, this invention concerns a method for expressing a yellow fluorescent protein ZS-GREEN1 (GFP) in a host cell comprising:
(a) transforming a host cell with a recombinant expression construct of the disclosure comprising at least one ZS-GREEN1 nucleic acid fragment operably linked to a promoter wherein said promoter consists essentially of the nucleotide sequence set forth in SEQ ID NOs:1, 2, 3, 4, 5, 6 or 39; and
(b) growing the transformed host cell under conditions that are suitable for expression of the recombinant DNA construct, wherein expression of the recombinant DNA construct results in production of increased levels of ZS-GREEN1 protein in the transformed host cell when compared to a corresponding nontransformed host cell.

In another embodiment, this invention concerns a recombinant DNA construct comprising a plant eukaryotic glyceraldehyde-3-phosphate dehydrogenase (GAPD) gene promoter.

In another embodiment, this invention concerns a method of altering a marketable plant trait. The marketable plant trait concerns genes and proteins involved in disease resistance, herbicide resistance, insect resistance, carbohydrate metabolism, fatty acid metabolism, amino acid metabolism, plant development, plant growth regulation, yield improvement, drought resistance, cold resistance, heat resistance, and salt resistance.

In another embodiment, this invention concerns a recombinant DNA construct linked to a heterologous nucleotide sequence. The heterologous nucleotide sequence encodes a protein involved in disease resistance, herbicide resistance, insect resistance; carbohydrate metabolism, fatty acid metabolism, amino acid metabolism, plant development, plant growth regulation, yield improvement, drought resistance, cold resistance, heat resistance, or salt resistance in plants.

BRIEF DESCRIPTION OF THE DRAWINGS AND SEQUENCE LISTINGS

The invention can be more fully understood from the following detailed description and the accompanying drawings and Sequence Listing that form a part of this application.

FIG. 1 is the relative expression of the soybean eukaryotic glyceraldehyde-3-phosphate dehydrogenase (GAPD) gene (PSO467143, Glyma06g18110.1) in twenty one soybean tissues by Illumina (Solexa) digital gene expression dual-tag-based mRNA profiling. The gene expression profile indicates that the GAPD gene is expressed similarly in all the checked tissues. Black bars show the expression mean (in PPTM) and grey bars show the expression standard deviation (STDV).

FIG. 3A-3D shows the maps of plasmids pCR2.1-TOPO (FIG. 3A), QC690 (FIG. 3B), QC478i (FIG. 3C), and QC699 (FIG. 3D). The 6897 bp AscI-AscI fragment of QC699 is used to produce transgenic soybean plants.

FIG. 4A-4D shows the maps of plasmids pCR8/GW/TOPO (FIG. 4A), QC690-1 (FIG. 4B), QC330 (FIG. 4C), and QC690-1Y (FIG. 4D) containing a full length 1469 bp GAPD promoter. Other promoter deletion constructs QC690-2Y, QC690-3Y, QC690-4Y, and QC690-5Y containing the 1148, 850, 637, 425, and 211 bp truncated GAPD promoters, respectively, have the same map configuration, except for the truncat)ed promoter sequences.

Figure 5:
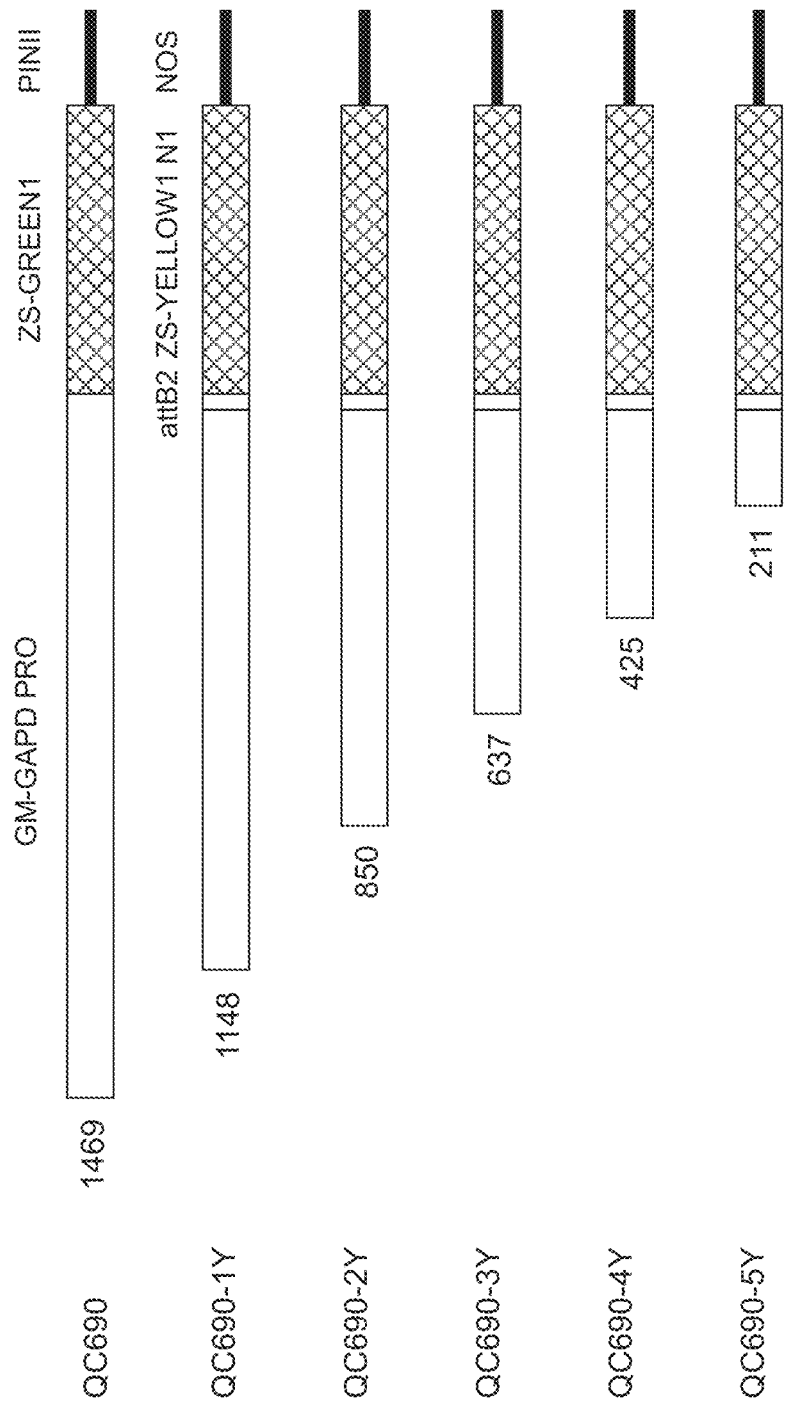

FIG. 5 is the schematic descriptions of the full length 1469 bp GAPD promoter in construct QC690 and its progressive truncations in constructs, QC690-1Y, QC690-2Y, QC690-3Y, QC690-4Y, and QC690-5Y of the GAPD promoter. The size of each promoter is given at the left end of each drawing. QC690-1Y has 1148 bp of the 1469 bp GAPD promoter in QC690 with the XmaI and NcoI sites removed and like the other deletion constructs with the attB site between the promoter and ZS-YELLOW N1 reporter gene.

FIG. 6A-FIG. 6H is the transient expression of the fluorescent protein reporter gene ZS-GREEN1 or ZS-YELLOW1 N1 in the cotyledons of germinating soybean seeds (shown as white dots in a black background). The reporter gene is driven by the full length GAPD promoter in QC690 (FIG. 6C) (with ZS-GREEN1) or by progressively truncated GAPD promoters in the transient expression constructs QC690-1Y to QC690-5Y (with ZS-YELLOW1 N1) (FIG. 6D, FIG. 6E, FIG. 6F, FIG. 6G and FIG. 6 H, respectively).

Figure 7I:
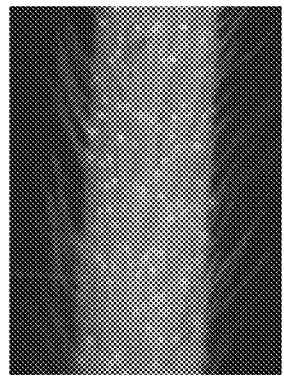
Figure 7J:
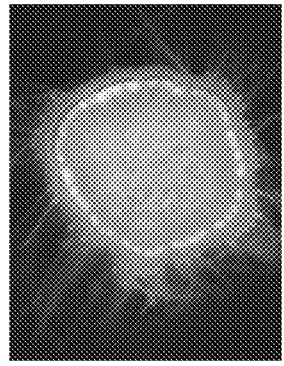
Figure 7K:
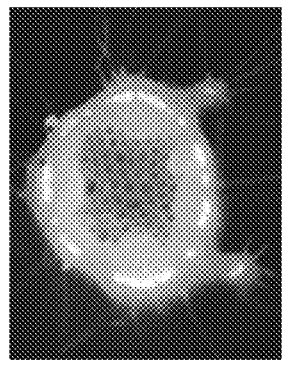
Figure 7L:
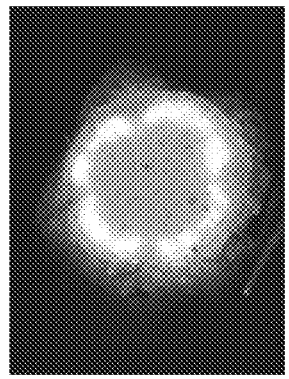
Figure 7M:
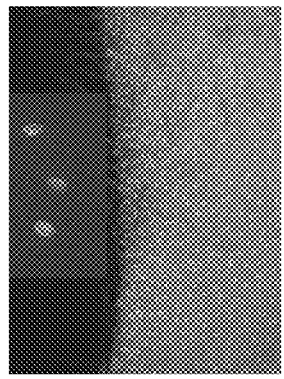
Figure 7N:
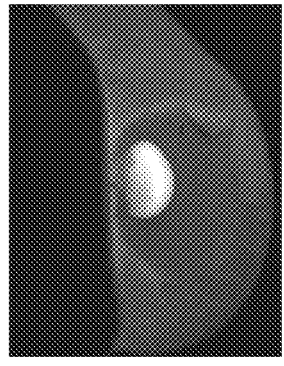
Figure 7O:
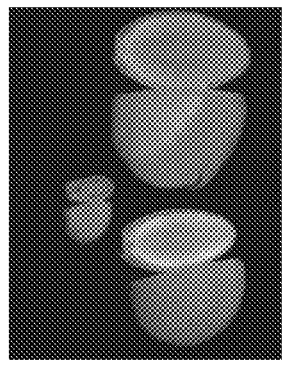
Figure 7P:
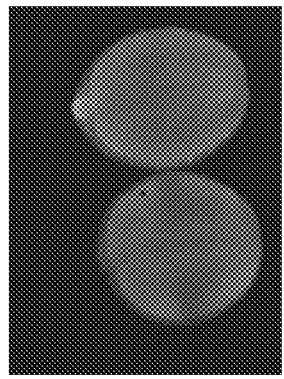

FIG. 7A-7P shows the stable expression of the fluorescent protein reporter gene ZS-GREEN1 (shown as white) in different tissues of transgenic soybean plants containing a single copy of GAPD:GFP DNA of construct QC699, comprising the full length GAPD promoter of SEQ ID NO:1. (FIG. 7A: Embryonic callus, FIG. 7B: Young somatic embryos, FIG. 7C: Cotyledon somatic embryos, FIG. 7D: Open flower, FIG. 7E: A part of a sepal showing stomata, FIG. 7F: Stamen, filaments, anthers, and style of a young flower, FIG. 7G: A part of a pistil showing stomata, FIG. 7H: Leaf showing stomata on adaxial and abaxial sides, FIG. 7I: Stem showing stomata, FIG. 7J: Stem, cross section showing vascular bundles, FIG. 7K: Petiole, cross section showing vascular bundles, FIG. 7L: Root, cross section showing vascular bundles, FIG. 7M: pod surface showing stomata with a close-up showing guard cells, FIG. 7N: Open pod with a R3 seed, FIG. 7O: Developing R3, R4, and R5 seeds, cross sections showing embryos and inner surface of seed coat, FIG. 7P: Cross section of a R6 seed showing embryos and seed coat).

Figure 8:
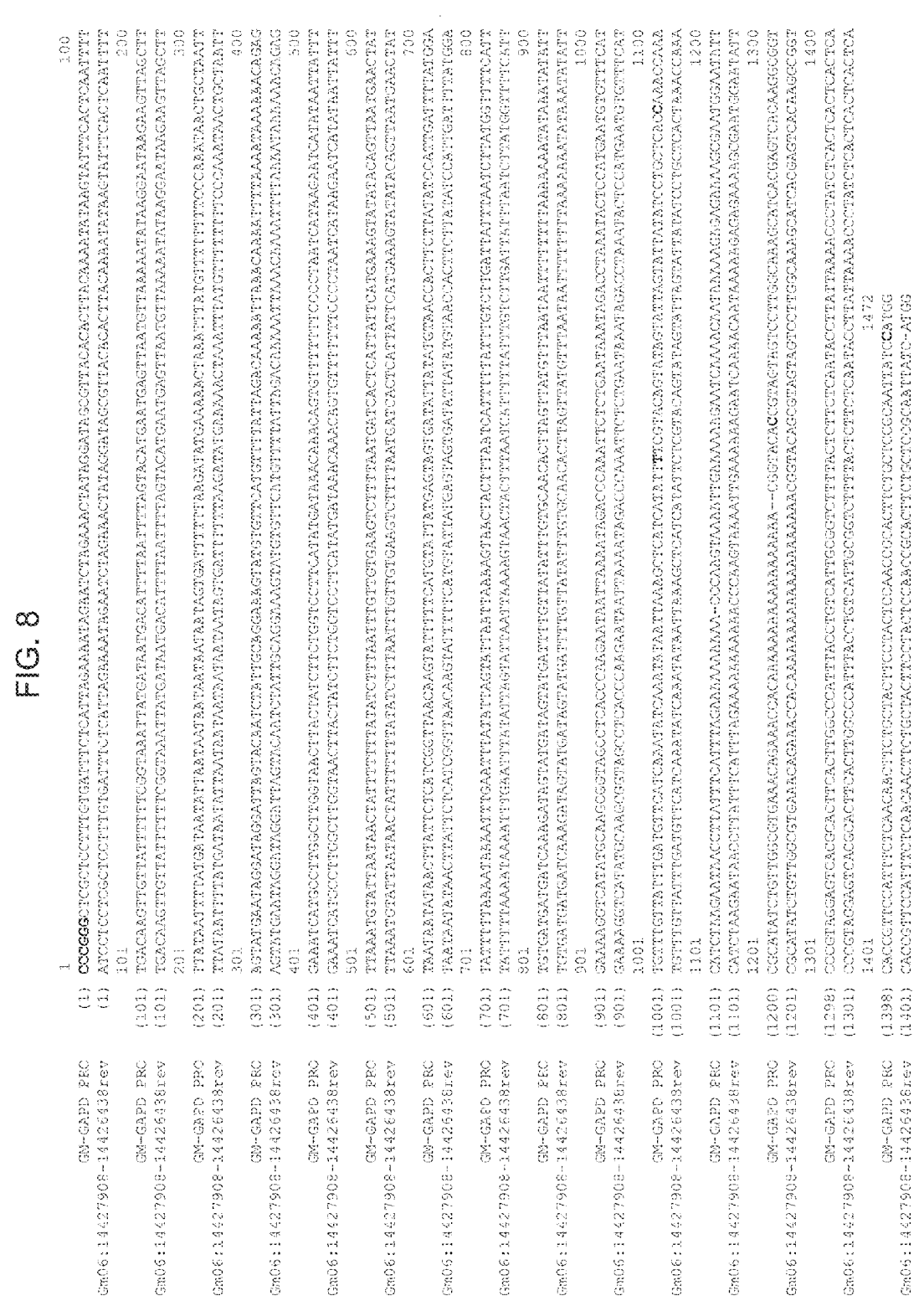

FIG. 8 shows a nucleotide alignment of SEQ ID NO:1 (listed as GM-GAPD PRO in the figure), comprising the GAPD promoter of the disclosure, and SEQ ID NO:39 (listed as Gm06:14427908-14426438rev in the figure), comprising a 1471 bp native soybean genomic DNA from Gm06:14427908-14426438 (rev) (Schmutz J. et al., Genome sequence of the palaeopolyploid soybean, Nature 463:178-183, 2010). The percent sequence identity between the GAPD promoter of SEQ ID NO:1 and the corresponding native soybean genomic DNA of SEQ ID NO:39, based on the Clustal V method of alignment with pairwise alignment default parameters (KTUPLE=2, GAP PENALTY=5, WINDOW=4 and DIAGONALS SAVED=4) is 99.2%.

The sequence descriptions summarize the Sequence Listing attached hereto. The Sequence Listing contains one letter codes for nucleotide sequence characters and the single and three letter codes for amino acids as defined in the IUPAC- IUB standards described in *Nucleic Acids Research* 13:3021-3030 (1985) and in the *Biochemical Journal* 219 (2):345-373 (1984).

SEQ ID NO:1 is the DNA sequence comprising a 1469 bp (base pair) soybean GAPD promoter flanked by XmaI (cccggg) and NcoI (ccatgg) restriction sites.

SEQ ID NO:2 is a 1148 bp truncated form of the GAPD promoter shown in SEQ ID NO:1 (bp 317-1464 of SEQ ID NO:1).

SEQ ID NO:3 is a 850 bp truncated form of the GAPD promoter shown in SEQ ID NO:1 (bp 615-1464 of SEQ ID NO:1).

SEQ ID NO:4 is a 637 bp truncated form of the GAPD promoter shown in SEQ ID NO:1 (bp 828-1464 of SEQ ID NO:1).

SEQ ID NO:5 is a 425 bp truncated form of the GAPD promoter shown in SEQ ID NO:1 (bp 1040-1464 of SEQ ID NO:1).

SEQ ID NO:6 is a 211 bp truncated form of the GAPD promoter shown in SEQ ID NO:1 (bp 1254-1464 of SEQ ID NO:1).

SEQ ID NO:7 is an oligonucleotide primer used as a gene-specific sense primer in the PCR amplification of the full length GAPD promoter in SEQ ID NO:1 when paired with SEQ ID NO:8. A restriction enzyme XmaI recognition site CCCGGG is included for subsequent cloning.

SEQ ID NO:8 is an oligonucleotide primer used as a gene-specific antisense primer in the PCR amplification of the full length GAPD promoter in SEQ ID NO:1 when paired with SEQ ID NO:7. A restriction enzyme NcoI recognition site CCATGG is included for subsequent cloning.

SEQ ID NO:9 is an oligonucleotide primer used as an antisense primer in the PCR amplifications of the truncated GAPD promoters in SEQ ID NOs:2, 3, 4, 5, or 6 when paired with SEQ ID NOs: 10, 11, 12, 13, or 14, respectively.

SEQ ID NO:10 is an oligonucleotide primer used as a sense primer in the PCR amplification of the full length GAPD promoter in SEQ ID NO:2 when paired with SEQ ID NO:9.

SEQ ID NO:11 is an oligonucleotide primer used as a sense primer in the PCR amplification of the truncated GAPD promoter in SEQ ID NO:3 when paired with SEQ ID NO:9.

SEQ ID NO:12 is an oligonucleotide primer used as a sense primer in the PCR amplification of the truncated GAPD promoter in SEQ ID NO:4 when paired with SEQ ID NO:9.

SEQ ID NO:13 is an oligonucleotide primer used as a sense primer in the PCR amplification of the truncated GAPD promoter in SEQ ID NO:5 when paired with SEQ ID NO:9.

SEQ ID NO:14 is an oligonucleotide primer used as a sense primer in the PCR amplification of the truncated GAPD promoter in SEQ ID NO:6 when paired with SEQ ID NO:9.

SEQ ID NO:15 is the 1392 bp nucleotide sequence of the putative soybean eukaryotic glyceraldehyde-3-phosphate dehydrogenase GAPD cDNA (PSO467143).

SEQ ID NO:16 is the predicted 338 aa (amino acid) long peptide sequence translated from the coding region of the putative soybean eukaryotic glyceraldehyde-3-phosphate dehydrogenase GAPD nucleotide sequence SEQ ID NO:15.

SEQ ID NO:17 is the 4812 bp sequence of plasmid QC690.

SEQ ID NO:18 is the 8482 bp sequence of plasmid QC478i.

SEQ ID NO:19 is the 9411 bp sequence of plasmid QC699.

SEQ ID NO:20 is the 3965 bp sequence of plasmid QC690-1.

SEQ ID NO:21 is the 5286 bp sequence of plasmid QC330.

SEQ ID NO:22 is the 4806 bp sequence of plasmid QC690-1Y.

SEQ ID NO:23 is a sense primer used in quantitative PCR analysis of SAMS:HRA transgene copy numbers.

SEQ ID NO:24 is a FAM labeled fluorescent DNA oligo probe used in quantitative PCR analysis of SAMS:HRA transgene copy numbers.

SEQ ID NO:25 is an antisense primer used in quantitative PCR analysis of SAMS:HRA transgene copy numbers.

SEQ ID NO:26 is a sense primer used in quantitative PCR analysis of GM-GAPD:GFP transgene copy numbers.

SEQ ID NO:27 is a FAM labeled fluorescent DNA oligo probe used in quantitative PCR analysis of GM-GAPD:GFP transgene copy numbers.

SEQ ID NO:28 is an antisense primer used in quantitative PCR analysis of GM-GAPD:GFP transgene copy numbers.

SEQ ID NO:29 is a sense primer used as an endogenous control gene primer in quantitative PCR analysis of transgene copy numbers.

SEQ ID NO:30 is a VIC labeled DNA oligo probe used as an endogenous control gene probe in quantitative PCR analysis of transgene copy numbers.

SEQ ID NO:31 is an antisense primer used as an endogenous control gene primer in quantitative PCR analysis of transgene copy numbers.

SEQ ID NO:32 is the recombination site attL1 sequence in the GATEWAY® cloning system (Invitrogen, Carlsbad, Calif.).

SEQ ID NO:33 is the recombination site attL2 sequence in the GATEWAY® cloning system (Invitrogen).

SEQ ID NO:34 is the recombination site attR1 sequence in the GATEWAY® cloning system (Invitrogen).

SEQ ID NO:35 is the recombination site attR2 sequence in the GATEWAY® cloning system (Invitrogen).

SEQ ID NO:36 is the recombination site attB1 sequence in the GATEWAY® cloning system (Invitrogen).

SEQ ID NO:37 is the recombination site attB2 sequence in the GATEWAY® cloning system (Invitrogen).

SEQ ID NO:38 is the 1489 bp nucleotide sequence of a *Glycine max* glyceraldehyde-3-phosphate dehydrogenase (GAPC1) mRNA mRNA DQ355800 similar to the 1392 bp eukaryotic glyceraldehyde-3-phosphate dehydrogenase GAPD gene (PSO467143) sequence SEQ ID NO:15.

SEQ ID NO:39 is a 1471 bp fragment of native soybean genomic DNA Gm06:14427908-14426438 (rev) from cultivar "Williams82" (Schmutz J. et al. Nature 463:178-183, 2010).

SEQ ID NO:40 is a 83 bp fragment of the 5' untranslated region of the GAPD gene included in the GAPD promoter.

DETAILED DESCRIPTION OF THE INVENTION

The disclosure of all patents, patent applications, and publications cited herein are incorporated by reference in their entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

In the context of this disclosure, a number of terms shall be utilized.

An "isolated polynucleotide" refers to a polymer of ribonucleotides (RNA) or deoxyribonucleotides (DNA) that is single- or double-stranded, optionally containing synthetic, non-natural or altered nucleotide bases. An isolated polynucleotide in the form of DNA may be comprised of one or more segments of cDNA, genomic DNA or synthetic DNA.

The terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "soybean GAPD promoter", "GM-GAPD promoter" or "GAPD promoter" are used interchangeably herein, and refer to the promoter of a putative *Glycine max* gene with significant homology to eukaryotic glyceraldehyde-3-phosphate dehydrogenasegenes identified in various plant species including soybean that are deposited in National Center for Biotechnology Information (NCBI) database. The term "soybean GAPD promoter" encompasses both a native soybean promoter and an engineered sequence comprising a fragment of the native soybean promoter with a DNA linker attached to facilitate cloning. A DNA linker may comprise a restriction enzyme site.

"Promoter" refers to a nucleic acid fragment capable of controlling transcription of another nucleic acid fragment. A promoter is capable of controlling the expression of a coding sequence or functional RNA. Functional RNA includes, but is not limited to, transfer RNA (tRNA) and ribosomal RNA (rRNA). The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. New promoters of various types useful in plant cells are constantly being discovered; numerous examples may be found in the compilation by Okamuro and Goldberg (Biochemistry of Plants 15:1-82 (1989)). It is further recognized that since in most cases the exact boundaries of regulatory sequences have not been completely defined, DNA fragments of some variation may have identical promoter activity.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

"Constitutive promoter" refers to promoters active in all or most tissues or cell types of a plant at all or most developing stages. As with other promoters classified as "constitutive" (e.g. ubiquitin), some variation in absolute levels of expression can exist among different tissues or stages. The term "constitutive promoter" or "tissue-independent" are used interchangeably herein.

The promoter nucleotide sequences and methods disclosed herein are useful in regulating constitutive expression of any heterologous nucleotide sequences in a host plant in order to alter the phenotype of a plant.

A "heterologous nucleotide sequence" refers to a sequence that is not naturally occurring with the plant promoter sequence of the disclosure. While this nucleotide sequence is heterologous to the promoter sequence, it may be homologous, or native, or heterologous, or foreign, to the plant host. However, it is recognized that the instant promoters may be used with their native coding sequences to increase or decrease expression resulting in a change in phenotype in the transformed seed. The terms "heterologous nucleotide sequence", "heterologous sequence", "heterologous nucleic acid fragment", and "heterologous nucleic acid sequence" are used interchangeably herein.

Among the most commonly used promoters are the nopaline synthase (NOS) promoter (Ebert et al., Proc. Natl. Acad. Sci. U.S.A. 84:5745-5749 (1987)), the octapine synthase (OCS) promoter, caulimovirus promoters such as the cauliflower mosaic virus (CaMV) 19S promoter (Lawton et al., Plant Mol. Biol. 9:315-324 (1987)), the CaMV 35S promoter (Odell et al., Nature 313:810-812 (1985)), and the figwort mosaic virus 35S promoter (Sanger et al., Plant Mol. Biol. 14:433-43 (1990)), the light inducible promoter from the small subunit of rubisco, the Adh promoter (Walker et al., Proc. Natl. Acad. Sci. U.S.A. 84:6624-66280 (1987), the sucrose synthase promoter (Yang et al., Proc. Natl. Acad. Sci. U.S.A. 87:4144-4148 (1990)), the R gene complex promoter (Chandler et al., Plant Cell 1:1175-1183 (1989)), the chlorophyll a/b binding protein gene promoter, etc. Other commonly used promoters are, the promoters for the potato tuber ADPGPP genes, the sucrose synthase promoter, the granule bound starch synthase promoter, the glutelin gene promoter, the maize waxy promoter, Brittle gene promoter, and Shrunken 2 promoter, the acid chitinase gene promoter, and the zein gene promoters (15 kD, 16 kD, 19 kD, 22 kD, and 27 kD; Perdersen et al., Cell 29:1015-1026 (1982)). A plethora of promoters is described in PCT Publication No. WO 00/18963 published on Apr. 6, 2000, the disclosure of which is hereby incorporated by reference.

The present disclosure encompasses recombinant DNA constructs comprising functional fragments of the promoter sequences disclosed herein.

A "functional fragment" refer to a portion or subsequence of the promoter sequence of the present disclosure in which the ability to initiate transcription or drive gene expression (such as to produce a certain phenotype) is retained. Fragments can be obtained via methods such as site-directed mutagenesis and synthetic construction. As with the provided promoter sequences described herein, the functional fragments operate to promote the expression of an operably linked heterologous nucleotide sequence, forming a recombinant DNA construct (also, a chimeric gene). For example, the fragment can be used in the design of recombinant DNA constructs to produce the desired phenotype in a transformed plant. Recombinant DNA constructs can be designed for use in co-suppression or antisense by linking a promoter fragment in the appropriate orientation relative to a heterologous nucleotide sequence.

A nucleic acid fragment that is functionally equivalent to the promoter of the present disclosure is any nucleic acid fragment that is capable of controlling the expression of a coding sequence or functional RNA in a similar manner to the promoter of the present disclosure.

In an embodiment of the present invention, the promoters disclosed herein can be modified. Those skilled in the art can create promoters that have variations in the polynucleotide sequence. The polynucleotide sequence of the promoters of the present disclosure as shown in SEQ ID NOs: 1, 2, 3, 4, 5, 6, 7, and 41, may be modified or altered to enhance their control characteristics. As one of ordinary skill in the art will appreciate, modification or alteration of the promoter sequence can also be made without substantially affecting the promoter function. The methods are well known to those of skill in the art. Sequences can be modified, for example by insertion, deletion, or replacement of template sequences in a PCR-based DNA modification approach.

A "variant promoter", as used herein, is the sequence of the promoter or the sequence of a functional fragment of a promoter containing changes in which one or more nucleotides of the original sequence is deleted, added, and/or substituted, while substantially maintaining promoter function. One or more base pairs can be inserted, deleted, or substituted internally to a promoter. In the case of a promoter fragment, variant promoters can include changes affecting the transcription of a minimal promoter to which it is operably linked. Variant promoters can be produced, for example, by standard DNA mutagenesis techniques or by chemically synthesizing the variant promoter or a portion thereof.

Methods for construction of chimeric and variant promoters of the present disclosure include, but are not limited to, combining control elements of different promoters or duplicating portions or regions of a promoter (see for example, U.S. Pat. No. 4,990,607; U.S. Pat. No. 5,110,732; and U.S. Pat. No. 5,097,025). Those of skill in the art are familiar with the standard resource materials that describe specific conditions and procedures for the construction, manipulation, and isolation of macromolecules (e.g., polynucleotide molecules and plasmids), as well as the generation of recombinant organisms and the screening and isolation of polynucleotide molecules.

In some aspects of the present disclosure, the promoter fragments can comprise at least about 20 contiguous nucleotides, or at least about 50 contiguous nucleotides, or at least about 75 contiguous nucleotides, or at least about 100 contiguous nucleotides, or at least about 150 contiguous nucleotides, or at least about 200 contiguous nucleotides of SEQ ID NO:1, SEQ ID NO:2, SEQ ID NO:3, SEQ ID NO:4, SEQ ID NO:5, SEQ ID NO:6, or SEQ ID NO:39. In another aspect of the present disclosure, the promoter fragments can comprise at least about 250 contiguous nucleotides, or at least about 300 contiguous nucleotides, or at least about 350 contiguous nucleotides, or at least about 400 contiguous nucleotides, or at least about 450 contiguous nucleotides, or at least about 500 contiguous nucleotides, or at least about 550 contiguous nucleotides, or at least about 600 contiguous nucleotides, or at least about 650 contiguous nucleotides, or at least about 700 contiguous nucleotides, or at least about 750 contiguous nucleotides, or at least about 800 contiguous nucleotides, or at least about 850 contiguous nucleotides, or at least about 900 contiguous nucleotides, or at least about 950 contiguous nucleotides, or at least about 1000 contiguous nucleotides, or at least about 1050 contiguous nucleotides, or at least about 1100 contiguous nucleotides, or at least about 1150 contiguous nucleotides, or at least about 1200 contiguous nucleotides, or at least about 1250 contiguous nucleotides, of SEQ ID NO:1. In another aspect, a promoter fragment is the nucleotide sequence set forth in SEQ ID NO:2, SEQ ID NO:3, SEQ ID NO:4, SEQ ID NO:5, SEQ ID NO:6, or SEQ ID NO:39. The nucleotides of such fragments will usually comprise the TATA recognition sequence of the particular promoter sequence. Such fragments may be obtained by use of restriction enzymes to cleave the naturally occurring promoter nucleotide sequences disclosed herein, by synthesizing a nucleotide sequence from the naturally occurring promoter DNA sequence, or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989.

The terms "full complement" and "full-length complement" are used interchangeably herein, and refer to a complement of a given nucleotide sequence, wherein the complement and the nucleotide sequence consist of the same number of nucleotides and are 100% complementary.

The terms "substantially similar" and "corresponding substantially" as used herein refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences.

The isolated promoter sequence comprised in the recombinant DNA construct of the present disclosure can be modified to provide a range of constitutive expression levels of the heterologous nucleotide sequence. Thus, less than the entire promoter regions may be utilized and the ability to drive expression of the coding sequence retained. However, it is recognized that expression levels of the mRNA may be decreased with deletions of portions of the promoter sequences. Likewise, the tissue-independent, constitutive nature of expression may be changed.

Modifications of the isolated promoter sequences of the present disclosure can provide for a range of constitutive expression of the heterologous nucleotide sequence. Thus, they may be modified to be weak constitutive promoters or strong constitutive promoters. Generally, by "weak promoter" is intended a promoter that drives expression of a coding sequence at a low level. By "low level" is intended at levels about $1/10,000$ transcripts to about $1/100,000$ transcripts to about $1/500,000$ transcripts. Conversely, a strong promoter drives expression of a coding sequence at high level, or at about $1/10$ transcripts to about $1/100$ transcripts to about $1/1,000$ transcripts.

Moreover, the skilled artisan recognizes that substantially similar nucleic acid sequences encompassed by this disclosure are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the disclosure. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U.K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2×SSC, 0.5% SDS was increased to 60° C. Another set of highly stringent conditions uses two final washes in 0.1×SSC, 0.1% SDS at 65° C.

Preferred substantially similar nucleic acid sequences encompassed by this disclosure are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. It is well understood by one skilled in the art that many levels of sequence identity are useful in identifying related polynucleotide sequences. Useful examples of percent identities are those listed above, or also preferred is any integer percentage from 71% to 100%, such as 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%.

In one embodiment, the isolated promoter sequence comprised in the recombinant DNA construct of the present invention concerns an isolated polynucleotide comprising a promoter wherein said promoter comprises a nucleotide sequence having at least 71%. 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity, based on the Clustal V method of alignment with pairwise alignment default parameters (KTUPLE=2, GAP PENALTY=5, WINDOW=4 and DIAGONALS SAVED=4), when compared to the nucleotide sequence of SEQ ID NO:1. As described in Example 2, comparison of SEQ ID NO:1 to a soybean cDNA library revealed that SEQ ID NOs:1, 2, 3, 4, 5, 6, and 39 comprise a 5' untranslated region (5'UTR) of at least 89 base pairs (SEQ ID NO:40). It is known to one of skilled in the art that a 5' UTR region can be altered (deletion or substitutions of bases) or replaced by an alternative 5'UTR while maintaining promoter activity.

This 5' UTR region represents (83/1469)*100=5.7% of SEQ ID NO:1, (83/1148)*100=7.2% of SEQ ID NO:2, (83/850)*100=9.8% of SEQ ID NO:3, (83/637)*100=13.0% of SEQ ID NO:4, (83/425)*100=19.5% of SEQ ID NO:5, and (83/211)*100=39.3% of SEQ ID NO:6, respectively, indicating that an isolated polynucleotide of 94.3% sequence identity to SEQ ID NO:1, or 92.8% sequence identity to SEQ ID NO:2, or 91.2% sequence identity to SEQ ID NO:3, or 87.0% sequence identity to SEQ ID NO:4, or 80.5% sequence identity to SEQ ID NO:5, or 60.7% sequence identity to SEQ ID NO:6 can be generated while maintaining promoter activity.

A "substantially homologous sequence" refers to variants of the disclosed sequences such as those that result from site-directed mutagenesis, as well as synthetically derived sequences. A substantially homologous sequence of the present disclosure also refers to those fragments of a particular promoter nucleotide sequence disclosed herein that operate to promote the constitutive expression of an operably linked heterologous nucleic acid fragment. These promoter fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989. Again, variants of these promoter fragments, such as those resulting from site-directed mutagenesis, are encompassed by the compositions of the present disclosure.

"Codon degeneracy" refers to divergence in the genetic code permitting variation of the nucleotide sequence without affecting the amino acid sequence of an encoded polypeptide. Accordingly, the instant disclosure relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) CABIOS. 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WIN- DOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, CABIOS. 5:151-153 (1989); Higgins, D. G. et al., Comput. Appl. Biosci. 8:189-191 (1992)) can be found in the MegAlign™ v6.1 program of the LASER-GENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

In one embodiment the % sequence identity is determined over the entire length of the molecule (nucleotide or amino acid).

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., J. Mol. Biol. 215:403-410 (1993)) and Gapped Blast (Altschul, S. F. et al., Nucleic Acids Res. 25:3389-3402 (1997)). BLASTN refers to a BLAST program that compares a nucleotide query sequence against a nucleotide sequence database.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., Molecular Biotechnology 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., Plant Cell 1:671-680 (1989).

"RNA transcript" refers to a product resulting from RNA polymerase-catalyzed transcription of a DNA sequence. When an RNA transcript is a perfect complementary copy of a DNA sequence, it is referred to as a primary transcript or it may be a RNA sequence derived from posttranscriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded by using the Klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcripts accumulation of a target gene (U.S. Pat. No. 5,107,065). The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The terms "initiate transcription", "initiate expression", "drive transcription", and "drive expression" are used interchangeably herein and all refer to the primary function of a promoter. As detailed throughout this disclosure, a promoter is a non-coding genomic DNA sequence, usually upstream (5') to the relevant coding sequence, and its primary function is to act as a binding site for RNA polymerase and initiate transcription by the RNA polymerase. Additionally, there is "expression" of RNA, including functional RNA, or the expression of polypeptide for operably linked encoding nucleotide sequences, as the transcribed RNA ultimately is translated into the corresponding polypeptide.

The term "expression", as used herein, refers to the production of a functional end-product e.g., an mRNA or a protein (precursor or mature).

The term "expression cassette" as used herein, refers to a discrete nucleic acid fragment into which a nucleic acid sequence or fragment can be moved.

Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at posttranscriptional level.

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al., Plant J. 16:651-659 (1998); and Gura, Nature 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication No. WO 99/53050 published on Oct. 21, 1999; and PCT Publication No. WO 02/00904 published on Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083 published on Aug. 20, 1998). Genetic and molecular evidences have been obtained suggesting that dsRNA mediated mRNA cleavage may have been the conserved mechanism underlying these gene silencing phenomena (Elmayan et al., Plant Cell 10:1747-1757 (1998); Galun, In Vitro Cell. Dev. Biol. Plant 41(2):113-123 (2005); Pickford et al, Cell. Mol. Life Sci. 60(5):871-882 (2003)).

As stated herein, "suppression" refers to a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in a non-transgenic or wild type cell. The terms "non-transgenic" and "wild type" are used interchangeably herein.

"Altering expression" refers to the production of gene product(s) in transgenic organisms in amounts or proportions that differ significantly from the amount of the gene product(s) produced by the corresponding wild-type organisms (i.e., expression is increased or decreased).

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms.

"Transient transformation" refers to the introduction of a nucleic acid fragment into the nucleus, or DNA-containing organelle, of a host organism resulting in gene expression without genetically stable inheritance.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

The terms "monocot" and "monocotyledonous plant" are used interchangeably herein. A monocot of the current disclosure includes the Gramineae.

The terms "dicot" and "dicotyledonous plant" are used interchangeably herein. A dicot of the current disclosure includes the following families: Brassicaceae, Leguminosae, and Solanaceae.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Transient expression" refers to the temporary expression of often reporter genes such as β-glucuronidase (GUS), fluorescent protein genes ZS-GREEN1, ZS-YELLOW1 N1, AM-CYAN1, DS-RED in selected certain cell types of the host organism in which the transgenic gene is introduced temporally by a transformation method. The transformed materials of the host organism are subsequently discarded after the transient gene expression assay.

Standard recombinant DNA and molecular cloning techniques used herein are well known in the art and are described more fully in Sambrook, J. et al., In Molecular Cloning: A Laboratory Manual; $2^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

"PCR" or "Polymerase Chain Reaction" is a technique for the synthesis of large quantities of specific DNA segments, consisting of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "recombinant DNA construct" or "recombinant expression construct" is used interchangeably and refers to a discrete polynucleotide into which a nucleic acid sequence or fragment can be moved. Preferably, it is a plasmid vector or a fragment thereof comprising the promoters of the present disclosure. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

Various changes in phenotype are of interest including, but not limited to, modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic characteristics and traits such as yield and heterosis increase, the choice of genes for transformation will change accordingly. General categories of genes of interest include, but are not limited to, those genes involved in information, such as zinc fingers, those involved in communication, such as kinases, and those involved in housekeeping, such as heat shock proteins. More specific categories of transgenes, for example, include, but are not limited to, genes encoding important traits for agronomics, insect resistance, disease resistance, herbicide resistance, sterility, grain or seed characteristics, and commercial products. Genes of interest include, generally, those involved in oil, starch, carbohydrate, or nutrient metabolism as well as those affecting seed size, plant development, plant growth regulation, and yield improvement. Plant development and growth regulation also refer to the development and growth regulation of various parts of a plant, such as the flower, seed, root, leaf and shoot.

Other commercially desirable traits are genes and proteins conferring cold, heat, salt, and drought resistance.

Disease and/or insect resistance genes may encode resistance to pests that have great yield drag such as for example, anthracnose, soybean mosaic virus, soybean cyst nematode, root-knot nematode, brown leaf spot, Downy mildew, purple seed stain, seed decay and seedling diseases caused commonly by the fungi—*Pythium* sp., *Phytophthora* sp., *Rhizoctonia* sp., *Diaporthe* sp. Bacterial blight caused by the bacterium *Pseudomonas syringae* pv. *Glycinea*. Genes conferring insect resistance include, for example, *Bacillus thuringiensis* toxic protein genes (U.S. Pat. Nos. 5,366,892; 5,747,450; 5,737,514; 5,723,756; 5,593,881; and Geiser et al (1986) Gene 48:109); lectins (Van Damme et al. (1994) Plant Mol. Biol. 24:825); and the like.

Herbicide resistance traits may include genes coding for resistance to herbicides that act to inhibit the action of acetolactate synthase (ALS), in particular the sulfonylurea-type herbicides (e.g., the acetolactate synthase ALS gene containing mutations leading to such resistance, in particular the S4 and/or HRA mutations). The ALS-gene mutants encode resistance to the herbicide chlorsulfuron. Glyphosate acetyl transferase (GAT) is an N-acetyltransferase from

*Bacillus licheniformis* that was optimized by gene shuffling for acetylation of the broad spectrum herbicide, glyphosate, forming the basis of a novel mechanism of glyphosate tolerance in transgenic plants (Castle et al. (2004) *Science* 304, 1151-1154).

Antibiotic resistance genes include, for example, neomycin phosphotransferase (npt) and hygromycin phosphotransferase (hpt). Two neomycin phosphotransferase genes are used in selection of transformed organisms: the neomycin phosphotransferase I (nptI) gene and the neomycin phosphotransferase II (nptII) gene. The second one is more widely used. It was initially isolated from the transposon Tn5 that was present in the bacterium strain *Escherichia coli* K12. The gene codes for the aminoglycoside 3'-phosphotransferase (denoted aph(3')-II or NPTII) enzyme, which inactivates by phosphorylation a range of aminoglycoside antibiotics such as kanamycin, neomycin, geneticin and paroromycin. NPTII is widely used as a selectable marker for plant transformation. It is also used in gene expression and regulation studies in different organisms in part because N-terminal fusions can be constructed that retain enzyme activity. NPTII protein activity can be detected by enzymatic assay. In other detection methods, the modified substrates, the phosphorylated antibiotics, are detected by thin-layer chromatography, dot-blot analysis or polyacrylamide gel electrophoresis. Plants such as maize, cotton, tobacco, *Arabidopsis*, flax, soybean and many others have been successfully transformed with the nptII gene.

The hygromycin phosphotransferase (denoted hpt, hph or aphIV) gene was originally derived from *Escherichia coli*. The gene codes for hygromycin phosphotransferase (HPT), which detoxifies the aminocyclitol antibiotic hygromycin B. A large number of plants have been transformed with the hpt gene and hygromycin B has proved very effective in the selection of a wide range of plants, including monocotyledonous. Most plants exhibit higher sensitivity to hygromycin B than to kanamycin, for instance cereals. Likewise, the hpt gene is used widely in selection of transformed mammalian cells. The sequence of the hpt gene has been modified for its use in plant transformation. Deletions and substitutions of amino acid residues close to the carboxy (C)-terminus of the enzyme have increased the level of resistance in certain plants, such as tobacco. At the same time, the hydrophilic C-terminus of the enzyme has been maintained and may be essential for the strong activity of HPT. HPT activity can be checked using an enzymatic assay. A non-destructive callus induction test can be used to verify hygromycin resistance.

Genes involved in plant growth and development have been identified in plants. One such gene, which is involved in cytokinin biosynthesis, is isopentenyl transferase (IPT). Cytokinin plays a critical role in plant growth and development by stimulating cell division and cell differentiation (Sun et al. (2003), Plant Physiol. 131: 167-176).

Calcium-dependent protein kinases (CDPK), a family of serine-threonine kinase found primarily in the plant kingdom, are likely to function as sensor molecules in calcium-mediated signaling pathways. Calcium ions are important second messengers during plant growth and development (Harper et al. Science 252, 951-954 (1993); Roberts et al. Curr. Opin. Cell Biol. 5, 242-246 (1993); Roberts et al. Annu. Rev. Plant Mol. Biol. 43, 375-414 (1992)).

Nematode responsive protein (NRP) is produced by soybean upon the infection of soybean cyst nematode. NRP has homology to a taste-modifying glycoprotein miraculin and the NF34 protein involved in tumor formation and hyper response induction. NRP is believed to function as a defense-inducer in response to nematode infection (Tenhaken et al. BMC Bioinformatics 6:169 (2005)).

The quality of seeds and grains is reflected in traits such as levels and types of fatty acids or oils, saturated and unsaturated, quality and quantity of essential amino acids, and levels of carbohydrates. Therefore, commercial traits can also be encoded on a gene or genes that could increase for example methionine and cysteine, two sulfur containing amino acids that are present in low amounts in soybeans. Cystathionine gamma synthase (CGS) and serine acetyl transferase (SAT) are proteins involved in the synthesis of methionine and cysteine, respectively.

Other commercial traits can encode genes to increase for example monounsaturated fatty acids, such as oleic acid, in oil seeds. Soybean oil for example contains high levels of polyunsaturated fatty acids and is more prone to oxidation than oils with higher levels of monounsaturated and saturated fatty acids. High oleic soybean seeds can be prepared by recombinant manipulation of the activity of oleoyl 12-desaturase (Fad2). High oleic soybean oil can be used in applications that require a high degree of oxidative stability, such as cooking for a long period of time at an elevated temperature.

Raffinose saccharides accumulate in significant quantities in the edible portion of many economically significant crop species, such as soybean (*Glycine max* L. Merrill), sugar beet (*Beta vulgaris*), cotton (*Gossypium hirsutum* L.), canola (*Brassica* sp.) and all of the major edible leguminous crops including beans (*Phaseolus* sp.), chick pea (*Cicer arietinum*), cowpea (*Vigna unguiculata*), mung bean (*Vigna radiata*), peas (*Pisum sativum*), lentil (*Lens culinaris*) and lupine (*Lupinus* sp.). Although abundant in many species, raffinose saccharides are an obstacle to the efficient utilization of some economically important crop species.

Down regulation of the expression of the enzymes involved in raffinose saccharide synthesis, such as galactinol synthase for example, would be a desirable trait.

In certain embodiments, the present disclosure contemplates the transformation of a recipient cell with more than one advantageous transgene. Two or more transgenes can be supplied in a single transformation event using either distinct transgene-encoding vectors, or a single vector incorporating two or more gene coding sequences. Any two or more transgenes of any description, such as those conferring herbicide, insect, disease (viral, bacterial, fungal, and nematode), or drought resistance, oil quantity and quality, or those increasing yield or nutritional quality may be employed as desired.

Glyceraldehyde 3-phosphate dehydrogenase (abbreviated as GAPD) is an enzyme of ~37 kDa that catalyzes the conversion of glyceraldehyde 3-phosphate to D-glycerate 1,3-bisphosphate, the sixth step in the glycolytic breakdown of glucose, an important pathway of energy and carbon molecule supply which takes place in the cytosol of eukaryotic cells. GAPD is highly conserved and predicted sequences very similar to the soybean full length GAPD GAPDH amino acid sequence (SEQ ID NO:16) are identified in several species including lotus, rose, potato, tobacco, alfalfa, tomato, pea, and grape etc. It is demonstrated herein that the soybean glyceraldehyde-3-phosphate dehydrogenasegene promoter named GM-GAPD can, in fact, be used as a constitutive promoter to drive expression of transgenes in plants, and that such promoter can be isolated and used by one skilled in the art.

This invention concerns a recombinant DNA construct comprising a constitutive eukaryotic glyceraldehyde-3-phosphate dehydrogenase gene GAPD promoter. This invention also concerns a recombinant DNA construct comprising a promoter wherein said promoter consists essentially of the nucleotide sequence set forth in SEQ ID NO:1, or an isolated polynucleotide comprising a promoter wherein said promoter comprises the nucleotide sequence set forth in SEQ ID NOs: 1, 2, 3, 4, 5, 6, or 39 or a functional fragment of SEQ ID NOs: 1, 2, 3, 4, 5, 6, or 39.

The expression patterns of GAPD gene and its promoter are set forth in Examples 1-7.

The promoter activity of the soybean genomic DNA fragment SEQ ID NO:1 upstream of the GAPD protein coding sequence was assessed by linking the fragment to a green fluorescence reporter gene, ZS-GREEN1 (GFP) (Tsien, Annu. Rev. Biochem. 67:509-544 (1998); Matz et al., Nat. Biotechnol. 17:969-973 (1999)), transforming the promoter:GFP expression cassette into soybean, and analyzing GFP expression in various cell types of the transgenic plants (see Example 7). GFP expression was detected in most parts of the transgenic plants. These results indicated that the nucleic acid fragment contained a constitutive promoter.

It is clear from the disclosure set forth herein that one of ordinary skill in the art could perform the following procedure:

1) operably linking the nucleic acid fragment containing the GAPD promoter sequence to a suitable reporter gene; there are a variety of reporter genes that are well known to those skilled in the art, including the bacterial GUS gene, the firefly luciferase gene, and the cyan, green, red, and yellow fluorescent protein genes; any gene for which an easy and reliable assay is available can serve as the reporter gene.

2) transforming a chimeric GAPD promoter:reporter gene expression cassette into an appropriate plant for expression of the promoter. There are a variety of appropriate plants which can be used as a host for transformation that are well known to those skilled in the art, including the dicots, *Arabidopsis*, tobacco, soybean, oilseed rape, peanut, sunflower, safflower, cotton, tomato, potato, cocoa and the monocots, corn, wheat, rice, barley and palm.

3) testing for expression of the GAPD promoter in various cell types of transgenic plant tissues, e.g., leaves, roots, flowers, seeds, transformed with the chimeric GAPD promoter:reporter gene expression cassette by assaying for expression of the reporter gene product.

In another aspect, this invention concerns a recombinant DNA construct comprising at least one heterologous nucleic acid fragment operably linked to any promoter, or combination of promoter elements, of the present disclosure. Recombinant DNA constructs can be constructed by operably linking the nucleic acid fragment of the disclosure GAPD promoter or a fragment that is substantially similar and functionally equivalent to any portion of the nucleotide sequence set forth in SEQ ID NOs: 1, 2, 3, 4, 5, 6, or 39 to a heterologous nucleic acid fragment. Any heterologous nucleic acid fragment can be used to practice the invention. The selection will depend upon the desired application or phenotype to be achieved. The various nucleic acid sequences can be manipulated so as to provide for the nucleic acid sequences in the proper orientation. It is believed that various combinations of promoter elements as described herein may be useful in practicing the present invention.

In another aspect, this disclosure concerns a recombinant DNA construct comprising at least one acetolactate synthase (ALS) nucleic acid fragment operably linked to GAPD promoter, or combination of promoter elements, of the present disclosure. The acetolactate synthase gene is involved in the biosynthesis of branched chain amino acids in plants and is the site of action of several herbicides including sulfonyl urea. Expression of a mutated acetolactate synthase gene encoding a protein that can no longer bind the herbicide will enable the transgenic plants to be resistant to the herbicide (U.S. Pat. No. 5,605,011, U.S. Pat. No. 5,378,824). The mutated acetolactate synthase gene is also widely used in plant transformation to select transgenic plants.

In another embodiment, this disclosure concerns host cells comprising either the recombinant DNA constructs of the disclosure as described herein or isolated polynucleotides of the disclosure as described herein. Examples of host cells which can be used to practice the disclosure include, but are not limited to, yeast, bacteria, and plants.

Plasmid vectors comprising the instant recombinant DNA construct can be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene.

Methods for transforming dicots, primarily by use of *Agrobacterium tumefaciens*, and obtaining transgenic plants have been published, among others, for cotton (U.S. Pat. No. 5,004,863, U.S. Pat. No. 5,159,135); soybean (U.S. Pat. No. 5,569,834, U.S. Pat. No. 5,416,011); *Brassica* (U.S. Pat. No. 5,463,174); peanut (Cheng et al., Plant Cell Rep. 15:653-657 (1996), McKently et al., Plant Cell Rep. 14:699-703 (1995)); papaya (Ling et al., Bio/technology 9:752-758 (1991)); and pea (Grant et al., Plant Cell Rep. 15:254-258 (1995)). For a review of other commonly used methods of plant transformation see Newell, C. A., Mol. Biotechnol. 16:53-65 (2000). One of these methods of transformation uses *Agrobacterium rhizogenes* (Tepfler, M. and Casse-Delbart, F., Microbiol. Sci. 4:24-28 (1987)). Transformation of soybeans using direct delivery of DNA has been published using PEG fusion (PCT Publication No. WO 92/17598), electroporation (Chowrira et al., Mol. Biotechnol. 3:17-23 (1995); Christou et al., Proc. Natl. Acad. Sci. U.S.A. 84:3962-3966 (1987)), microinjection, or particle bombardment (McCabe et al., Biotechnology 6:923-926 (1988); Christou et al., Plant Physiol. 87:671-674 (1988)).

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, Calif., 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present disclosure containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook, J. et al., In Molecular Cloning: A Laboratory Manual; $2^{nd}$ ed.; Cold Spring Harbor Laboratory Press: Cold Spring Harbor, N.Y., 1989; Maliga et al., In Methods in Plant Molecular Biology; Cold Spring Harbor Press, 1995; Birren et al., In Genome Analysis: Detecting Genes, 1; Cold Spring Harbor: New York, 1998; Birren et al., In Genome Analysis: Analyzing DNA, 2; Cold Spring Harbor: New York, 1998; Clark, Ed., In Plant Molecular Biology: A Laboratory Manual; Springer: New York, 1997).

The skilled artisan will also recognize that different independent transformation events will result in different levels and patterns of expression of the chimeric genes (Jones et al., EMBO J. 4:2411-2418 (1985); De Almeida et al., Mol. Gen. Genetics 218:78-86 (1989)). Thus, multiple events must be screened in order to obtain lines displaying the desired expression level and pattern. Such screening may be accomplished by Northern analysis of mRNA expression, Western analysis of protein expression, or phenotypic analysis. Also of interest are seeds obtained from transformed plants displaying the desired gene expression profile.

The level of activity of the GAPD promoter is weaker than that of many known strong promoters, such as the CaMV 35S promoter (Atanassova et al., Plant Mol. Biol. 37:275-285 (1998); Battraw and Hall, Plant Mol. Biol. 15:527-538 (1990); Holtorf et al., Plant Mol. Biol. 29:637-646 (1995); Jefferson et al., EMBO J. 6:3901-3907 (1987); Wilmink et al., Plant Mol. Biol. 28:949-955 (1995)), the *Arabidopsis* ubiquitin extension protein promoters (Callis et al., J. Biol. Chem. 265(21):12486-12493 (1990)), a tomato ubiquitin gene promoter (Rollfinke et al., Gene 211:267-276 (1998)), a soybean heat shock protein promoter, and a maize H3 histone gene promoter (Atanassova et al., Plant Mol. Biol. 37:275-285 (1998)). Universal moderate expression of chimeric genes in most plant cells makes the GAPD promoter of the instant disclosure especially useful when moderate constitutive expression of a target heterologous nucleic acid fragment is required.

Another general application of the GAPD promoter of the disclosure is to construct chimeric genes that can be used to reduce expression of at least one heterologous nucleic acid fragment in a plant cell. To accomplish this, a chimeric gene designed for gene silencing of a heterologous nucleic acid fragment can be constructed by linking the fragment to the GAPD promoter of the present disclosure. (See U.S. Pat. No. 5,231,020, and PCT Publication No. WO 99/53050 published on Oct. 21, 1999, PCT Publication No. WO 02/00904 published on Jan. 3, 2002, and PCT Publication No. WO 98/36083 published on Aug. 20, 1998, for methodology to block plant gene expression via cosuppression.) Alternatively, a chimeric gene designed to express antisense RNA for a heterologous nucleic acid fragment can be constructed by linking the fragment in reverse orientation to the GAPD promoter of the present disclosure. (See U.S. Pat. No. 5,107,065 for methodology to block plant gene expression via antisense RNA.) Either the cosuppression or antisense chimeric gene can be introduced into plants via transformation. Transformants wherein expression of the heterologous nucleic acid fragment is decreased or eliminated are then selected.

This invention also concerns a method of altering (increasing or decreasing) the expression of at least one heterologous nucleic acid fragment in a plant cell which comprises:
 (a) transforming a plant cell with the recombinant expression construct described herein;
 (b) growing fertile mature plants from the transformed plant cell of step (a);
 (c) selecting plants containing a transformed plant cell wherein the expression of the heterologous nucleic acid fragment is increased or decreased.

Transformation and selection can be accomplished using methods well-known to those skilled in the art including, but not limited to, the methods described herein.

Non-limiting examples of methods and compositions disclosed herein are as follows:

1. A recombinant DNA construct comprising a nucleotide sequence comprising any one of the sequence set forth in SEQ ID NO:1, SEQ ID NO:2, SEQ ID NO:3, SEQ ID NO:4, SEQ ID NO:5, SEQ ID NO:6, SEQ ID NO:39, or a functional fragment thereof, operably linked to at least one heterologous sequence, wherein said nucleotide sequence is a constitutive promoter.

2. The recombinant DNA construct of embodiment 1, wherein said nucleotide sequence has at least 95% identity, based on the Clustal V method of alignment with pairwise alignment default parameters (KTUPLE=2, GAP PENALTY=5, WINDOW=4 and DIAGONALS SAVED=4), when compared to any one of the sequence set forth in SEQ ID NO:1, SEQ ID NO:2, SEQ ID NO:3, SEQ ID NO:4, SEQ ID NO:5, SEQ ID NO:6, or SEQ ID NO:39.

3. A vector comprising the recombinant DNA construct of embodiment 1.

4. A cell comprising the recombinant DNA construct of embodiment 1.

5. The cell of embodiment 4, wherein the cell is a plant cell.

6. A transgenic plant having stably incorporated into its genome the recombinant DNA construct of embodiment 1.

7. The transgenic plant of embodiment 6 wherein said plant is a dicot plant.

8. The transgenic plant of embodiment 7 wherein the plant is soybean.

9. A transgenic seed produced by the transgenic plant of embodiment 7, wherein the transgenic seed comprises the recombinant DNA construct.

10. The recombinant DNA construct of embodiment 1 wherein the at least one heterologous sequence codes for a gene selected from the group consisting of: a reporter gene, a selection marker, a disease resistance conferring gene, a herbicide resistance conferring gene, an insect resistance conferring gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in cold resistance, a gene involved in heat resistance and a gene involved in salt resistance in plants.

11. The recombinant DNA construct of embodiment 1, wherein the at least one heterologous sequence encodes a protein selected from the group consisting of: a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and protein involved in salt resistance in plants.

12. A method of expressing a coding sequence or a functional RNA in a plant comprising:
   a) introducing the recombinant DNA construct of embodiment 1 into the plant, wherein the at least one heterologous sequence comprises a coding sequence or encodes a functional RNA;
   b) growing the plant of step a); and
   c) selecting a plant displaying expression of the coding sequence or the functional RNA of the recombinant DNA construct.

13. A method of transgenically altering a marketable plant trait, comprising:
   a) introducing a recombinant DNA construct of embodiment 1 into the plant;
   b) growing a fertile, mature plant resulting from step a); and
   c) selecting a plant expressing the at least one heterologous sequence in at least one plant tissue based on the altered marketable trait.

14. The method of embodiment 13 wherein the marketable trait is selected from the group consisting of: disease resistance, herbicide resistance, insect resistance carbohydrate metabolism, fatty acid metabolism, amino acid metabolism, plant development, plant growth regulation, yield improvement, drought resistance, cold resistance, heat resistance, and salt resistance.

15. A method for altering expression of at least one heterologous sequence in a plant comprising:
   (a) transforming a plant cell with the recombinant DNA construct of embodiment 1;
   (b) growing fertile mature plants from transformed plant cell of step (a); and
   (c) selecting plants containing the transformed plant cell wherein the expression of the heterologous sequence is increased or decreased.

16. The method of Embodiment 15 wherein the plant is a soybean plant.

17. A method for expressing a green fluorescent protein ZS-GREEN1 in a host cell comprising:
   (a) transforming a host cell with the recombinant DNA construct of embodiment 1; and,
   (b) growing the transformed host cell under conditions that are suitable for expression of the recombinant DNA construct, wherein expression of the recombinant DNA construct results in production of increased levels of ZS GREEN1 protein in the transformed host cell when compared to a corresponding non-transformed host cell.

18. A plant stably transformed with a recombinant DNA construct comprising a soybean constitutive promoter and a heterologous nucleic acid fragment operably linked to said constitutive promoter, wherein said constitutive promoter is a capable of controlling expression of said heterologous nucleic acid fragment in a plant cell, and further wherein said constitutive promoter comprises any of the sequences set forth in SEQ ID NO:1, SEQ ID NO:2, SEQ ID NO:3, SEQ ID NO:4, SEQ ID NO:5, SEQ ID NO:6, or SEQ ID NO:39.

EXAMPLES

The present invention is further defined in the following Examples, in which parts and percentages are by weight and degrees are Celsius, unless otherwise stated. Sequences of promoters, cDNA, adaptors, and primers listed in this invention all are in the 5' to 3' orientation unless described otherwise. Techniques in molecular biology were typically performed as described in Ausubel, F. M. et al., In Current Protocols in Molecular Biology; John Wiley and Sons: New York, 1990 or Sambrook, J. et al., In Molecular Cloning: A Laboratory Manual; $2^{nd}$ ed.; Cold Spring Harbor Laboratory Press: Cold Spring Harbor, N.Y., 1989 (hereinafter "Sambrook et al., 1989"). It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Identification of Soybean Constitutive Promoter Candidate Genes

Soybean expression sequence tags (EST) were generated by sequencing randomly selected clones from cDNA libraries constructed from different soybean tissues. Multiple EST sequences could often be found with different lengths representing the different regions of the same soybean gene. If more EST sequences representing the same gene are frequently found from a tissue-specific cDNA library such as a flower library than from a leaf library, there is a possibility that the represented gene could be a flower preferred gene candidate. Likewise, if similar numbers of ESTs for the same gene were found in various libraries constructed from different tissues, the represented gene could be a constitutively expressed gene. Multiple EST sequences representing the same soybean gene were compiled electronically based on their overlapping sequence homology into a unique full length sequence representing the gene. These assembled unique gene sequences were accumulatively collected in Pioneer Hi-Bred Intl proprietary searchable databases.

To identify constitutive promoter candidate genes, searches were performed to look for gene sequences that were found at similar frequencies in leaf, root, flower, embryos, pod, and also in other tissues. One unique gene PSO467143 was identified in the search to be a moderate constitutive gene candidate. PSO467143 cDNA sequence (SEQ ID NO:15) as well as its putative translated protein sequence (SEQ ID NO:16) were used to search National Center for Biotechnology Information (NCBI) databases. Both PSO467143 nucleotide and amino acid sequences were found to have high homology to eukaryotic glyceraldehyde-3-phosphate dehydrogenase genes discovered in several plant species including several *Glycine max* clones such as SEQ ID NO:38, NCBI accession DQ355800.

Solexa digital gene expression dual-tag-based mRNA profiling using the Illumina (Genome Analyzer) GA2 machine is a restriction enzyme site anchored tag-based technology, in this regard similar to Mass Parallel Signature Sequence transcript profiling technique (MPSS), but with two key differences (Morrissy et al., Genome Res. 19:1825-1835 (2009); Brenner et al., Proc. Natl. Acad. Sci. USA 97:1665-70 (2000)). Firstly, not one but two restriction enzymes were used, DpnII and NlaI, the combination of which increases gene representation and helps moderate expression variances. The aggregate occurrences of all the resulting sequence reads emanating from these DpnII and NlaI sites, with some repetitive tags removed computationally were used to determine the overall gene expression levels. Secondly, the tag read length used here is 21 nucleotides, giving the Solexa tag data higher gene match fidelity than the shorter 17-mers used in MPSS. Soybean mRNA global gene expression profiles are stored in a Pioneer proprietary database TDExpress (Tissue Development Expression Browser). Candidate genes with different expression patterns can be searched, retrieved, and further evaluated.

Figure 1:
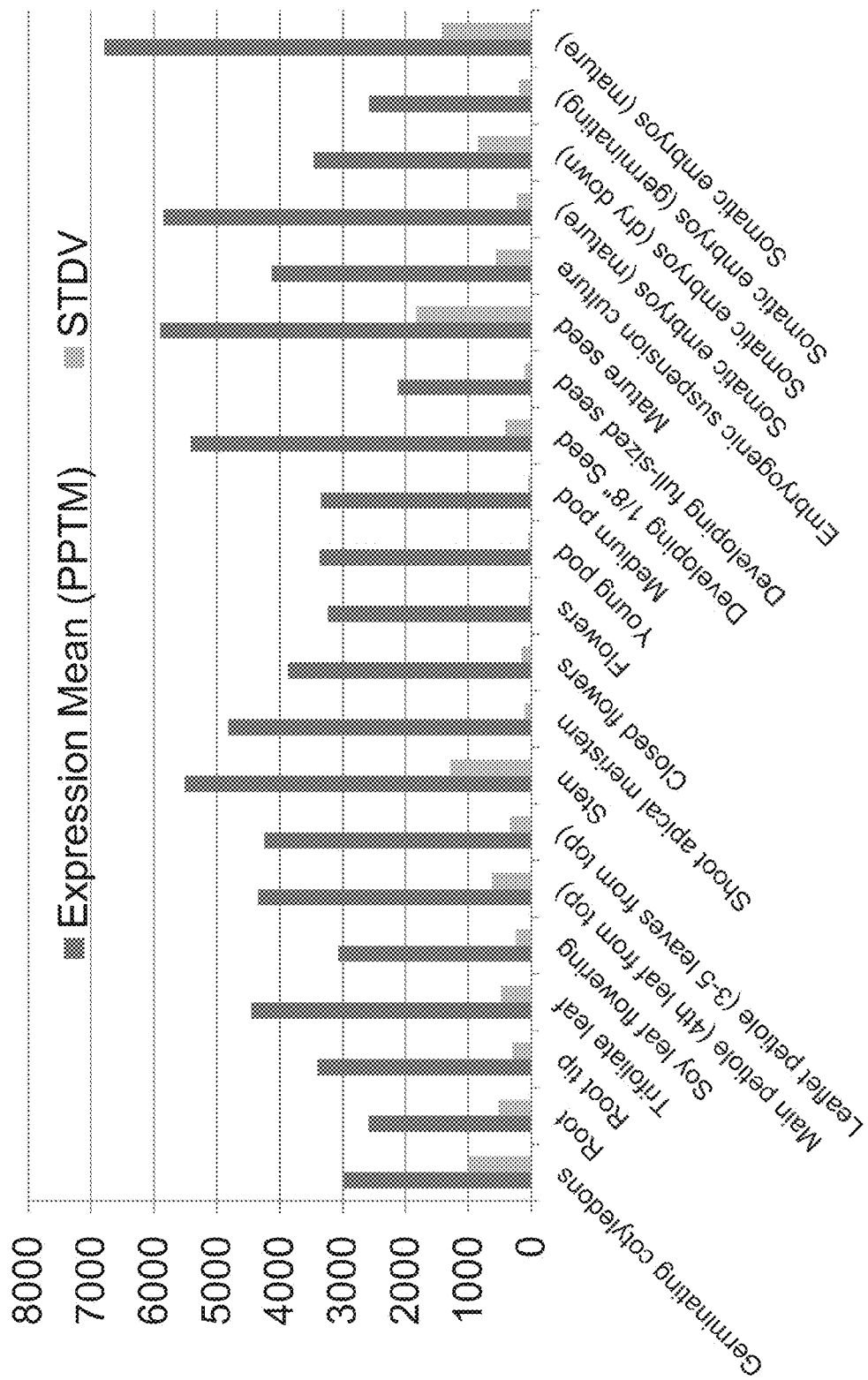

The soybean glyceraldehyde-3-phosphate dehydrogenase gene PSO467143 (GAPD) corresponds to predicted gene Glyma06g18110.1 in the soybean genome, sequenced by the DOE-JGI Community Sequencing Program consortium (Schmutz J, et al., Nature 463:178-183 (2010)). The GAPD expression profiles in twenty one tissues were retrieved from the TDExpress database using the gene ID Glyma06g18110.1 and presented as parts per ten millions (PPTM) averages of three experimental repeats (FIG. 1). The GAPD gene is expressed in all checked tissues at similarly moderate levels to qualify as a candidate gene from which to clone a moderate constitutive promoter.

Example 2

Isolation of Soybean GAPD Promoter

The PSO467143 cDNA sequence was BLAST searched against the soybean genome sequence database (Schmutz J, et al., Nature 463:178-183 (2010)) to identify corresponding genomic DNA. The ~1.5 kb sequence upstream of the PSO467143 start codon ATG was selected as GAPD promoter to be amplified by PCR (polymerase chain reaction). The primers shown in SEQ ID NO:7 and 8 were then designed to amplify by PCR the putative full length 1469 bp GAPD promoter from soybean cultivar Jack genomic DNA (SEQ ID NO:1). SEQ ID NO:7 contains a recognition site for the restriction enzyme XmaI. SEQ ID NO:8 contains a recognition site for the restriction enzyme NcoI. The XmaI and NcoI sites were included for subsequent cloning.

Figure 3A:
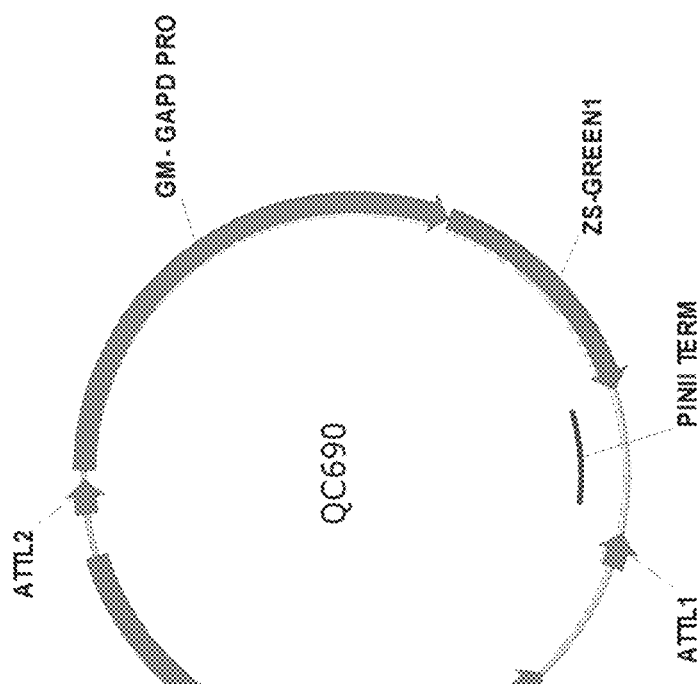

PCR cycle conditions were 94° C. for 4 minutes; 35 cycles of 94° C. for 30 seconds, 60° C. for 1 minute, and 68° C. for 2 minutes; and a final 68° C. for 5 minutes before holding at 4° C. using the Platinum high fidelity Taq DNA polymerase (Invitrogen). The PCR reaction was resolved using agarose gel electrophoresis to identify the right size PCR product representing the ~1.5 Kb GAPD promoter. The PCR fragment was first cloned into pCR2.1-TOPO vector by TA cloning (Invitrogen). Several clones containing the ~1.5 Kb DNA insert were sequenced and only one clone with the correct GAPD promoter sequence was selected for further cloning. The plasmid DNA of the selected clone was digested with XmaI and NcoI restriction enzymes to move the GAPD promoter upstream of the ZS-GREEN1 (GFP) fluorescent reporter gene in QC690 (FIG. 3A, SEQ ID NO:17). Construct QC690 contains the recombination sites AttL1 and AttL2 (SEQ ID NO:32 and 35) to qualify as a GATEWAY® cloning entry vector (Invitrogen). The 1469 bp sequence upstream of the GAPD gene PSO467143 start codon ATG including the XmaI and NcoI sites is herein designated as soybean GAPD promoter, GM-GAPD PRO (SEQ ID NO:1).

Comparison of SEQ ID NO:1 to a soybean cDNA library revealed that SEQ ID NO:1 comprised a 5' untranslated region (UTR) at its 3' end of at least 83 base pairs (SEQ ID NO:40). It is known to one of skilled in the art that a 5' UTR region can be altered (deletion or substitutions of bases) or replaced by an alternative 5' UTR while maintaining promoter activity.

Example 3

GAPD Promoter Copy Number Analysis

Figure 2A:
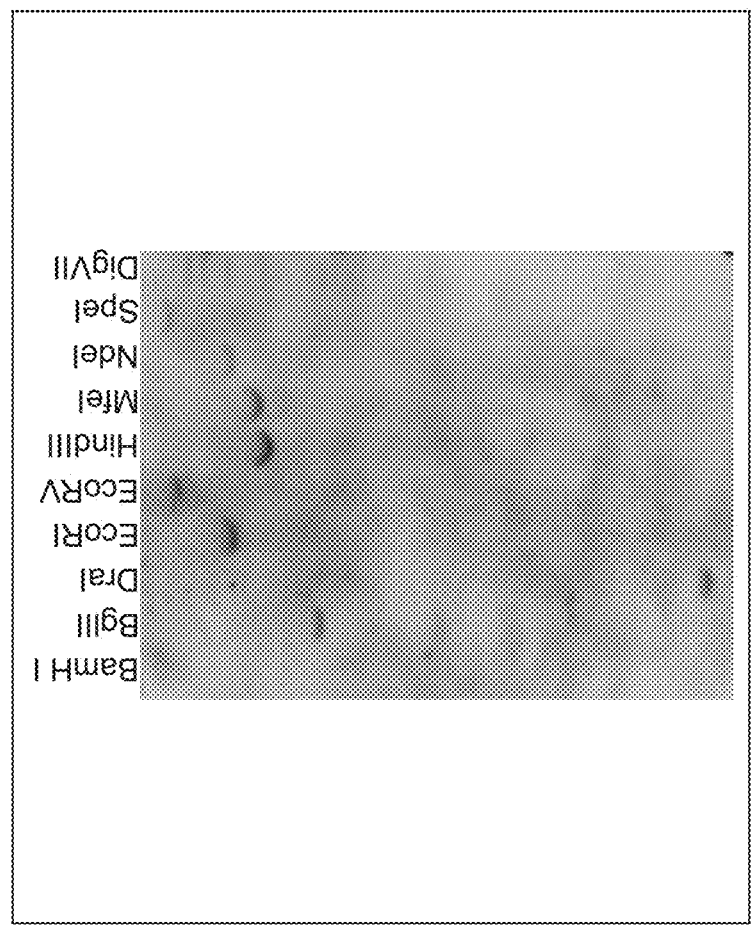
FIG. 2A is GAPD promoter copy number analysis by Southern and shows the image of a Southern blot hybridized with a 637 bp GAPD promoter probe made with primers QC690-S3 and QC690-A by PCR.
Figure 2B:
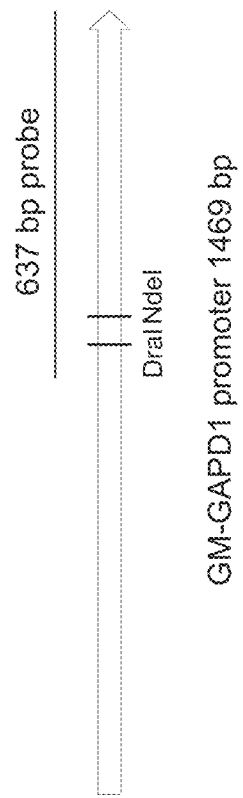
FIG. 2B shows restriction enzyme recognitions sites in the GAPD probe region.

Southern hybridization analysis was performed to examine whether additional copies or sequences with significant similarity to the GAPD promoter exist in the soybean genome. Soybean 'Jack' wild type genomic DNA was digested with nine different restriction enzymes, BamHI, BglII, DraI, EcoRI, EcoRV, HindIII, MfeI, NdeI, and SpeI and distributed in a 0.7% agarose gel by electrophoresis. The DNA was blotted onto Nylon membrane and hybridized at 60° C. with digoxigenin labeled GAPD promoter DNA probe in Easy-Hyb Southern hybridization solution, and then sequentially washed 10 minutes with 2×SSC/0.1% SDS at room temperature and 3×10 minutes at 65° C. with 0.1×SSC/0.1% SDS according to the protocol provided by the manufacturer (Roche Applied Science, Indianapolis, Ind.). The GAPD promoter probe was labeled by PCR using the DIG DNA labeling kit (Roche Applied Science) with primers QC690-S3 (SEQ ID NO:12) and QC690-A (SEQ ID NO:9) and QC690 plasmid DNA (SEQ ID NO:17) as the template to make a 637 bp long probe covering the 3' half of the GAPD promoter (FIG. 2B).

Only two DraI and NdeI of the nine restriction enzymes would cut the 637 bp GAPD promoter probe region. DraI would cut the region once into 54, and 583 bp fragments so only the 3' GAPD promoter fragment corresponding to the 583 bp probe fragment would be detected by Southern hybridization with the 637 bp GAPD probe (FIG. 2B). NdeI would cut the region only once into 83, and 554 bp fragments so only the 3' GAPD promoter fragment corresponding to the 554 bp probe fragment would be detected. DNA fragments created by DraI or NdeI digestion containing 54 or 83 bp long sequences corresponding to the 5' GAPD probe regions was too short to stably hybridize to the probe under stringent conditions. None of the other seven restriction enzymes BamHI, BglII, EcoRI, EcoRV, HindIII, MfeI, and SpeI would cut the GAPD promoter probe region. Therefore, only one band would be expected to be hybridized for each of the nine digestions if only one copy of GAPD promoter sequence exists in soybean genome (FIG. 2B). The observation that only one band was detected in all nine digestions suggested that there is only one sequence with significant homology to the 637 bp probe region of the GAPD promoter in soybean genome (FIG. 2A). The DIGVII molecular markers used on the Southern blot are 8576, 7427, 6106, 4899, 3639, 2799, 1953, 1882, 1515, 1482, 1164, and 992 bp.

Since the whole soybean genome sequence is now publically available (Schmutz J, et al., Nature 463:178-183 (2010)), the GAPD promoter copy numbers can also be evaluated by searching the soybean genome with the 1469 bp promoter sequence (SEQ ID NO:1). Consistent with above Southern analysis, one sequence Gm06:14427908-14426438 (rev) very similar to the GAPD promoter sequence 7-1469 bp was identified. Parts of the 5' end 6 bp and 3' end 6 bp of the 1469 bp GAPD promoter may not match the genomic Gm06 sequence since they are artificially added XmaI and NcoI sites. The BLAST search did not detect any other sequence with significant homology to the GAPD promoter supporting the conclusion that there is only one GAPD promoter sequence in soybean genome.

FIG. 8 shows a nucleotide sequence alignment of SEQ ID NO:1, comprising the full length GAPD promoter of the disclosure, and SEQ ID NO:39, comprising a 1471 bp native soybean genomic DNA from Gm06:14427908-14426438 (rev) cultivar "Williams82" (Schmutz J. et al., Nature 463: 178-183, 2010). As shown in FIG. 8, the GAPD promoter of SEQ ID NO:1 is 99.2% identical to SEQ ID NO:39, based on the Clustal V method of alignment with pairwise alignment default parameters (KTUPLE=2, GAP PENALTY=5, WINDOW=4 and DIAGONALS SAVED=4). Based on the data described in Examples 1-7, it is believed that SEQ ID NO:39 has promoter activity.

Example 4

GAPD:GFP Reporter Gene Constructs and Soybean Transformation

Figure 3B:
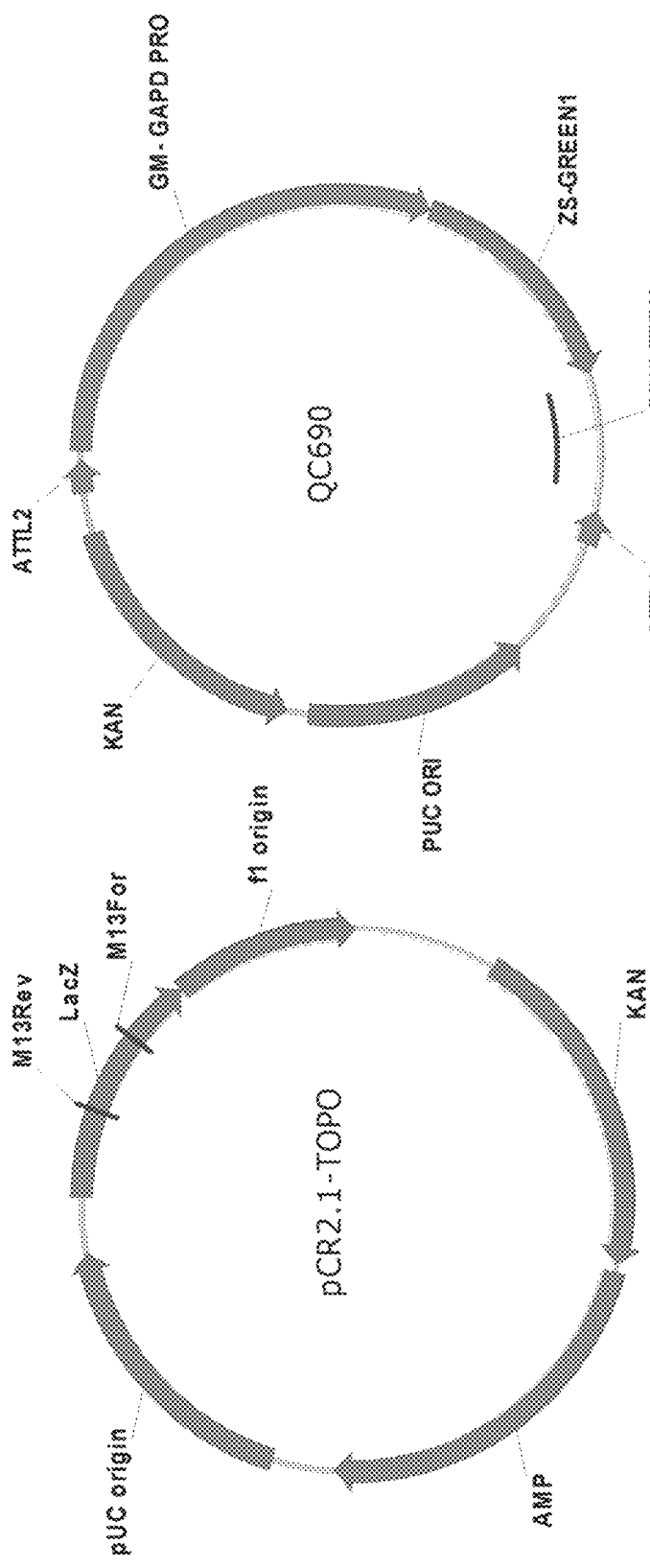

The GAPD:GFP cassette in QC690 (SEQ ID NO:17; FIG. 3A) was moved into a GATEWAY® destination vector QC478i (SEQ ID NO:18) by LR Clonase® (Invitrogen) mediated DNA recombination between the attL1 and attL2 recombination sites (SEQ ID NO:32, and 33, respectively) in QC690 and the attR1-attR2 recombination sites (SEQ ID NO:34, and 35, respectively) in QC478i to make the final transformation construct QC699 (SEQ ID NO:19; FIG. 3B).

Since the GATEWAY® destination vector QC478i already contains a soybean transformation selectable marker gene SAMS:HRA, the resulting DNA construct QC699 has the GAPD:GFP gene expression cassette linked to the SAMS:HRA cassette (FIG. 3B). Two 21 bp recombination sites attB1 and attB2 (SEQ ID NO:36, and 37, respectively) were newly created recombination sites resulting from DNA recombination between attL1 and attR1, and between attL2 and attR2, respectively. The 6897 bp DNA fragment containing the linked GAPD:GFP and SAMS:HRA expression cassettes was isolated from plasmid QC699 (SEQ ID NO:19) with AscI digestion, separated from the vector backbone fragment by agarose gel electrophoresis, and purified from the gel with a DNA gel extraction kit (QIAGEN®, Valencia, Calif.). The purified DNA fragment was transformed to soybean cultivar Jack by the method of particle gun bombardment (Klein et al., Nature 327:70-73 (1987); U.S. Pat. No. 4,945,050) as described in detail below to study the GAPD promoter activity in stably transformed soybean plants.

The same methodology as outlined above for the GAPD:GFP expression cassette construction and transformation can be used with other heterologous nucleic acid sequences encoding for example a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and salt resistance in plants.

Soybean somatic embryos from the Jack cultivar were induced as follows. Cotyledons (~3 mm in length) were dissected from surface sterilized, immature seeds and were cultured for 6-10 weeks in the light at 26° C. on a Murashige and Skoog (MS) media containing 0.7% agar and supplemented with 10 mg/ml 2,4-D (2,4-Dichlorophenoxyacetic acid). Globular stage somatic embryos, which produced secondary embryos, were then excised and placed into flasks containing liquid MS medium supplemented with 2,4-D (10 mg/ml) and cultured in the light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, Calif.). To 50 µl of a 60 mg/ml 1.0 mm gold particle suspension were added (in order): 30 µl of 30 ng/µl QC589 DNA fragment GAPD:GFP+SAMS:HRA, 20 µl of 0.1 M spermidine, and 25 µl of 5 M CaCl$_2$. The particle preparation was then agitated for 3 minutes, spun in a centrifuge for 10 seconds and the supernatant removed. The DNA-coated particles were then washed once in 400 µl 100% ethanol and resuspended in 45 µl of 100% ethanol. The DNA/particle suspension was sonicated three times for one second each. Then 5 µl of the DNA-coated gold particles was loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 100 ng/ml chlorsulfuron as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 100 ng/ml chlorsulfuron selection agent to increase mass. The embryogenic suspension cultures were then transferred to agar solid MS media plates without 2,4-D supplement to allow somatic embryos to develop. A sample of each event was collected at this stage for quantitative PCR analysis.

Cotyledon stage somatic embryos were dried-down (by transferring them into an empty small Petri dish that was seated on top of a 10 cm Petri dish containing some agar gel to allow slow dry down) to mimic the last stages of soybean seed development. Dried-down embryos were placed on germination solid media and transgenic soybean plantlets were regenerated. The transgenic plants were then transferred to soil and maintained in growth chambers for seed production.

Genomic DNA were extracted from somatic embryo samples and analyzed by quantitative PCR using a 7500 real time PCR system (Applied Biosystems, Foster City, Calif.) with gene-specific primers and FAM-labeled fluorescence probes to check copy numbers of both the SAMS:HRA expression cassette and the GAPD:GFP expression cassette. The qPCR analysis was done in duplex reactions with a heat shock protein (HSP) gene as the endogenous controls and a transgenic DNA sample with a known single copy of SAMS:HRA or GFP transgene as the calibrator. The endogenous control HSP probe was labeled with VIC and the target gene SAMS:HRA or GFP probe was labeled with FAM for the simultaneous detection of both fluorescent probes (Applied Biosystems). PCR reaction data were captured and analyzed using the sequence detection software provided with the 7500 real time PCR system and the gene copy numbers were calculated using the relative quantification methodology (Applied Biosystems).

The primers and probes used in the qPCR analysis are listed below.

SAMS forward primer: SEQ ID NO:23
FAM labeled ALS probe: SEQ ID NO:24
ALS reverse primer: SEQ ID NO:25
GFP forward primer: SEQ ID NO:26
FAM labeled GFP probe: SEQ ID NO:27
GFP reverse primer: SEQ ID NO:28
HSP forward primer: SEQ ID NO:29
VIC labeled HSP probe: SEQ ID NO:30
HSP reverse primer: SEQ ID NO:31

Only transgenic soybean events containing 1 or 2 copies of both the SAMS:HRA expression cassette and the GAPD:GFP expression cassette were selected for further gene expression evaluation and seed production (see Table 1). Events negative for GFP qPCR or with more than 2 copies for the SAMS:HRA qPCR were not further followed. GFP expressions are described in detail in EXAMPLE 7 and are also summarized in Table 1.

TABLE 1

Relative transgene copy numbers and YFP expression of GAPD:GFP transgenic plants

| Clone ID | GFP expression | GFP qPCR | SAMS:HRA qPCR |
|---|---|---|---|
| 8848.1.2 | + | 0.6 | 0.3 |
| 8848.1.3 | + | 1.5 | 1.4 |
| 8848.1.4 | + | 1.5 | 0.4 |
| 8848.1.5 | + | 1.8 | 1.7 |
| 8848.1.6 | + | 1.1 | 0.9 |
| 8848.3.1 | + | 1.5 | 0.9 |
| 8848.3.4 | + | 1.4 | 1.3 |
| 8848.6.1 | + | 1.2 | 1.1 |
| 8848.6.2 | + | 1.7 | 1.5 |
| 8848.6.4 | + | 1.8 | 0.6 |
| 8848.6.5 | + | 1.4 | 0.8 |
| 8848.6.6 | + | 1.7 | 0.5 |
| 8848.6.7 | + | 0.7 | 0.8 |
| 8848.6.10 | + | 0.7 | 1.1 |
| 8848.6.11 | + | 0.7 | 0.8 |
| 8848.6.12 | + | 0.6 | 0.5 |
| 8848.6.13 | + | 1.4 | 1.3 |
| 8848.6.15 | + | 1.3 | 0.6 |

Example 5

Construction of GAPD Promoter Deletion Constructs

To define the transcriptional elements controlling the GAPD promoter activity, the 1469 bp full length (SEQ ID NO:1) and five 5' unidirectional deletion fragments 1148 bp, 850 bp, 637 bp, 425 bp, and 211 bp in length corresponding to SEQ ID NO:2, 3, 4, 5, and 6, respectively, were made by PCR amplification from the full length soybean GAPD promoter contained in the original construct QC690 (FIG. 3A). The same antisense primer QC690-A (SEQ ID NO:9) was used in the amplification by PCR of all the six GAPD promoter fragments (SEQ ID NOs: 2, 3, 4, 5, and 6) by pairing with different sense primers SEQ ID NOs:10, 11, 12, 13, and 14, respectively. Each of the PCR amplified promoter DNA fragments was cloned into the GATEWAY® cloning ready TA cloning vector pCR8/GW/TOPO (Invitrogen) and clones with the correct orientation, relative to the GATEWAY® recombination sites attL1 and attL2, were selected by sequence confirmation. The map of construct QC690-1 (SEQ ID NO:20) containing the 1148 bp GAPD promoter fragment (SEQ ID NO:2) is shown in FIG. 4A. The maps of constructs QC690-2, 3, 4, and 5 containing the truncated GAPD promoter fragments SEQ ID NOs:3, 4, 5, and 6 are similar to QC690-1 map and are not showed. The promoter fragment in the right orientation was subsequently cloned into a GATEWAY® destination vector QC330 (SEQ ID NO:21) by GATEWAY® LR Clonase® reaction (Invitrogen) to place the promoter fragment in front of the reporter gene YFP (see the example map QC690-1Y in FIG. 4B and SEQ ID NO:22). A 21 bp GATEWAY® recombination site attB2 (SEQ ID NO:37) was inserted between the promoter and the YFP reporter gene coding region as a result of the GATEWAY® cloning process. The maps and sequences of constructs QC690-2Y, 3Y, 4Y, and 5Y containing the GAPD promoter fragments SEQ ID NOs: 3, 4, 5, and 6 are similar to QC690-1Y map and sequence and are not shown.

The GAPD:YFP promoter deletion constructs were delivered into germinating soybean cotyledons by gene gun bombardment for transient gene expression study. A similar construct pZSL90 with a constitutive promoter SCP1 (U.S. Pat. No. 6,555,673) driving YFP expression and a promoterless construct QC330-Y were used as positive and negative controls, respectively. The GAPD promoter fragments analyzed are schematically described in FIG. 5.

Example 6

Transient Expression Analysis of GAPD:YFP Constructs

The constructs containing the full length and truncated GAPD promoter fragments (QC690, QC690-1Y, 2Y, 3Y, 4Y, and 5Y) were tested by transiently expressing the reporter gene ZS-GREEN1 (GFP) or ZS-YELLOW1 N1 (YFP) in germinating soybean cotyledons. Soybean seeds were rinsed with 10% TWEEN® 20 in sterile water, surface sterilized with 70% ethanol for 2 minutes and then by 6% sodium hypochloride for 15 minutes. After rinsing the seeds were placed on wet filter paper in Petri dish to germinate for 4-6 days under light at 26° C. Green cotyledons were excised and placed inner side up on a 0.7% agar plate containing Murashige and Skoog media for particle gun bombardment. The DNA and gold particle mixtures were prepared similarly as described in EXAMPLE 4 except with more DNA (100 ng/µl). The bombardments were also carried out under similar parameters as described in EXAMPLE 4. YFP expression was checked under a Leica MZFLIII stereo microscope equipped with UV light source and appropriate light filters (Leica Microsystems Inc., Bannockburn, Ill.) and pictures were taken approximately 24 hours after bombardment with 8× magnification using a Leica DFC500 camera with settings as 0.60 gamma, 1.0 gain, 0.70 saturation, 61 color hue, 56 color saturation, and 0.51 second exposure (shown in black and white in FIG. 6A-FIG. 6H).

The full length GAPD promoter constructs QC690 had strong yellow fluorescence signals in transient expression assay similar to the positive control pZSL90 bp showing bright yellow dots in red background (shown as white dots on a black background in FIG. 6A-6H). Each dot represented a single cotyledon cell which appeared larger if the fluorescence signal was strong or smaller if the fluorescence signal was weak even under the same magnification (FIG. 6A-FIG. 6H). The attB2 site inserted between the GAPD promoter and YFP gene did not seem to interfere with promoter activity and reporter gene expression for the deletion constructs. The deletion construct QC690-1Y (FIG. 6D) with the 1148 bp GAPD promoter showed slightly reduced yellow fluorescence signals though comparable to the full length 1469 bp GAPD promoter construct QC690 (FIG. 6C) that has the GFP reporter gene. Further deletions of the GAPD promoter to 850, 637, 425, and 211 bp in constructs QC690-2Y (FIG. 6E), QC690-3Y (FIG. 6F), QC690-4Y (FIG. 6G), and QC690-5Y (FIG. 6H) resulted in gradual reductions of the promoter strength. Faint yellow dots were still detectable in even the shortest construct QC690-5Y (shown as white dots on a black background in FIG. 6A-6H), suggesting that as short as 211 bp GAPD promoter sequence upstream of the start codon ATG was long enough for the minimal expression of a reporter gene.

This data clearly indicates that all deletion constructs are functional as a constitutive promoter and as such SEQ ID NO: 2, 3, 4, 5, 6 are all functional fragment s of SEQ ID NO:1.

Example 7

GAPD:GFP Expression in Stable Transgenic Soybean Plants

The stable expression of the fluorescent protein reporter gene ZS-GREEN1 (GFP) driven by the full length GAPD promoter (SEQ ID NO:1, construct QC699) in transgenic soybean plants is shown as white tissues in FIG. 7A-FIG. 7P.

ZS-GREEN1 (GFP) gene expression was tested at different stages of transgenic plant development for green fluorescence emission under a Leica MZFLIII stereo microscope equipped with appropriate fluorescent light filters. Green fluorescence (shown as white in FIG. 7A-FIG. 7P.) was detectable in globular and young heart stage somatic embryos during the suspension culture period of soybean transformation (FIG. 7A). Moderate GFP expression was continuously detected in differentiating cotyledon somatic embryos placed on solid medium and then throughout later stages until fully developed drying down somatic embryos (FIG. 7B, FIG. 7C). The negative section of a positive embryo cluster emitted weak red color (shown as grey in FIG. 7A-FIG. 7P) due to auto fluorescence from the chlorophyll contained in soybean green tissues including embryos. The reddish green fluorescence indicated that the GFP expression was moderate since everything would be bright green if the GFP gene was driven by a strong constitutive promoter. When transgenic plants regenerated, GFP expression was detected in most tissues checked, such as flower, leaf, stem, root, pod, and seed (FIG. 7D-FIG. 7P). Negative controls for most tissue types displayed in FIG. 7A-FIG. 7P are not shown, but any green tissue such as leaf or stem negative for GFP expression would look red (illustrated as grey in the figures) and any white tissue such as root and petal would look dull yellowish under the GFP fluorescent light filter.

A soybean flower consists of five sepals, five petals including one standard large upper petal, two large side petals, and two small lower petals called kneel to enclose ten stamens and one pistil. The pistil consists of a stigma, a style, and an ovary in which there are 2-4 ovules. A stamen consists of a filament, and an anther on its tip. The filaments of nine of the stamens are fused and elevated as a single structure with a posterior stamen remaining separate. Pollen grains reside inside anther chambers and are released during pollination the day before the fully opening of the flower. Fluorescence signals were detected in sepals, petals, and pistils of both flower buds and open flowers and but hardly in stamens or ovules (FIG. 7D-FIG. 7G). Fluorescence signals were concentrated in the stomata guard cells of sepal and pistil as shown in close-up views (FIG. 7E, FIG. 7G).

Green fluorescence was detected mainly in the stomata guard cells and veins of fully developed leaf and stem (FIG. 7H, FIG. 7I), and the vascular bundles of stem, leaf petiole, and root of T0 adult plant (FIG. 7J-FIG. 7L). Strong fluorescence signals were primarily detected in the phloem of the vascular bundles of stem, leaf petiole, and root as clearly shown in their cross sections. Fluorescence signals were detected in pod coat also concentrated in the stomata guard cells as clearly shown in the close-up view (FIG. 7M).

Moderate fluorescence signals were detected in developing seeds of the GAPD:GFP transgenic plants from young R3 pod of ~5 mm long, to full R4 pod of ~20 mm long, until elongated pods filled with R5, R6 seeds (FIG. 7N-FIG. 7P). Fluorescence signals were concentrated in seed coat only in young R3, R4 seeds (FIG. 7N) and then in cotyledons and the inside of seed coat of older seeds (FIG. 7O, FIG. 7P). The seed and pod development stages were defined according to descriptions in Fehr and Caviness, IWSRBC 80:1-12 (1977).

In conclusion, GAPD:GFP expression was detected moderately in most tissues throughout transgenic plant development indicating that the soybean GAPD promoter is a moderate constitutive promoter, specifically with preferred strong expression in stomata guard cells.

What is claimed is:

1. A recombinant DNA construct comprising:
   (a) a nucleotide sequence comprising any one of the sequences set forth in SEQ ID NO:1, SEQ ID NO:2, SEQ ID NO:3, SEQ ID NO:4, SEQ ID NO:5, SEQ ID NO:6, SEQ ID NO:39; or,
   (b) a nucleotide sequence having at least 98% identity, based on the Clustal V method of alignment with pairwise alignment default parameters (KTUPLE=2, GAP PENALTY=5, WINDOW=4 and DIAGONALS SAVED=4), when compared to the sequence set forth in SEQ ID NO:1, operably linked to at least one heterologous sequence, wherein said nucleotide sequence is a constitutive promoter.

2. A vector comprising the recombinant DNA construct of claim 1.

3. A cell comprising the recombinant DNA construct of claim 1.

4. The cell of claim 3, wherein the cell is a plant cell.

5. A transgenic plant having stably incorporated into its genome the recombinant DNA construct of claim 1.

6. The transgenic plant of claim 5 wherein said plant is a dicot plant.

7. The transgenic plant of claim 6 wherein the plant is soybean.

8. A transgenic seed produced by the transgenic plant of claim 6, wherein the transgenic seed comprises the recombinant DNA construct.

9. The recombinant DNA construct of claim 1 wherein the at least one heterologous sequence codes for a gene selected from the group consisting of: a reporter gene, a selection marker, a disease resistance conferring gene, a herbicide resistance conferring gene, an insect resistance conferring gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in cold resistance, a gene involved in heat resistance and a gene involved in salt resistance in plants.

10. The recombinant DNA construct of claim 1, wherein the at least one heterologous sequence encodes a protein selected from the group consisting of: a reporter protein, a selection marker, a protein conferring disease resistance, a protein conferring herbicide resistance, a protein conferring insect resistance; a protein involved in carbohydrate metabolism, protein involved in fatty acid metabolism, a protein involved in amino acid metabolism, a protein involved in plant development, a protein involved in plant growth regulation, a protein involved in yield improvement, protein involved in drought resistance, a protein involved in cold resistance, a protein involved in heat resistance and a protein involved in salt resistance in plants.

11. A method of expressing a coding sequence or a functional RNA in a plant comprising:
  a) introducing the recombinant DNA construct of claim 1 into the plant, wherein the at least one heterologous sequence comprises the coding sequence or encodes the functional RNA;
  b) growing the plant of step a); and
  c) wherein said plant that expresses the coding sequence or the functional RNA is selected.

12. A method of transgenically altering a marketable plant trait of a plant, comprising:
  a) introducing a recombinant DNA construct of claim 1 into the plant, wherein expression of said recombinant DNA construct alters said marketable plant trait;
  b) growing a fertile, mature plant resulting from step a); and
  c) selecting a plant from step b) comprising said altered marketable trait.

13. The method of claim 12 wherein the marketable trait is selected from the group consisting of: disease resistance, herbicide resistance, insect resistance carbohydrate metabolism, fatty acid metabolism, amino acid metabolism, plant development, plant growth regulation, yield improvement, drought resistance, cold resistance, heat resistance, and salt resistance.

14. A method for altering expression of at least one heterologous sequence in a plant comprising:
  (a) transforming a plant cell with the recombinant DNA construct of claim 1;
  (b) growing fertile mature plants from transformed plant cell of step (a); and
  (c) selecting a plant containing the transformed plant cell wherein the expression of the at least one heterologous sequence comprised in the recombinant DNA construct of claim 1 is increased or decreased in said plant cell when compared to a corresponding non-transformed plant.

15. The method of claim 14 wherein the plant is a soybean plant.

16. A method for expressing a green fluorescent protein in a host cell comprising:
  (a) transforming a host cell with the recombinant DNA construct of claim 1, wherein the at least one heterologous sequence comprised in the recombinant DNA construct of claim 1 encodes for said green fluorescent protein; and,
  (b) growing the transformed host cell under conditions that are suitable for expression of the recombinant DNA construct, wherein expression of the recombinant DNA construct results in production of increased levels of green fluorescent protein in the transformed host cell when compared to a corresponding non-transformed host cell.

17. A plant stably transformed with a recombinant DNA construct comprising a soybean constitutive promoter and a heterologous nucleic acid fragment operably linked to said constitutive promoter, wherein said constitutive promoter controls the expression of said heterologous nucleic acid fragment in a plant cell, and further wherein said constitutive promoter comprises the sequence selected from the group consisting of SEQ ID NO:1, SEQ ID NO:2, SEQ ID NO:3, SEQ ID NO:4, SEQ ID NO:5, SEQ ID NO:6, and SEQ ID NO:39.

* * * * *